US012725713B2

(12) United States Patent
Shaul et al.

(10) Patent No.: US 12,725,713 B2
(45) Date of Patent: Sep. 1, 2026

(54) MULTIPLE INSTANCE LEARNER FOR TISSUE IMAGE CLASSIFICATION

(71) Applicant: HOFFMANN-LA ROCHE INC., Little Falls, NJ (US)

(72) Inventors: Ido Ben Shaul, Raanana (IL); Jacob Gildenblat, Holon (IL); Eldad Klaiman, Starnberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 1191 days.

(21) Appl. No.: 17/708,819

(22) Filed: Mar. 30, 2022

(65) Prior Publication Data

US 2022/0237788 A1 Jul. 28, 2022

Related U.S. Application Data

(63) Continuation of application No. PCT/EP2020/082917, filed on Nov. 20, 2020.

(30) Foreign Application Priority Data

Nov. 22, 2019 (EP) .................................... 19210814

(51) Int. Cl.

| | |
|---|---|
| ***G16H 50/70*** | (2018.01) |
| ***G06T 7/00*** | (2017.01) |
| ***G06V 10/44*** | (2022.01) |
| ***G06V 10/764*** | (2022.01) |
| ***G06V 10/77*** | (2022.01) |
| ***G06V 10/82*** | (2022.01) |

(Continued)

(52) U.S. Cl.

CPC ........... *G16H 50/70* (2018.01); *G06T 7/0012* (2013.01); *G06V 10/454* (2022.01); (Continued)

(58) Field of Classification Search

CPC ........ G16H 50/70; G16H 30/20; G16H 50/20; G16H 30/40; G06T 7/0012; (Continued)

(56) References Cited

U.S. PATENT DOCUMENTS 10,650,520 B1 * 5/2020 Beck ...................... G16H 50/20
2015/0242708 A1 8/2015 Duan et al.

(Continued)

FOREIGN PATENT DOCUMENTS

CN 109308495 A 2/2019
CN 109460756 A 3/2019

OTHER PUBLICATIONS

Ilse et al."Attention-based Deep Multiple Instance Learning" retrieved from arXiv:1802.04712v4 and published Jun. 28, 2018. (Year: 2018).*

(Continued)

*Primary Examiner* — Sanchita Roy

(74) *Attorney, Agent, or Firm* — Harness, Dickey & Pierce, P.L.C.

(57) ABSTRACT

The method includes, for each of a plurality of tiles of an image, extracting a feature vector from the tile; providing a Multiple-Instance-Learning program configured to use a model for classifying any input image as a member of one out of at least two different classes based on feature vectors extracted from the tiles; for each of the tiles, computing a certainty value indicating the certainty of the model regarding the contribution of the tile's feature vector on the classification of the image; for each of the images, using, by the MIL-program, a certainty-value-based pooling function for aggregating the feature vectors of the image or predictive values computed from the feature vectors of the image into an aggregated predictive value as a function of the certainty values of the tiles; and classifying each of the images as a member of one of the classes based on the aggregated predictive value.

20 Claims, 14 Drawing Sheets

(51) Int. Cl.
*G06V 20/69* (2022.01)
*G16H 30/20* (2018.01)
*G16H 50/20* (2018.01)
*G06N 3/084* (2023.01)

(52) U.S. Cl.
CPC ........ *G06V 10/764* (2022.01); *G06V 10/7715* (2022.01); *G06V 10/82* (2022.01); *G06V 20/695* (2022.01); *G06V 20/698* (2022.01); *G16H 30/20* (2018.01); *G16H 50/20* (2018.01); *G06N 3/084* (2013.01); *G06T 2200/24* (2013.01); *G06T 2207/20081* (2013.01); *G06T 2207/20084* (2013.01); *G06T 2207/30024* (2013.01)

(58) Field of Classification Search
CPC ....... G06T 2200/24; G06T 2207/20081; G06T 2207/20084; G06T 2207/30024; G06V 10/454; G06V 10/764; G06V 10/7715; G06V 10/82; G06V 20/695; G06V 20/698; G06N 3/084; G06F 18/214; G06F 18/2414
See application file for complete search history.

(56) References Cited

U.S. PATENT DOCUMENTS

| | | | | |
|---|---|---|---|---|
| 2018/0137338 | A1 | 5/2018 | Kraus et al. | |
| 2018/0295252 | A1 | 10/2018 | Watanabe | |
| 2019/0122073 | A1 * | 4/2019 | Ozdemir | G06V 20/56 |
| 2019/0172581 | A1 * | 6/2019 | Zlotnick | G06N 3/08 |
| 2019/0304092 | A1 * | 10/2019 | Akselrod-Ballin | G06N 3/084 |

OTHER PUBLICATIONS

Office Action for Japanese Application No. 2022-523835 dated Apr. 17, 2023 and English translation.
Maximilian Ilse et al., “Attention-based Deep Multiple Instance Learning”, arXiv, USA, Cornell University, Jun. 28, 2018, pp. 1-16, https://arxiv.org/abs/1802.04712.
Basura Fernando et al., “Deep Multiple Instance Learning with Gaussian Weighting”, ICLR 2020 Conference Blind Submission, USA, ICLR, Sep. 26, 2019, pp. 1-10, https://openreview.net/forum?id=Bklrea4KwS.
Kenta Murata, “Chapter 3, Introduction for deep learning, Problems that occur when layers increase and solutions therefor”, Web+DB Press, Japan, Gijutsu-Hyoron Co. Ltd., Nov. 25, 2015, vol. 89, pp. 62-66.
Yasufumi Sakai et al., “Dropout and DropConnect for Reliable Neuromorphic Inference Under Communication Constraints in Network Connectivity”, IEEE Journal on Emerging and Selected Topics in Circuits and Systems, USA, IEEE, Nov. 19, 2019, vol. 9, No. 4, pp. 658-667.
Yun Gu et al., “Reliable Label-Efficient Learning for Biomedical Image Recognition”, IEEE Transactions on Biomedical Engineering, USA, IEEE, Dec. 27, 2018, vol. 66, No. 9, pp. 2423-2432.
S. Kaymaka et al. ‘Breast cancer image classification using artificial neural networks’, *Procedia Computer Science*, vol. 120, 2017, pp. 126-131.
Y. Gal et al. ‘Deep Bayesian Active Learning with Image Data’, 2017, pp. 1-10.
J. Bromley et al. ‘Signature Verification using a “Siamese” Time Delay Neural Network’, *Conference Paper in Advances in Neural Information Processing Systems*, 1994, pp. 737-744.
J. Long et al. ‘Fully Convolutional Networks for Semantic Segmentation’, *CVPR 2015*, pp. 3431-3440.
R. Hadsell et al. ‘Dimensionality Reduction by Learning an Invariant Mapping’, *The Courant Institute of Mathematical Sciences*, New York University, 2006, CVPR 06, pp. 1-8.
P. Courtiol, et al. ‘Classification and Disease Localization in Histopathology Using Only Global Labels: a Weakly-Supervised Approach’, 2018, pp. 1-13.
B. Babenko ‘Multiple Instance Learning: Algorithms and Applications’, *Dept. of Computer Science and Engineering*, 2008, pp. 1-19.
K. He et al. ‘Deep Residual Learning for Image Recognition’, In Proc. *IEEE Conf. on Computer Vision and Pattern Recognition*, 2016, pp. 770-778.
K. Sirinukunwattana, et al. ‘Locality Sensitive Deep Learning for Detection and Classification of Nuclei in Routine Colon Cancer Histology Images’, *IEEE Transactions on Medical Imaging*, vol. 35, No. 5, 2016, pp. 1196-1206.
M. Ilse et al. ‘Attention-based Deep Multiple Instance Learning’, 2018, pp. 1-16.
Anonymous Authors ‘Deep Multiple Instance Learning With Gaussian Weighting’, *ICLR* 2020, pp. 1-10.
M. Caron et al. ‘Deep Clustering for Unsupervised Learning of Visual Features’, 2018, pp. 1-30.
S. Gidaris et al. ‘Unsupervised Representation Learning by Predicting Image Rotations’, *ICLR*, 2018, pp. 1-16.
E. Hoffer, et al. ‘Semi-Supervised Deep Learning by Metric Embedding’, Workshop track—*ICLR* 2017, pp. 1-10.
O. Ronneberger et al. ‘U-Net: Convolutional Networks for Biomedical Image Segmentation’, *Computer Science Department and BIOSS Centre for Biological Signalling Studies*, 2015, pp. 1-8.
Japanese Office Action, dated Jul. 26, 2023, issued in corresponding Japanese Patent Application No. 2022-523835 and English translation.
Maximilian Ilse et al: “Attention-based Deep Multiple Instance Learning”, arxiv.org, Cornell University Library, 201, Olin Library Cornell University Ithaca, NY 14853, Feb. 13, 2018 (Feb. 13, 2018), XP081235680.
Anonymous: “Deep Multiple Instance Learning With Gaussian Weighting”, ICLR 2020 Conference Blind Submission, Sep. 25, 2019 (Sep. 25, 2019), pp. 1-10, XP055698116, Retrieved from the Internet: URL:https://openreview.net/attachment?id=Bklrea4KwS &name=original pdf [retrieved on May 25, 2020].
Nitish Srivastava et al: “Dropout: a simple way to prevent neural networks from overfitting”, Journal of Machine Learning Research, vol. 15, No. 1, Jun. 2014 (Jun. 2014), pp. 1929-1958, XP055193568.
Jacob Gildenblat et al: “Certainty Pooling for Multiple Instance Learning”, arxiv.org, Cornell University Library, 201 Olin Library Cornell University Ithaca, NY 14853, Aug. 24, 2020 (Aug. 24, 2020), XP081747325.
Liu Dong et al: “Adaptive Pooling in Multi-instance Learning for Web Video Annotation”, 2017 IEEE International Conference on Computer Vision Workshops (ICCVW), IEEE, Oct. 22, 2017 (Oct. 22, 2017), pp. 318-327, XP033303472.
Yan Yongluan et al: “Deep Multi-instance Learning with Dynamic Pooling”, Proceedings of Machine Learning Research, vol. 95, Nov. 14, 2018 (Nov. 14, 2018), pp. 662-677, XP055772935, Retrieved from the Internet: URL:http://proceedings.mlr.press/v95/yanl8a/yanl8a.pdf>.
Yun Wang et al: “A Comparison of Five Multiple Instance Learning Pooling Functions for Sound Event Detection with Weak Labeling”, ICASSP 2019—2019 IEEE International Conference on Acoustics, Speech, and Signal Processing : Proceedings : May 12-17, 2019, Brighton Conference Centre, Brighton, United Kingdom, May 12, 2019 (May 12, 2019), pp. 31-35, XP055763644.
Yarin Gal et al: “Deep Bayesian Active Learning with Image Data”, arxiv.org, Cornell University Library, 201 Olin Library Cornell University Ithaca, NY 14853, Mar. 8, 2017 (Mar. 8, 2017), XP080755269.
Le Hou et al: “Patch-Based Convolutional Neural Network for Whole Slide Tissue Image Classification”, 2016 IEEE Conference on Computer Vision and Pattern Recognition (CVPR), Jun. 26, 2016 (Jun. 26, 2016), pp. 2424-2433, XP055532412.
Ruoyu Li et al: “Graph CNN for Survival Analysis on Whole Slide Pathological Images” In: “21st International Conference on Medical Image Computing and Computer Assisted Intervention (MICCAI 2018)”, Sep. 16, 2018 (Sep. 16, 2018), Springer, XP055698010, ISSN: 0302-9743 vol. 11071, pp. 174-182.

(56) References Cited

OTHER PUBLICATIONS

International Search Report and Written Opinion for International Application No. PCT/EP2020/082917 dated Apr. 12, 2021.
Search Report for European Application No. 20 807 782.6 dated Apr. 25, 2024.
Momeni Alexandre et al: "Dropout-Enabled Ensemble Learning for Multi-scale Biomedical Data," Jan. 26, 2019 (Jan. 26, 2019), Brainlesion: Glioma, Multiple Sclerosis, Stroke and Traumatic Brain Injuries; [Lecture Notes in Computer Science; Lect.Notes Computer], Springer International Publishing, Cham, pp. 407-415, XP047680400, ISSN: 0302-9743, ISBN: 978-3-030-11722-I [retrieved on Jan. 26, 2019].
Raczkowski Lukasz et al: "ARA: accurate, reliable and active histopathological image classification framework with Bayesian deep learning," Scientific Reports, vol. 9, No. 1, Oct. 4, 2019 (Oct. 4, 2019), pp. 1-12, XP055842626, US, ISSN: 2045-2322, DOI: 10.1038/s41598-019-50587-1, pp. 1-4.
International Preliminary Report on Patentability dated Jun. 2, 2022 issued in corresponding international patent application No. PCT/EP2020/082917.
Office Action for Chinese Application No. 202080078832.9 dated Jan. 2, 2025 and English translation.
Heather Couture, "Multiple Instance Learning for Heterogeneous Images: Training a CNN for Histopathology," Springer Nature Switzerland 2018, pp. 254-262.
Notice of Allowance for Chinese Application No. 202080078832.9 dated Apr. 25, 2025.

* cited by examiner

| Training Method | Instance level prediction AUC | Bag prediction AUC | Bag prediction with Max Pooling AUC | Bag prediction with Uncertainty Max Pooling AUC |
|---|---|---|---|---|
| Attention on embeddings | 77.02% | 77.97% | 77.25% | 80.22% |
| Mean Pooling | 66.52% | 61.4% | 83.12% | 83.77% |
| Max Pooling | 78.67% | 87.3% | 87.3% | **87.95%** |
| Uncertainty Mean Pooling on predictions | **85.02%** | 78.35% | 82.12% | 82.70% |
| Uncertainty Mean Pooling on embeddings | **85.02%** | 78.35% | 81.07% | 81.62% |
| Uncertainty Max Pooling | 82.32% | 87.75% | 87.75% | 87.75% |

| Training Method | Instance level prediction AUC | Bag prediction AUC | Bag prediction with Max Pooling AUC | Bag prediction with Uncertainty Max Pooling AUC |
|---|---|---|---|---|
| Max Pooling | 88.55% | 90.74% | 90.74% | 90.74% |
| Mean Pooling | 87.65% | 85.82% | 90% | 90.74% |
| Attention based MIL on embeddings | 89.33% | 90.31% | 86.32% | 86.32% |
| Uncertainty Mean Pooling on predictions | 85.97% | 90.95% | 91.09% | 91.17% |
| Uncertainty Max Pooling | 90.2% | 92.31% | 92.31% | 92.31% |

Figure 8:
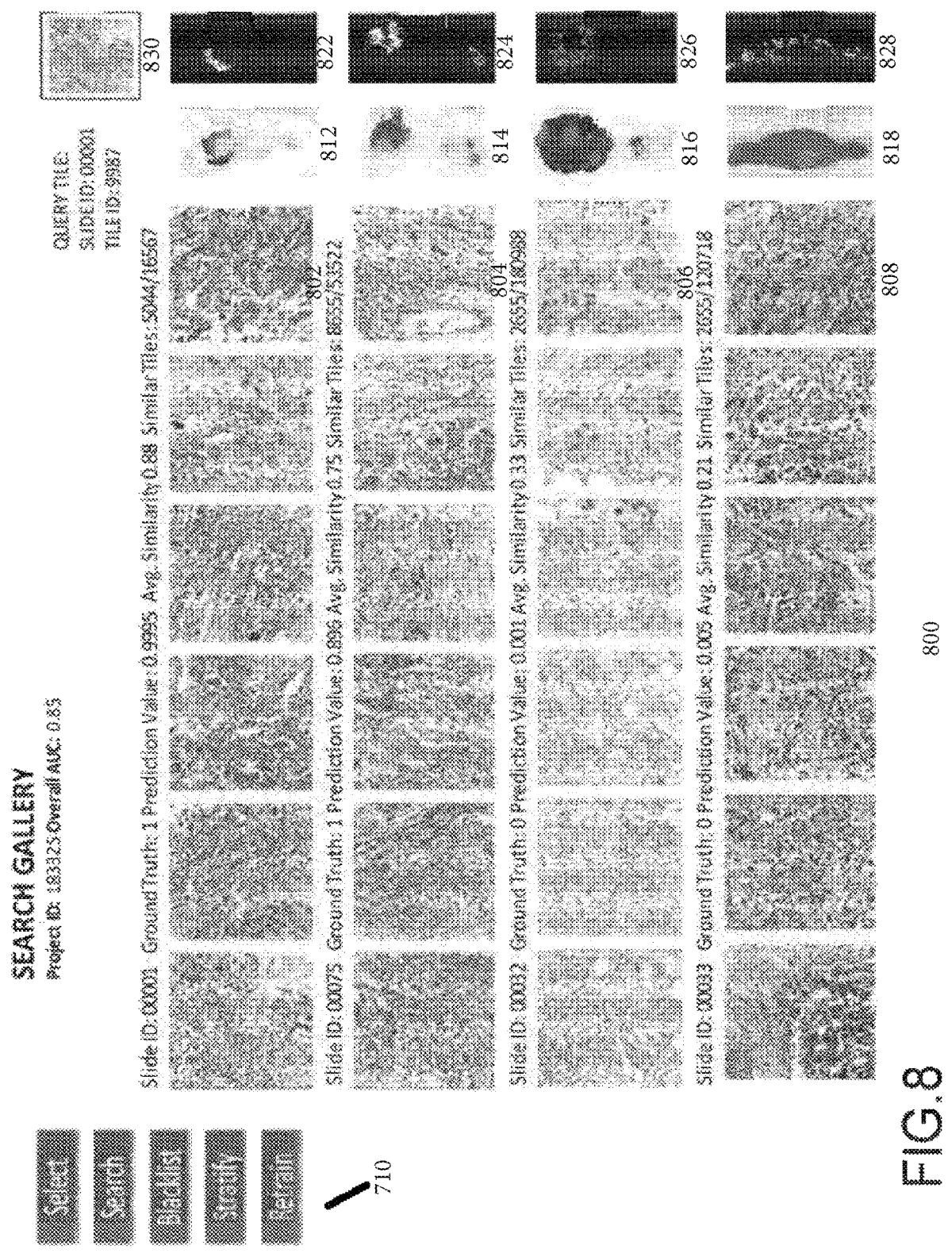

SEARCH GALLERY
Project ID: 183325 Overall AUC: 0.85

Select
Search
Blacklist
Stratify
Retrain
710

QUERY TILE:
SLIDE ID: 00001
TILE ID: 9987
830

Slide ID: 00001 Ground Truth: 1 Prediction Value: 0.9995 Avg. Similarity 0.88 Similar Tiles: 5044/16567
802 812 822

Slide ID: 00075 Ground Truth: 1 Prediction Value: 0.896 Avg. Similarity 0.75 Similar Tiles: 8655/53522
804 814 824

Slide ID: 00032 Ground Truth: 0 Prediction Value: 0.001 Avg. Similarity 0.33 Similar Tiles: 2655/180988
806 816 826

Slide ID: 00033 Ground Truth: 0 Prediction Value: 0.005 Avg. Similarity 0.21 Similar Tiles: 2655/120718
808 818 828

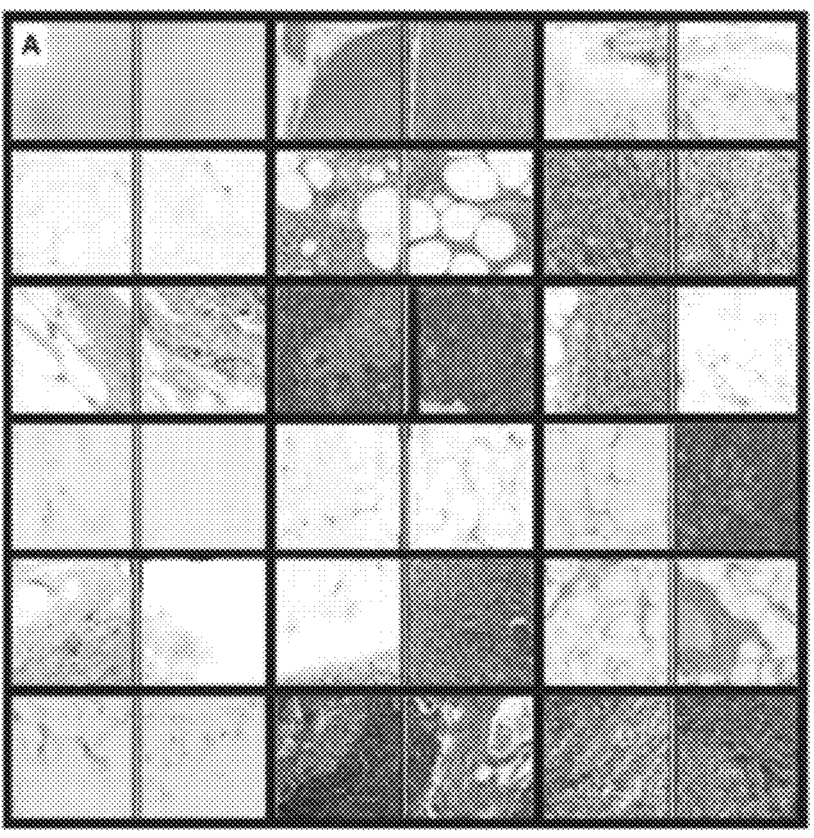
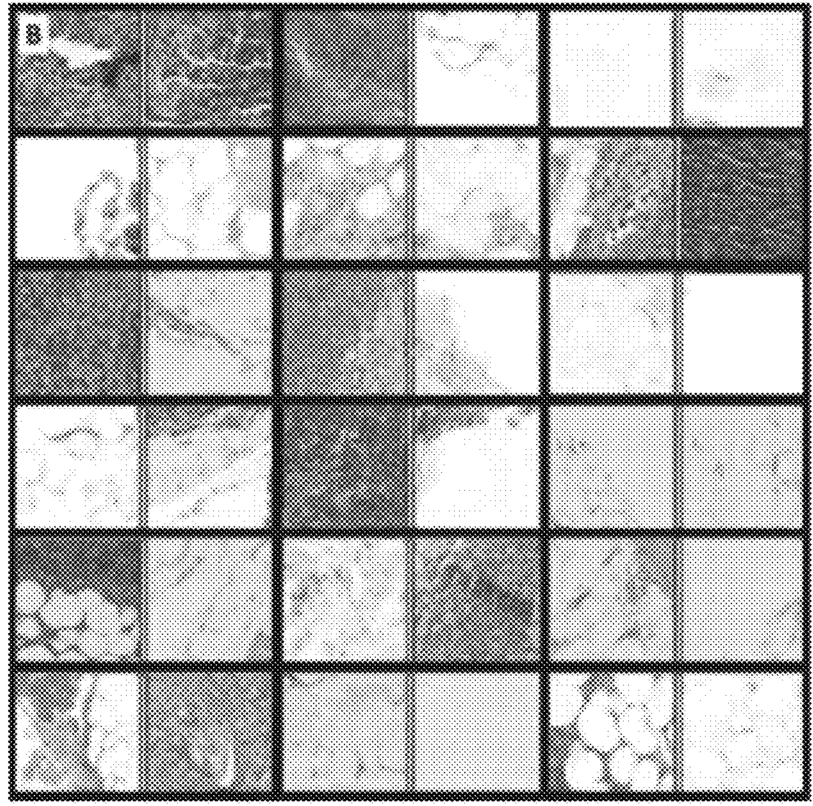
Fig. 13

MULTIPLE INSTANCE LEARNER FOR TISSUE IMAGE CLASSIFICATION

CROSS-REFERENCE TO RELATED APPLICATIONS

This application is a Bypass Continuation of PCT International Application No. PCT/EP2020/082917 which has an International filing date of Nov. 20, 2020, which claims priority to European Application No. 19210814.0, filed Nov. 22, 2019, the entire contents of each of which are hereby incorporated by reference.

FIELD OF THE INVENTION

The invention relates to the field of digital pathology, and more particular to the field of image analysis.

BACKGROUND AND RELATED ART

Several image classification methods are known which can be used to classify digital pathology images into different categories such as "healthy tissue" or "cancer tissue" or the like. For example, Sertan Kaymaka et al. in "Breast cancer image classification using artificial neural networks", Procedia Computer Science, Volume 120, 2017, Pages 126-131, describes a method for automatic classification of images for breast cancer diagnosis that uses Back Propagation Neural Network (BPPN).

However, applicant has observed that various machine-learning techniques, which provide good results in the early detection of cancer-related nodes within a mammography image, fail to classify images of other types of tissue sections, in particular whole-slide images.

A further problem associated with the use of existing machine learning approaches for image classification is that the trained machine learning programs often act like a black box. It is unsatisfactory for physicians and patients alike to have to rely completely or partially on this "black box" when deciding whether the administration of a potentially effective but side-effect rich drug to a certain patient makes sense, without being able to verbalize the underlying "decision logic".

MAXIMILIAN ILSE ET AL: "Attention-based Deep Multiple Instance Learning", ARXIV.ORG, CORNELL UNIVERSITY LIBRARY, 201 OLIN LIBRARY CORNELL UNIVERSITY ITHACA, N.Y. 14853, 13 Feb. 2018, XP081235680, describes the application of an attention-based Multiple Instance Learner (MIL) on a histopathology data set.

An anonymous publication "DEEP MULTIPLE INSTANCE LEARNING WITH GAUSSIAN WEIGHTING", ICLR 2020 Conference Blind Submission, 25 Sep. 2019 (2019 Sep. 25), pages 1-10, XP055698116, Retrieved from the Internet on 2020 May 25 from URL: https://openreview.netiattachment?id.Bklrea4KwS&name=original.pdf describes a deep Multiple Instance Learning (MIL) method that is trained end-to-end to perform classification from weak supervision. The MIL method is implemented as a two stream neural network, specialized in tasks of instance classification and weighting making use of Gaussian radial basis function to normalize the instance weights by comparing instances locally within the bag and globally across bags.

SUMMARY

It is an objective of the present invention to provide for an improved method of classifying tissue images and a corresponding image analysis system as specified in the independent claims. Embodiments of the invention are given in the dependent claims. Embodiments of the present invention can be freely combined with each other if they are not mutually exclusive.

In one aspect, the invention relates to a method for classifying tissue images. The method comprises:

- receiving, by an image analysis system, a plurality of digital images; each of the digital images depicts a tissue sample of a patient;
- splitting, by the image analysis system, each received image into a set of image tiles;
- for each of the tiles, computing, by the image analysis system, a feature vector comprising image features extracted selectively from the tile;
- providing a Multiple-Instance-Learning (MIL) program configured to use a model for classifying any input image as a member of one out of at least two different classes based on the feature vectors extracted from all tiles of the said input image;
- for each of the tiles, computing a certainty value (referred herein according to embodiments of the invention as "c"); the certainty value is indicative of the certainty of the model regarding the contribution of the tile's feature vector on the classification of the image from which the tile was derived;
- for each of the images:
  - using, by the MIL-program, a certainty-value-based pooling function for aggregating the feature vectors extracted from the image into a global feature vector as a function of the certainty values of the tiles of the image, and computing an aggregated predictive value (referred herein according to embodiments of the invention as "ah") from the global feature vector; or
  - computing, by the MIL program, predictive values from respective ones of the feature vectors of the image and using, by the MIL-program, a certainty-value-based pooling function for aggregating the predictive values of the image into an aggregated predictive value (referred herein according to embodiments of the invention as "ah") as a function of the certainty values of the tiles of the image; and
- classifying, by the MIL-program, each of the images as a member of one out of the at least two different classes based on the aggregated predictive value.

These features may be beneficial for multiple reasons:

A Multiple instance learning (MIL) program is a form of weakly supervised learning program configured to learn from a training set wherein training instances are arranged in sets called bags, and wherein a label is provided for the entire bag while the labels of the individual instances in the bag are not known. Hence, a MIL-program requires only weakly annotated training data. This type of data is especially common in medical imaging because the annotation of individual image regions to provide richly annotated training data is highly time consuming and hence expensive. Furthermore, the tissue structures which imply (have high predictive value for . . . ) a digital image to be member of a particular class (e.g. image depicting healthy tissue/image depicting a primary tumor/image depicting a metastase) are sometimes not known or are not perceivable by a pathologist. Hence, using a MIL-program for classifying digital tissue images may have the advantage that weakly annotated training data is sufficient for training a MIL-program capable of accurately classifying digital tissue images. Furthermore, the trained MIL-program will be able to accurately classifying digital tissue images even in case a human annotator, e.g. a pathologist, does not know the tissue structures which are highly predictive of the class membership of the tissue and hence is not able to select training images having an unbiased ratio of tissue regions with and without this tissue structure.

Furthermore, using a MIL-program with a certainty-value-based pooling function incorporates model uncertainty into the classification. Applicant has observed that this considerably improves classification accuracy in particular in the domain of tissue slide image analysis, in particular when the tissue slide images are whole slide images.

When a MIL-program is used for solving problems of computational pathology, whole slide images (WSI) to be used as training images are given a global label (e.g. indicating if tumor cells exist in a biopsy). Multiple instances are then extracted from the training WSIs by sampling image tiles from the training WSIs, and are grouped into bags, where every bag contains the tiles extracted from a specific training WSI and has that slide image's global label.

In many cases just a small portion of the instances (tiles) will contain evidence for the WSI label e.g. when the tumor is localized in a small part of the biopsy. In addition, the sizes of the bags (number of tiles per training WSI) can be very large due to the large size of the tissue in the WSIs in full resolution (in the order of many thousands of instances or more). These factors form a challenging MIL setting. As the bags grow larger, a larger negative instance population in the bag presents a growing probability for the bag to be falsely classified, since there are more opportunities to find evidence of the positive class. This is magnified by the unstable nature of deep learning models, where a small change in the input image can trigger a very different output. Because of this, a large bag that contains many visually similar looking instances, might result in very different feature vectors and respective predictions and predictive values for each of them. Applicant has observed that taking into account not only the feature values (or predictive values derived from the feature vectors) of the tiles but also the certainty values considerably ameliorates this problem, because the uncertainty of the model in respect to the tissue textures and image features depicted in a particular tile are taken into account.

According to embodiments, the certainty-value-based pooling function is a certainty-value based max-pooling, mean-pooling or an attention pooling function.

Pooling functions are a key element in MIL. The pooling function dictates how the instances of the MIL model, i.e., the predictions of the tiles of an image, are combined to form the bag output, i.e., the classification result for the image. Several pooling functions exist, e.g. max-pooling, mean-pooling and attention pooling. However, applicant has observed that in the case of a low evidence ratio bag (e.g. small number of positive instances compared to the total number of instances) if max-pooling is used, a single false positive instance prediction will corrupt the resulting bag prediction and create a false positive result. On the other hand, if mean-pooling is used, a large negative instance population in the bag will overshadow the positive instances and create a false negative bag prediction.

In the case of learned attention MIL, the attention learning is significantly and negatively affected in the case of low evidence ratios. An additional challenge large bags pose is with model interpretability by selecting key instances. A larger bag presents a higher probability for instability potentially leading to mistakes in key instance selection. Hence, the use of a certainty-value-based pooling function is particularly advantageous in the context of digital tissue images, in particular whole slide images.

Using a certainty-value-based pooling function addresses the shortcomings of the current pooling functions and deals with the underperformance of MIL in the case of bags with low evidence ratio as often the case with (whole slide) tissue images. For example, by weighting the feature vectors (or predictive values derived therefrom) by a certainty value computed for this instance, the uncertainty of the model for every instance is taken into account.

Classifying digital tissue images can be used for assessing the chances of successfully treating a patient afflicted with a disease with a particular drug. For example, some drugs used in the course of immunotherapy in cancer patients only work if certain immune cells are found at a certain distance from the cancer cells. In this case, an attempt is made to automatically recognize these objects, i.e. certain cell types or certain sub- and super-cellular structures, in a tissue image in order to be able to make a statement about the presence and/or recommended treatment of a disease. Embodiments of the invention may have the advantage that they make use of a MIL-program and hence do not require that the relationships between certain tissue structures and certain diseases or their treatment options are explicitly known. By training and using a trained MIL-program, it is possible to implicitly detect unknown predictive features concerning a certain disease and/or its treatment. Embodiments of the invention are therefore not limited to the medical knowledge available at a certain time.

In a further beneficial aspect, using a MIL-program that treats image tiles as instances is particularly suited for predicting the patient-related feature in the context of whole slide tissue sample images. This is because often whole slide tissue samples cover many different tissue regions only some of which may have any predictive value. For example, a micrometastase may only be a few millimeters in diameter but the slide and the respective whole-slide image may be many cm long. Although the whole image is labeled—in accordance with the empirical observation for the patient from whom the sample was derived—with a particular label, e.g. "responsive to drug D=true", the tissue region around the micrometastase that comprises many immune cells and that is predictive for the positive response may also cover only a few millimeters. Hence, the majority of the tiles do not comprise any tissue region that is predictive in respect to the image-wise and typically patient-wise label. MIL-programs are particularly suited for identifying predictive features based on bags of data instances where a large portion of the instances is assumed not to be of any predictive value.

The MIL is configured to treat all tiles derived from said digital images as members of the same bag of tiles.

According to embodiments, the method further comprises outputting, via a GUI, the classification result to a user. In addition, or alternatively, the method comprises outputting the classification result to another application program. For example, the MIL-program can be part of or can be interoperable with an image classification application program that is configured to generate a GUI that displays the result of the classification to a user. For example, each of the received digital images can be displayed on the GUI in association with a label being indicative of the class comprising, according to the classification result generated by the MIL-program, the respective digital image.

According to embodiments, the MIL-program is a binary MIL-program. The at least two classes consist of a first class referred to as "positive class" and a second class referred to as "negative class". Any one of the images is classified into the "positive class" if the MIL model predicts for at least one of the tiles of this image that the feature vector of this tile comprises evidence for the "positive class". Any one of the images is classified into the "negative class" if the MIL model predicts for all the tiles of this image that their respective feature vectors do not comprises evidence for the "positive class". For example, the question whether or not a sufficient number of tiles comprises sufficient evidence for the "positive class" may comprise using the certainty-value-based pooling function for determining whether the aggregated predictive value exceed a threshold value.

In some embodiments, the feature vectors computed for the tiles can comprise one or more "positive feature values" and one or more "negative feature values". A "negative feature value" is a value of a feature that provides evidence for the "negative class". A "positive feature value" is a value of a feature that provides evidence for the "positive class". In this case, the MIL-program is configured to take into account both the negative and positive feature value for classifying the image.

The predicted membership of an image in a particular class can be implemented as assigning a class label that is indicative of a class membership to the image. The "class label" to be assigned to a particular digital image can also be referred to as "bag label" as the image represents a "bag" and the tiles generated from the image represent "instances" of the bag.

For example, the MIL-program can be a binary MIL-program where a binary label is assigned to every bag. The MIL-program has learned and is configured to predict that a particular digital image has a "positive" bag label if at least one of the instances (tiles) of this image contains evidence for the label. The image is predicted to have a "negative" bag label if all of the instances do not contain evidence for the "positive" class label.

More formally, every bag (image) is composed of a group of instances $\{x_1, \ldots, x_K\}$, where K is the size of the bag, i.e., the number of tiles generated from the digital image. K can vary between the bags (received digital images). A binary class label $Y \in \{0, 1\}$ is associated with every bag (image). Every instance (tile) j also has a label $y_j \in \{0, 1\}$, however it is assumed the instances labels (tile labels) are hidden. "0" represents a negative instance or bag label and "1" represents a positive instance or bag label. The MIL-program is configured to predict a binary bag label (class membership) Y for a bag (image) by applying a pooling function on all instance labels for computing/predicting the bag label. For example, a state of the art MIL program using a max pooling function would compute the binary bag label Y according to: $Y=\{0, \text{iff } \Sigma y_K=0, \text{otherwise } 1\}$. However, the MIL-program according to embodiments of the invention uses a new pooling function that takes into account model uncertainty.

MIL-programs comprise a pooling function that is applied to aggregate the instance predictions (individual tile-based predictions) h to create a prediction (classification result) for the bag (the image).

Approach I Based on Tile-Based Predictive Values

According to embodiments, the MIL-program uses the certainty-value-based pooling function for aggregating the predictive values computed for the tiles of the image into the aggregated predictive value. The method comprises computing, by the MIL-program, for each of the tiles, one of the predictive values (referred herein according to embodiments of the invention as "h"). Each predictive value is computed as a function of the feature vector extracted from the tile. The predictive value is a data value indicating the contribution of the tile's feature vector on the classification of the image from which the tile was derived. When computing the predictive value for a particular tile, the MIL-program preferably takes into account only the feature vector of the tile from which the feature vector was derived (and not the feature vector of any other tile).

According to embodiments, the certainty-value-based pooling function is a certainty-value-based-max-pooling function. The use of the certainty-value-based pooling function comprises, for each of the images, a sub-method a), or b, respectively comprising:

- a1) weighting the predictive value (referred to e.g. as "h") of each of the tiles with the certainty value (referred to e.g. as "c") computed for this tile, thereby obtaining a weighted predictive value (referred to e.g. as "wh"); for example, the weighting comprises multiplying the certainty value (c) computed for one of the tiles with the predictive value (h) computed for the one tile for computing the weighted predictive value (wh) of the tile; for example, for a particular image $I_m$ that was split into K tiles, the weighted predictive value $wh_{m\_k}$ for any one of the K tiles can be computed as: $wh_{m\_k}=h_{m\_k} \times c_{m\_k}$;
- a2) identifying the maximum (referred to e.g. as "$wh_{MAX}$") of all weighted predictive values computed for all the tiles of the image; for example, the maximum is computed according to: $wh_{MAX}(I_m)=\max(wh_{k_m})$; and
- a3) using the maximum weighted predictive value ($wh_{MAX}(I_m)$) as the aggregated predictive value; or
- b) using the predictive value (h) of the tile with the maximum certainty value ($c_{max}$) as the aggregated predictive value.

If the predictive value (h) of the tile with the maximum certainty value (c) is used as the aggregated predictive value, the certainty value c is computed only in order to select the predictive value h. In this case, the selected predictive value h is considered to be "implicitly" weighted by the certainty value because it is selected as the aggregate predictive value in dependence on the certainty values computed for the tiles of the image.

The aggregated predictive value is then used for classifying the input image. For example, in case $wh_{MAX}$ exceeds a threshold determined during training, a digital image may be classified as "image depicting a tumor". Otherwise, the image is classified as "image depicting healthy tissue".

Using a certainty-value-based-max-pooling function may have the advantage that the MIL-program is more robust against situations at test or training time when a large negative instance (tiles having a "negative class" tile label) population in the bag (image) can potentially overshadow the positive instances (tiles having a "positive class" label) and can potentially create a false negative bag class prediction.

According to embodiments, the providing of the MIL-program comprises training the MIL-program on a training image set, whereby during the training phase a certainty-value-based-max-pooling function is used as pooling function. This may have the advantage that the predictive model generated during the training the MIL strongly reflects the tissue pattern depicted in the tile having the feature vector with the highest predictive power in respect to the bag's label. The model is not negatively affected by tissue regions/tiles which are irrelevant for the label. However, the maximum operation will neglect all the information contained in all tiles except the highest scoring tile. Hence, the predictive power of tiles/tissue patterns which may also be of relevance may be missed.

According to embodiments, the providing of the MIL-program comprises training the MIL-program on a training image set, whereby during the training phase a certainty-value-based-mean-pooling function is used as pooling function. This may be beneficial as the predictive model generated when training the MIL-program takes into account the tissue patterns depicted in all tiles. However, the consideration of tissue patterns and respective tiles which are actually irrelevant for the occurrence of a particular label may result in a deterioration and reduction of the predictive accuracy of the trained MIL.

According to embodiments, certainty-value-based pooling function is a certainty-value-based-mean-pooling function. The using of the certainty-value-based pooling function comprises, for each of the images:

- weighting the predictive value (referred to e.g. as "h") of each of the tiles with the certainty value (referred to e.g. as "c") computed for this tile, thereby obtaining a weighted predictive value (referred to e.g. as "wh"); for example, the weighting comprises multiplying the certainty value (c) computed for one of the tiles with the predictive value (h) computed for the one tile for computing the weighted predictive value (wh) of the tile; for example, for a particular image $I_m$ that was split into K tiles, the weighted predictive value $wh_{m\_k}$ generated by the model for image $I_m$ for any one of the K tiles can be computed as: $wh_{m\_k}=h_{m\_k}\times c_{m\_k}$;
- computing the mean (referred to e.g. as "$wh_{MEAN}$") of all weighted predictive values wh computed for all the tiles of the image; for example, the mean is computed according to:

$$wh_{MEAN}(I_m) = \frac{1}{K}\sum_{k=1}^{K} wh_{k\_m};$$

according to an alternative embodiment, the mean is computed according to:

$$wh_{MEAN}(I_m) = \sum_{k=1}^{K} h_{k\_m} \ x \ softmax(c_{k\_m});$$

- and using the mean weighted predictive value ($wh_{MEAN}(I_m)$) as the aggregated predictive value.

Using a certainty-value-based-mean-pooling function may have the advantage that the MIL-program is more robust against false positive predictions that the image is member of the "positive class" in the context of low evidence ratio bags than a maximum operator based pooling function. A "low evidence ratio bag" is a bag of instances wherein the number of positive instances (tiles with "positive class" label) is very small compared to the total number of instances (tiles)). If max-pooling is used, a single false positive instance prediction will corrupt the resulting bag prediction and create a false positive classification result.

Approach II Based on a Global Aggregated Feature Vector

According to alternative embodiments, the MIL-program uses the certainty-value-based pooling function for aggregating the feature vectors extracted from the tiles of the image into a global ("aggregated") feature vector that again is used for computing the aggregated predictive value. The method comprises:

- applying the pooling function on the feature vectors and certainty values computed for the tiles of the image for computing a global feature vector for the image, the computation of the global feature vector taking into account the feature vectors of the tiles and the certainty values; and
- using the global feature vector to calculate the aggregated predictive value.

According to embodiments, the certainty-value-based pooling function is a certainty-value-based-max-pooling function.

According to one embodiment, the use of the certainty-value-based max-pooling function comprises, for each of the images, a sub-method c), or d), respectively comprising:

- c1) weighting the feature vector (referred to e.g. as "fw")) of each of the tiles with the certainty value (referred to e.g. as "c") computed for this tile, thereby obtaining a weighted feature vector (referred to e.g. as "wfv"); for example, the features of the feature vector may consist of numerical feature vectors only; the weighting comprises multiplying the certainty value (c) computed for one of the tiles with each feature value in the feature vector (fv) computed for the one tile for obtaining the weighted feature vector (fv) of the tile;
- c2) identifying the maximum of all weighted feature vectors ($wfv_{max}$) computed for all the tiles of the image; or
- d) using the feature vector (fv) of the tile with the maximum certainty value ($c_{max}$) as the global feature vector.

For example, embodiments according to sub-method d) may be used in case the feature vectors comprise ordinal values which cannot be weighted by a simple multiplication.

According to other embodiments, the certainty-value-based pooling function is a certainty-value-based-mean-pooling function. The use of the certainty-value-based pooling function comprises, for each of the images:

- weighting the feature vector (referred to e.g. as "h") extracted from each of the tiles with the certainty value (referred to e.g. as "c") computed for this tile, thereby obtaining a weighted feature vector (referred to e.g. as "wfv"); for example, each feature vector may comprise a plurality of numerical feature values and each numerical feature value of the feature vector is multiplied with the certainty value to obtain weighted feature vector values stored in the weighted feature vector of a particular tile;
- computing a mean weighted feature vector from all weighted feature vectors (wfv) computed for the image; for example, the feature values of the mean weighted feature vector can be computed as the mean of all weighted feature values stored in the weighted feature vectors of the image in the same vector position;
- and using the mean weighted feature vector computed for the image as the global feature vector of the image that is used to calculate the aggregated predictive value.

Further Embodiments (Approach I and II)

According to other embodiments, the method comprises, for each of the images, normalizing the certainty values computed for the image by applying a softmax function on the certainty values. The certainty-value-based pooling function is configured to aggregate the predictive values into the aggregated predictive value as a function of the normalized certainty values or to aggregate feature vectors into the global feature vector as a function of the normalized certainty values, whereby the global feature value is used for computing the aggregated predictive value.

The softmax function, also known as softargmax or normalized exponential function, is a function that takes as input an array of K real numbers, e.g. K certainty values $c_k$ computed for each of the K tiles of an image $I_m$, and normalizes it into a probability distribution consisting of K probabilities proportional to the exponentials of the input numbers. That is, prior to applying softmax, some array components could be negative, or greater than one; and might not sum to 1; but after applying softmax, each component will be in the interval (0, 1), and the components will add up to 1, so that they can be interpreted as probabilities. Furthermore, the larger input components will correspond to larger probabilities. Softmax maps the non-normalized output of the network to a probability distribution over predicted output classes or ranges.

For example, the softmax function can be used for normalizing the certainty values into numerical values of a value range between 0 and 1. Using the softmax function for normalizing the certainty values may have the advantage that the comparability of the certainty values obtained for different tiles and/or different images is increased.

According to embodiments, the MIL-program comprises and is configured to execute the certainty-value-based pooling function instead of one or more of the following (conventional) pooling functions:

- a max-pooling function configured to identify and return the maximum of all predictive values h computed from all feature vectors extracted from the tiles of an image; for example, a conventional aggregate predictive value for a particular image $I_m$ can be computed as $ah_{conventional}(I_m)=\max(h_{k\_m})$;
- a mean-pooling function configured to identify and return the mean of all predictive values h computed from all feature vectors extracted from the tiles of an image; for example, a conventional aggregate predictive value for a particular image $I_m$ can be computed as $$ah_{conventional}(I_m) = \frac{1}{K}\sum_{k=1}^{K} h_{k\_m};$$

- an attention-pooling function configured to identify and return the predictive value h of the one of the feature vectors having been identified by an attention learning technique to have the highest predictive power in respect to the class membership of the image from which the tile was derived among all feature vectors extracted from the tiles of the image; for example, a conventional aggregate predictive value for a particular image $I_m$ can be computed as $$ah_{conventional}(I_m) = \frac{1}{K}\sum_{k=1}^{K} (\alpha_{k\_m} \times h_{k\_m});.$$

Hence, according to embodiments of the invention, the new certainty-value-based pooling function replaces conventional pooling functions used in conventional MIL-programs (generally or selectively at training phase or test phase). The MIL-program according to embodiments of the invention does not comprise or use any one of the above-mentioned three conventional pooling functions for determining the bag label/performing the image classification task (generally or selectively at training phase or test phase).

According to embodiments, the MIL-program is a neural network. The certainty-value is computed using a dropout technique at training and/or test time of the model of the neural network.

Dropout is a technique that randomly turns off some neurons from a fully connected layer. Typically, dropout is applied (only) during training. The dropout forces the fully connected layers to learn the same concept in different ways. Dropout means that a certain fraction of neurons of a particular layer is deactivated ("dropped out") randomly. This improves generalization capabilities of the trained model because the layer on which dropout was applied is forced to learn the same "concept" with different sets of interconnected neurons. Hence, dropout is a technique that can be used to avoid overfitting of a neural network during training. In general, the more learning capacity a model/a neural network has (more layers, or more neurons) the more prone the model/the NN is to overfitting.

Using a dropout technique for computing the model certainty for each tile prediction may have the advantage that many neural network architectures and programs already comprise one or more dropout layers, so existing program libraries and software tools can be used for computing model uncertainty. Furthermore, applicant has observed that neural networks used in the context of digital pathology often face the problem of overfitting, because the neural networks used for performing image analysis and classification tasks often comprise many layers and because the size of the training data set is often limited.

According to embodiments, applying dropout during the training phase means creating many different dropout layers respectively comprising a randomly selected sub-set of nodes of a fully connected layer, whereby each dropout layer acts as a masks (comprising "zero"-nodes and "one"-nodes). The masks are created during forward propagation, are respectively applied to the layer outputs during training and cached for future use on back-propagation. The dropout mask applied on a layer is saved to allow identifying the neurons that were activated during the backward propagation step. Now with those identified neurons selected, the output of the neurons is back-propagated. Typically, the dropout layers are created and used only during the training phase and are saved in the form of deactivated, additional layers in the trained network.

According to some embodiments, the dropout layers are used only during training.

This may have the advantage that the trained MIL-program already learns during the training phase to assess the variability of the predictive values computed for the feature vector of a particular tile using many different network architectures using the dropout masks. Provided the training images are similar to the tissue images used at test time, the model uncertainty/variability of computed tile-based predictive values is inherently encoded in the trained ML program and will accurately reflect uncertainties of the model in respect to various tissue structures depicted in the test images.

Some embodiments of the invention use dropout on the fully connected layers only, but other embodiments in addition use dropout after the max-pooling layers, thereby creating some kind of image noise augmentation.

During the test phase, the dropout layers are typically deactivated in state-of-the-art machine-learning programs. However, according to some embodiments, the dropout technique is used at training and test time of the model. For example, the creation or re-activation and application of dropout layers allows learning (at training time) or predicting (at test time) same concept in many different ways, thereby allowing to assess the model uncertainty and variety of the predictions generated by the model for a given input. According to embodiments, the certainty-value is computed as Monte-Carlo Dropout (MC Dropout).

The key idea behind Monte-Carlo Dropout (MC Dropout) is assessing model uncertainty by using dropout. MC Dropout calculates the model uncertainty (and hence, implicitly, also model certainty) using a dropout technique, i.e. by randomly using different subnetworks of a neural network architecture to get multiple different results from the network for the same predictive task and assess the "certainty" as the "consistency" of the result. MC is referring to Monte Carlo as the dropout process is similar to sampling the neurons.

For example, according to some embodiments of the invention, at test time the same input is provided to the network with random dropout multiple times, e.g. a few hundreds of times, each time using a different dropout mask. Then the mean of all the multiple predictions obtained for each tile is computed and a prediction interval covering all these predictions or another measure of prediction variability/model uncertainty is generated.

Applying dropout at test time may have the disadvantage of lowering overall model accuracy. However, in the context of tissue image analysis, it has been observed that this disadvantage is actually a benefit as this step imposes model uncertainty where it should and can reduce overfitting. For example, when input data are far away from data the model was trained on, the variability of the predictions obtained at test time for the same input tile using many different dropout masks will indicate that the model is unsure how to interpret this type of tile. In the domain of tissue image analysis, a huge variety of healthy as well as disease-induced tissue structures exists. Additional variability is induced by the existence of many different staining protocols, many different stains and the fact that even traits of the individual person who performs the staining protocol may have an impact on the stained tissue slice and hence may have an impact on the digital tissue image. It is therefore very unlikely that the training data set will cover all conceivable variations and combinations of healthy and diseased tissue structures and different staining methods. Using MC dropout will therefore provide a MIL-program that is able to automatically assess at test time and for each of the tiles individually the uncertainty of the model configured to predict the correct class of the image based on the features of this particular tile.

According to some embodiments, the MCdropout Mean-STD (MCdropout Mean-standard deviation), which comprises measuring the variance of the model over many forward pass runs, is used for computing the certainty of the model in respect to a particular classification task and is used for computing the certainty values for each of the tiles. Tiles whose feature vector does not comprise sufficient and/or appropriate information for the model to reliably and accurately determine a bag label will generate lower predictive values during training. An example for computing the MCdropout Mean-STD is described in detail in Yarin Gal et al., "Deep Bayesian Active Learning with Image Data", March 2017, arXiv:1703.02910v1.

According to embodiments, the certainty-value-based pooling function of the MIL-program is configured to compute, for each of the tiles of an image, a predictive value wh weighted with the MCdropout Mean-STD as follows:

For each of the K tiles of an image $I_m$, the certainty value (also referred to as "instance certainty) $c_{k\_m}$ is computed as the inverse of the MC dropout based Mean-STD computed by the model of the MIL-program after a softmax or sigmoid layer at test time. The formula for the certainty $c_{k\_m}$ for every instance (tile) k is given according to $$c_{k\_m} = c_{(x_k)} = \frac{1}{\sigma(x_k) + \varepsilon},$$

wherein $\sigma(x_k)$ is the MC dropout Mean-STD for instance k. $\varepsilon$ is a small number that prevents division by zero.

The certainty values $c_{k\_m}$ of all tiles of an image can be aggregated using max or mean-based certainty-value-based pooling function as described above for embodiments of the invention. If a certainty-value-based-max-pooling function is used, the instance (tile) that has the highest predictive value h generated as output by the model of the MIL-program weighted by its certainty value c is selected. If a certainty-value-based-mean-pooling function is used, the certainty values c of each of the K tiles are passed, according to embodiments of the invention through a softmax function (that can be implemented as a layer of the network) to get averaging weights that sum to 1. Then a weighted average wh of the instance predictions h using the certainty values c as weights are computed. Hence, whk is the output of the prediction network for instance (tile) k.

Embodiments of the invention provide a new certainty-value-based pooling function that aggregates bag instances using a certainty value assigned to the individual instances. The certainty-value-based pooling function can be applied during training but can also be used to improve pretrained MIL-program trained with dropout at test time.

According to embodiments, the certainty-value-based pooling function (which may use a dropout technique for computing model uncertainty) is used at test time but not at training time of the model.

This means that according to embodiments of the invention, the image classification method can be applied "off-the-shelf" on pretrained MIL models to significantly improve their performance although during the training, no certainty-value-based pooling function may have been used. This may have the advantage that even in case a MIL-program was trained without using a certainty-value-based pooling function (with or without a drop-out technique), the image analysis method can be used for classifying images, whereby existing (but originally deactivated for test time use) dropout layers are applied for generating a variety of predictions for a particular image tile at test time, thereby assessing the certainty of the model in respect to the tile-related predictions.

For example, the MIL-program that is trained on a training data set may not comprise any dropout layer at training time and the pooling function used at training time does not take into account model uncertainty. For example, the pooling function used by the MIL-program at training time can be a conventional max pooling or mean pooling function. The computing of the certainty value for any one of the tiles at test time comprises adding one or more dropout layers to the trained MIL program at test time. The added dropout layers can be used at test time to compute a certainty value for each input tile reflecting the uncertainty of the trained model.

According to embodiments, the neural network comprises one or more deactivated dropout layers. A deactivated dropout layer is a dropout layer that was activated at training time and that was deactivated at completion of the training. The computing of the certainty value for any one of the tiles at test time comprises reactivating the one or more dropout layers at test time.

According to embodiments, the computing of the certainty value for any one of the tiles at test time comprises, after having added or reactivated the one or more dropout layers at test time:

- computing, for each of the tiles, multiple times a predictive value ha based on the feature vector extracted from the tile; each time the predictive value ha is computed a different subset of nodes of the network is dropped by the one or more reactivated or added dropout layers; and
- computing, for each of the tiles, the certainty value c of the tile as a function of the variability of the multiple predictive values ha computed for the tile, wherein the larger the variability, the lower the certainty value c.

This may have the advantage that in case existing dropout layers of the network have been deactivated after completion of the training phase or have been used during the training phase on a significantly different data set, or in case the neural network used as the MIL-program does not comprise any dropout layers at test time, the reactivation of existing layers or the adding of dropout layers at test time allows generating a variety of predictions for a particular image tile at test time, thereby assessing the certainty of the model in respect to the tile-related predictions, even in case the network architecture of the trained model does not allow computing this variability at first hand.

For example, the MIL-program may have been trained on digital tissue images which are significantly different from the tissue images used at test time. For example, the training and test time images may have been derived from patients having different types of cancer, or may have been stained with similar but different stains, or may depict the same type of cancer cells but in different tissues. In these cases, the trained model may not be able to provide highly accurate predictions for the tissue images and image tiles analyzed at test time. However, by applying the dropout-technique at test time, the accuracy of the predictive value h generated by the trained model for a feature vector extracted from a tile can be automatically assessed and taken into account for classifying a tissue image provided as input at test time.

According to embodiments, the received digital images comprise digital images of tissue samples whose pixel intensity values correlate with the amount of a non-biomarker specific stain, in particular hematoxylin stain or H&E stain.

For example, each bag of tiles can represent a respective patient whose responsiveness to a particular drug is known. The instances contained in this patient-specific bag are tiles derived from one or more images of respective tissue samples of this particular patient, the tissue samples having been stained with a non-biomarker specific stain such as H&E. All tissue images of this patient, and hence all the tiles derived therefrom, have assigned the label "patient responded to drug D=true". H&E stained tissue images represent the most common form of stained tissue images and this type of staining alone already reveals a lot of data that can be used for predicting the patient-related attribute value, e.g. the sub-type or stage of a particular tumor. Furthermore, many hospitals comprise large data bases of H&E stained tissue images derived from patients which have been treated many years in the past. Typically, the hospitals also have data in respect to whether or not a particular patient responded to a particular treatment or not and/or how fast or how severe the disease developed. Hence, a large corpus of training images is available that can be labeled with the respective outcomes (e.g. treatment by a particular drug successful yes/no, progression free survival longer than one year, progression free survival longer than two years, etc.).

According to embodiments the received digital images comprise digital images of tissue samples whose pixel intensity values correlate with the amount of a biomarker specific stain. The biomarker-specific stain is a stain adapted to selectively stain a biomarker contained in the tissue sample. For example, the biomarker can be a particular protein such as HER-2, p53, CD3, CD8 or the like. The biomarker specific stain can be a brightfield microscope or fluorescence microscope stain coupled to an antibody that selectively binds to the above-mentioned biomarker.

In addition, or alternatively, the received digital images comprise digital images of tissue samples whose pixel intensity values correlate with the amount of a biomarker specific stain, the biomarker-specific stain adapted to selectively stain a biomarker contained in the tissue sample.

For example, each bag of tiles can represent a respective patient whose responsiveness to a particular drug is known. The instances contained in this patient-specific bag are tiles derived from one or more images of respective tissue samples of this particular patient. The one or more tissue samples have been stained with one or more biomarker-specific stains. For example, the tiles can be derived from one, two or three tissue images all depicting adjacent tissue slides of the same patient having been stained with a HER2-specific stain. According to another example, the tiles can be derived from a first tissue image depicting a first tissue sample having been stained with a HER2-specific stain, and from a second tissue image depicting a second tissue sample having been stained with a p53 specific stain, and from a third tissue image depicting a third tissue sample having been stained with a FAP-specific stain. The first, second and third tissue sample are derived from the same patient. For example, they can be adjacent tissue sample slices. Although the three tissue images depict three different biomarkers, all tissue images are derived from the same patient, and hence all the tiles derived therefrom have assigned the label "patient responded to drug D=true". Training the MIL-program on image tiles of digital images whose pixel intensity values correlate with the amount of a biomarker specific stain may have the advantage that identifying the presence and position of one or more specific biomarkers in the tissue may reveal highly specific and prognostic information in respect to particular diseases and sub-forms of diseases. The prognostic information may comprise observed positive and negative correlations of the presence of two or more of the biomarkers. For example, the recommended treatment scheme and prognosis of some diseases such as lung cancer or colon cancer have been observed to strongly depend on the mutational signature and expression profile of the cancer. Sometimes, the expression of a single marker alone does not have predictive power, but a combined expression of multiple biomarkers and/or the absence of a particular further biomarker may have high predictive power in respect to a particular patient-related attribute value.

According to embodiments the received digital images comprise a combination of digital images of tissue samples whose pixel intensity values correlate with the amount of a first biomarker specific stain and of digital images of tissue samples whose pixel intensity values correlate with the amount of a non-biomarker specific stain. A biomarker-specific stain is a stain adapted to selectively stain a biomarker contained in the tissue sample. The MIL-program is trained to classify all digital images depicting the same tissue sample and/or depicting adjacent tissue samples from the same patient into the same class.

This approach may have the advantage that identifying the presence and position of one or more specific biomarkers in the tissue in combination with the information-rich tissue signatures revealed by H&E staining may provide highly specific and prognostic information in respect to particular diseases and sub-forms of diseases. The prognostic information may comprise observed positive and negative correlations of the presence of two or more of the biomarkers and/or of tissue signatures visually revealed by a H&E staining.

According to embodiments, the providing of the MIL-program comprises training the model of the MIL-program. The training comprises:

- providing a set of digital training images of tissue samples, each digital training image having assigned a class label being indicative of one of the at least two classes;
- splitting each training image into training image tiles, each training tile having assigned the same class label as the digital training image from which the training tile was derived;
- for each of the tiles, computing, by the image analysis system, a training feature vector comprising image features extracted selectively from the said tile; and/or
- repeatedly adapting the model of the MIL-program such that an error of a loss function is minimized; the error of the loss function indicates a difference of predicted class labels of the training tiles and the class labels actually assigned to the training tiles; the predicted class labels have been computed by the model based on the feature vector of the training tiles.

According to embodiments, the method further comprises, for each of the received digital images:

- weighting the predictive value h of each of the tiles with the certainty value c computed for this tile, thereby obtaining a weighted predictive value wh;
- identifying, by the MIL-program, the one of the tiles of the image for which the highest weighted predictive value wh was computed;
- for each of the other tiles of the image, computing a relevance indicator by comparing the weighted predictive value wh of the other tile with the highest weighted predictive value, wherein the relevance indicator is a numerical value that negatively correlates with the difference of the compared weighted predictive values;
- computing a relevance heat map for the image as a function of the relevance indicator, the pixel color and/or pixel intensities of the relevance heat map being indicative of a relevance indicator computed for the tiles in the said image; and
- displaying the relevance heat map on a GUI.

This may be advantageous as this may enable a pathologist to identify tiles and tissue structures depicted therein which have the highest predictive value in respect to the membership of an image in a particular class. Thereby, new biomedical knowledge can be generated that has not yet been described in the biomedical literature before. For example, by outputting and highlighting the one out of 1000 image tiles depicting a particular tissue structure that is highly predictive of the image class label “tissue of a cancer patient who will benefit from treatment X” may reveal a correlation or causal relationship between the tissue structure depicted this tile and the particular image class that may not have been discovered and published before. Furthermore, even in case the tissue structure being predictive for a particular image class is as such known, the heat map or any other form of graphically representing the tile having the highest predictive value wh may have the advantage that a pathologist is enabled to identify the one or more tiles comprising the most interesting tissue structures in respect to a particular biomedical question faster and more accurately.

For example, image regions and respective tiles that have a weighted predictive value wh that is highly similar to the weighted predicted value of the highest-scoring tile of an image can be represented in the relevance heat map with a first color (e.g. “red”) or a high intensity value and image regions and respective tiles whose weighted predictive value is dissimilar to the highest wh value of all tiles of this image can be represented in the relevance heat map with a second color that is different from the first color (e.g. “blue”) or a low intensity value.

This may be advantageous, because the GUI automatically computes and presents a relevance heat map that indicates the position and coverage of the tissue regions and respective image tiles having a high predictive power (or “prognostic value”) wh having been weighted with the certainty value c of the model in respect to this tile. The relevance heat map may highlight tissue regions having a high relevance indicator. A tile is typically only a small subregion of the whole-slide image and the heat map and/or a gallery of tiles sorted according to the tiles' wh values may not provide an overview over the whole tissue sample. The overview information regarding the position and coverage of tissue patterns with high predictive relevance may be provided by the relevance heat map that is preferably combined with the original image of the whole slide tissue image in a highly intuitive and smart manner.

Computing and displaying the weighted predictive value based heat map may be advantageous as this heat map is indicative of the predictive power of tiles in respect to the endpoint used for training the MIL. Hence, displaying the relevance heat map to a user enables the user to quickly identify the position and coverage of tiles having a tissue pattern that is predictive for a particular label within a whole slide image.

According to embodiments, the method further comprises displaying the received images on a GUI of a screen. The images are grouped in the GUI into the at least two different classes in accordance with a result of the classification.

According to embodiments, each of the at least two classes is selected from a group comprising:

- a patient being responsive to a particular drug;
- a patient having developed metastases or a particular form of metastases (e.g. micro-metastases);
- a cancer patient showing a particular response to a particular therapy, e.g. a pathologic complete response (pCR);
- a cancer patient tissue showing a particular morphological state or microsatellite status;
- a patient has developed adverse reaction to a particular drug;
- a patient having a particular genetic attribute, e.g. a particular gene signature; and/or
- a patient having a particular RNA expression profile.

These labels may be helpful in diagnosis as well as in finding a suitable drug for treating a disease. However, the above-mentioned labels are only examples. Other patient-related attributes can also be used as labels (i.e., endpoints for training the MIL-program) as described above. The term "patient-related" can also comprise treatment-related, because also the effectiveness of a particular treatment of a disease relates to the patient being treated.

Embodiments of the invention are used for identifying tissue patterns being indicative of a patient-related attribute value. This method may be advantageous because it may combine the advantages of image analysis methods based on explicit biomedical expert knowledge with the advantages of machine learning methods.

According to embodiments, the certainty-value-based pooling function is a certainty-value based max-pooling, mean-pooling or an attention pooling function.

According to embodiments, the method further comprises:

- providing a trained attention-MLL having learned which tile-derived feature vectors are the most relevant for predicting class membership for a tile;
- computing an attention weight (aw) for each of the tiles as a function of the feature vector of the respective tile by the attention-MLL, the attention weight being an indicator of the relevance of this tile's feature value in respect to a membership of this tile to a class;
- multiplying the attention weight (aw) of the tile with the tile's feature vector values for obtaining an attention-based feature vector with attention-weighted feature values for the tile; and using the attention-based feature vector as the feature vector that is input to the MIL-program for computing the predictive value (h), the certainty value (c) and/or the weighted predictive value (wh) of the slide, the predictive value (h), the certainty value (c) and/or the weighted predictive value (wh) thereby being computed as attention-based predictive value, an attention-based certainty value and/or as an attention-based weighted predictive value; or
- multiplying the attention weight (aw) of the tile with the tile's predictive value (h), the certainty value (c) or with the tile's weighted predictive value (wh) computed by the MIL for obtaining an attention-based predictive value, an attention-based certainty value and/or an attention-based weighted predictive value.

For example, the attention weight can be computed as described in MAXIMILIAN ILSE ET AL: "Attention-based Deep Multiple Instance Learning", ARXIV.ORG, CORNELL UNIVERSITY LIBRARY, 201 OLIN LIBRARY CORNELL UNIVERSITY ITHACA, N.Y. 14853, 13 Feb. 2018, XP081235680, describes the application of an attention-based Multiple Instance Learner (MIL) on a histopathology data set, e.g. as described with reference to formula (9).

The combination of an attention weight and a certainty value may be particularly advantageous, because the computation of the attention weight alone may provide poor (inaccurate) classification results when the image data is noisy and/or significantly different from the images used during the training phase. However, the disadvantages and the lack of robustness of the attention-based weights can be compensated by taking into consideration also the certainty values: even in case for a particular vector/tile a high attention weight is obtained, the contribution of this tile/vector will largely be ignored if the certainty value obtained for this tile is low, thereby avoiding false positive classification results.

It should be noted that an "attention weight" and a "certainty value" related to completely different concepts: while a "certainty value" is indicative of the certainty of a predictive model regarding the contribution of the vector/tile on the classification result, the "attention weight" is indicative of the relevance (predictive power) of a feature vector/tile in respect to the classification result. For example, a first feature vector may be derived from a first tile of an image and a second vector may be derived from a second tile of the same image.

For example, the attention-MLL may determine, based on the first feature vector, that the image shows a "tumor tissue", because the first feature vector indicates that the first tile comprises a first pattern which very strongly correlates with/has a high predictive value in respect to the tissue type class "tumor tissue". Hence, the attention-MLL will compute a high attention weight for the first tile, because the identified pattern is strongly predictive for the class "tumor tissue".

In addition, the attention-MLL may determine, based on the second feature vector, that the image shows a "tumor tissue", because the second feature vector indicates that the second tile comprises another pattern which weakly positively correlates with the classification "tumor tissue". This means, that about 60% of all images comprising a tile with this pattern are indeed tumor tissue images while about 40% of those images may comprise a tile with this pattern but may nevertheless show a "healthy" tissue.

In case the certainty is not computed/considered, then the following situation may happen: although the correlation of the first pattern with the "tumor class label" may be strong (all training images with at least one tile with the first pattern were indeed tumor tissue images and none of the "healthy tissue" training images comprised a tile with this first pattern), the certainty value for the classification "tumor tissue" may be low. For example, the overall number of tiles with the first pattern in the training set may be small and hence the "certainty" of any prediction based on this first pattern may be low. So it is possible that the attention-MLL computes a high predictive relevance for a tile in respect to a particular class label while the certainty value computed for this tile is low and vice versa. In respect to the second tile, the attention weight will be low as the second pattern appears to be a poor predictor for the class membership, and the certainty value may be high or low depending on the quality and abundance of examples in the training data set comprising the second pattern.

Taking both the attention weight and the certainty value into account ensures that a pattern in the training data set which may appear to strongly correlate with/be highly predictive of a certain class membership is ignored or at least down-weighted in case the training data basis for this prediction, expressed in the certainty value of the model computed for this prediction/classification is low.

For example, a maximum pooling function may classify an image to be member of a particular class only in case an attention-based predictive value which was weighted by the certainty value exceeds a predefined threshold.

According to an embodiment, the predictive values h and/or weighted predictive values wh calculated for the individual tiles can be output together with a graphic representation of the associated tiles in a gallery. For example, the tiles in the gallery can be sorted in accordance with the numerical value wh computed for each tile. In this case, the position of the tiles in the gallery allows a pathologist or other human user to identify the tissue pattern depicted in the ones of the tiles found to be highly predictive for a particular label. In addition, or alternatively, the numerical value can be displayed in spatial proximity to its respective tile, thereby enabling the user to inspect and comprehend the tissue pattern of the tissue depicted in one or more tiles having a similar numerical value in respect to a particular label.

The gallery can be output based on training images at the end of a training phase and/or can be output based on test images at test time. The image tile gallery generated as the output of the trained MIL-program may reveal tissue signatures which are predictive in respect to a particular patient-related attribute value of a patient. Presenting the numerical value in combination with the image tiles may have the benefit that at least in many cases the predictive tissue pattern (which may also be referred to as "tissue signature") can be identified and verbalized by a pathologist by comparing several tiles in the gallery having a similar numerical value with other tiles having a much higher or much lower numerical value and by comparing the tissue signature depicted in these sub-set of tiles in the report gallery.

In a further aspect, the invention relates to an image analysis system for classifying tissue images. The image analysis system comprises at least one processor and a volatile or non-volatile storage medium. The storage medium comprises digital images respectively depicting a tissue sample of a patient.

The image analysis system further comprises an image splitting module being executable by the at least one processor and being configured to split each of the images into a set of image tiles.

The image analysis system further comprises a feature extraction module being executable by the at least one processor and being configured to compute, for each of the tiles, a feature vector comprising image features extracted selectively from the said tile.

The image analysis system further comprises a Multiple-Instance-Learning (MIL) program. The MIL-program is executable by the at least one processor and is configured to use a model for classifying any input image as a member of one out of at least two different classes based on the feature vectors extracted from all tiles of the said input image. The MIL-program is further configured for:

- for each of the tiles, computing a certainty value, the certainty value being indicative of the certainty of the model regarding the contribution of the tile's feature vector on the classification of the image from which the tile was derived;
- for each of the images:
  - using, by the MIL-program, a certainty-value-based pooling function for aggregating the feature vectors extracted from the image into a global feature vector as a function of the certainty values of the tiles of the image, and computing an aggregated predictive value (referred herein according to embodiments of the invention as "ah") from the global feature vector; or
  - computing, by the MIL program, predictive values from respective ones of the feature vectors of the image and using, by the MIL-program, a certainty-value-based pooling function for aggregating the predictive values of the image into an aggregated predictive value ("ah") as a function of the certainty values of the tiles of the image; and
- classifying each of the images as a member of one out of the at least two different classes based on the aggregated predictive value.

According to embodiments, the system comprises an interface for outputting the classification result. For example, the interface can be a machine-to-machine interface, e.g. an application program interface for sending the classification result to a software application program. In addition, or alternatively, the interface can be or comprise a man-machine-interface, e.g. a screen configured to display a GUI which comprises a graphical representation of the classification result. For example, the MIL-program can be configured to output the classification result to a user via the GUI.

According to embodiments, the GUI enables the user to select whether the heat map, that may also be referred to as "relevance heat map", is computed based on the predictive values h of the tiles or based on the weighted predicted values wh of the tiles. This may allow a user to assess the effect of taking into account model uncertainties.

Feature Extraction Approaches

According to embodiments, the computing of the feature vector for each of the tiles at training time and/or at test time comprises extracting one or more image features from the tile and representing the extracted features in the form of one or more features in the feature vector. Optionally, the computing of the feature vector in addition comprises receiving patient-related data of the patient whose tissue sample is depicted in the tile and representing the patient-related data in the form of one or more features in the feature vector. The patient related data can be, for example, genomic data, RNA sequence data, known diseases of the patient, age, sex, metabolite concentrations in a body fluid, health parameters and current medication.

According to embodiments, the computing of the feature vectors is performed by a trained machine learning logic, in particular by a trained fully convolutional neural network comprising at least one bottleneck-layer.

According to embodiments, the trained machine learning logic to be used for feature extraction ("feature extraction MLL") is trained in a supervised method by taking an MLL of type fully convolutional network that includes a bottleneck, like UNET. The "Unet" architecture is described by Olaf Ronneberger, Philipp Fischer, and Thomas Brox in "U-Net: Convolutional Networks for Biomedical Image Segmentation", Computer Science Department and BIOSS Centre for Biological Signalling Studies, University of Freiburg, Germany (arXiv:1505.04597v1 18 May 2015). The document can be downloaded via the Cornell University Library https://arxiv.org/abs/1505.04597.

For example, the feature extraction MLL can be trained to perform a tissue image segmentation task, whereby the segments to be identified comprise two or more of the following tissue image segment types: tumor tissue, healthy tissue, necrotic tissue, tissue comprising particular objects such as tumor cells, blood vessels, stroma, lymphocytes, etc., and background area. According to some embodiments, the feature extraction MLL is trained in a supervised manner using a classification network such as Resnet, ImageNet, or SegNet, by training it to classify tiles of images with specific predetermined classes or objects.

After the feature extraction MLL has been trained, the MLL is split into an "encoder" part (comprising the input layer, one or more intermediate layers and a bottleneck layer) and a "decoder", i.e., an output-generation part. The "encoder" part up to the bottleneck layer of the trained MLL is used according to embodiments of the invention to extract and compute the feature vector for each input tile. The bottleneck layer is a layer of a neural network that comprises significantly less neurons than the input layer. For example, the bottleneck layer can be a layer comprising less than 60% or even less than 20% of the "neurons" of the input layer. The number and ratio of the neurons in the different layers may vary a lot depending on different network architectures. The bottleneck layer is a hidden layer.

According to one example, the network of the feature-extraction MLL has a UNET based network architecture. It has an input layer of with 512*512*3 (512×512 RGB) neurons and bottleneck layer with 9*9*128 neurons. Hence, the number of neurons in the bottleneck layer is about 1.5% of the number of neurons of the input layer.

According to one example, the network of the feature-extraction MLL has a Resnet architecture that implements supervised or unsupervised learning algorithms. The input layer comprises 512×512×3 neurons and the bottleneck layer and the corresponding feature vector output by the bottleneck layer comprises typically 1024 or 2048 elements (neurons/numbers).

According to embodiments, the feature extraction is performed by a feature extraction program module that is based on the ResNet-50 (He et al., 2016) architecture trained on the ImageNet natural image dataset. Some detailed examples for feature extraction from images that is based on this architecture is described in Pierre Courtiol, Eric W. Tramel, Marc Sanselme, & Gilles Wainrib: "CLASSIFICATION AND DISEASE LOCALIZATION IN HISTOPATHOLOGY USING ONLY GLOBAL LABELS: A WEAKLY-SUPERVISED APPROACH", arXiv:1802.02212, submitted on 1 Feb. 2018, available online via the Cornell University Library https://arxiv.org/pdf/1802.02212.pdf.

According to embodiments, the output generated by one of the layers of the trained feature extraction MLL for a particular tile is used as the feature vector extracted from the tile by the MIL-program. This one layer can be, in particular, the bottleneck layer. According to embodiments, the feature extraction MLL is trained in an unsupervised or self-supervised manner as described in Mathilde Caron and Piotr Bojanowski and Armand Joulin and Matthijs Douze: "Deep Clustering for Unsupervised Learning of Visual Features", CoRR, 1807.05520, 2018 that is electronically available via https://arxiv.org/abs/1807.05520.

Alternatively, the feature extraction MLL can be trained in accordance with Spyros Gidaris, Praveer Singh, Nikos Komodakis: "Unsupervised Representation Learning by Predicting Image Rotations", 15 Feb. 2018, ICLR 2018 Conference electronically available via https://openreview.net/forum?id=S1v4N2l0-.

Still alternatively, the feature extraction MLL can be trained in accordance with Elad Hoffer, Nir Ailon. "Semi-supervised deep learning by metric embedding", 4 Nov. 2016, ICLR 2017 electronically available via https://openreview.net/forum?id=r1R5Z19le.

The dataset for training the feature extraction MLL can be another tissue image dataset and/or the set of tissue images that is later used for training the MIL-program. Any labels associated with the training images are not evaluated or otherwise used by the feature extraction MLL in the training phase as the feature extraction MLL is trained for identifying tissue types and respective image segments rather than the patient-related attribute value of the patient that is used as the end-point of the learning phase of the MIL-program.

Feature Extraction Approaches Making Use of Proximity-Based Similarity Labels

According to embodiments, the feature vectors are computed by a feature extraction machine learning logic ("feature extraction MLL") having been trained on a training data set comprising labeled tile pairs, whereby each label represents the similarity of two tissue patterns depicted by the tile pair and is computed as a function of the spatial distance of two tiles of the tile pair.

According to preferred embodiments, the labels are assigned to the tile pairs in the training data set fully automatically.

This approach may be beneficial for multiple reasons: spatial proximity of two image regions is a feature that is always and inherently available in every digital image of a tissue sample. The problem is that spatial proximity of image and respective tissue regions per se typically do not reveal any relevant information in respect to a biomedical problem such as tissue type classification, disease classification, the prediction of the durability of a particular disease or an image segmentation task. Applicant has surprisingly observed that the information conveyed in the spatial proximity of two image regions ("tiles") is an accurate indicator of the similarity of the two image regions, at least if a large number of tiles and their respective distances is analyzed during the training phase of an MLL. Hence, by making use of the inherently available information "spatial proximity" of two tiles for automatically assigning a tissue pattern similarity label to the two compared tiles, a large annotated data set can be provided automatically that can be used for training a MLL. The trained MLL can be used for automatically determining if two images or image tiles received as input depict a similar or dissimilar tissue pattern. However, the data set can in addition be used for other and more complex tasks such as image similarity search, image segmentation, tissue type detection and tissue pattern clustering. Hence, applicant has surprisingly observed that the information conveyed in the spatial proximity of tiles can be used for automatically creating annotated training data that allows training an MLL that reliably determines the similarity of images and in addition may allow training an MLL that outputs a feature vector that can be used by additional data processing units for a plurality of complex image analysis tasks in digital pathology. None of these approaches requires a domain expert to annotate training data manually.

When a training image comprising many different tissue patterns (e.g. "non-tumor" and "tumor") is split into many different tiles, the smaller the distance between two tiles, the higher the probability that both compared tiles depict the same tissue pattern, e.g. "non-tumor". There will, however, be some tile pairs next to the border of two different patterns that depict different tissue pattern (e.g. the first tile "tumor", the other tile "non-tumor"). These tile pairs generate noise, because they depict different tissue patterns although they lie in close spatial proximity to each other. Applicant has surprisingly observed that this noise that is created by tile pairs spanning the border between different tissue patterns in combination with the simplifying assumption that spatial proximity indicates similarity of depicted tissue patterns does not reduce the accuracy of the trained MLL significantly. In fact, applicant observed that the accuracy of an MLL that was trained according to embodiments of the invention are able to outperform existing benchmark methods.

In a further beneficial aspect, it is now possible to quickly and fully automatically create training data for many different sets of images. Currently, there is a lack of available annotated datasets that capture the natural and practical variability in histopathology images. For example, even existing large datasets like Camelyon consist of only one type of staining (Hematoxylin and Eosin) and one type of cancer (Breast Cancer). Histopathology image texture and object shapes may vary highly in images from different cancer types, different tissue staining types and different tissue types. Additionally, histopathology images contain many different texture and object types with different domain specific meanings (e.g. stroma, tumor infiltrating lymphocytes, blood vessels, fat, healthy tissue, necrosis, etc.). Hence, embodiments of the invention may allow automatically creating an annotated data set for each of a plurality of different cancer types, cancer-sub-types, staining methods and patient groups (e.g. treated/non-treated, male/female, older/younger than a threshold age, biomarker-positive/biomarker-negative, etc.). Hence, embodiments of the invention may allow automatically creating annotated training data and training a respective MLL on the training data such that the resulting trained MLL is adapted to accurately address biomedical problems for each of a plurality of different groups of patients in a highly specific manner. Contrary to state of the art approaches where a MLL trained on a manually annotated breast cancer data set provided suboptimal results for colon cancer patients, embodiments of the invention may allow creating a MLL for each of the different patient groups separately.

According to embodiments, the label being indicative of the degree of similarity of two tissue patterns is a binary data value, i.e., a value that may have one out of two possible options. For example, the label can be "1" or "similar" and indicate that the two tiles depict a similar tissue pattern. Alternatively, the label can be "0" or "dissimilar" and indicate that the two tiles depict dissimilar tissue patterns. According to other embodiments, the label can be more fine grained, e.g. can be a data value selected from a limited set of three or more data values, e.g. "dissimilar", "similar" and "highly similar". According to still other embodiments, the label can be even more fine grained and can be a numerical value, wherein the amount of the numerical value positively correlates with the degree of similarity. For example, the numerical value can be computed as a function that linearly and inversely transforms the spatial distance between the two tiles in the pair into the numerical value representing tissue pattern similarity. The larger the spatial distance, the smaller the numerical value indicating tissue pattern similarity. A large variety of MLL architectures exist which can process and use different types of labels in the training data set (e.g. ordinal or numerical values). The type of MLL is chosen such that it is able to process the automatically created labels of the training data set.

According to embodiments, the MLL that is trained on the automatically annotated training data set and that is to be used for feature extraction is adapted to learn according to a supervised learning algorithm. Supervised learning is about finding a mapping that transforms a set of input features as a member of one or more output data values. The output data values are provided during the training as labels, e.g. as a binary option label "similar" or "non-similar" or as a numerical value that is a quantitative measure for similarity. In other words, during the training, the data values that shall be predicted are explicitly provided to the model of the MLL in the form of the labels of the training data. Supervised learning comes with the problem that the training data needs to be labeled in order to define the output space for each sample.

According to embodiments, at least some or all of the tile pairs respectively depict two tissue regions contained in the same tissue slice. Each of the tissue slices is depicted in a respective one of the received digital images. The distance between tiles is computed within a 2D coordinate system defined by the x- and y-dimension of the received digital image from which the tiles in the pair have been derived. According to embodiments, the tile pairs are generated by randomly selecting tile pairs within each of the plurality of different images. The random based selection ensures that the spatial distance between the tiles in each pair will vary. A similarity label, e.g. in the form of a numerical value that correlates inversely with the distance between the two tiles, is computed and assigned to each pair.

According to other embodiments, the tile pairs are generated by selecting at least some or all of the tiles of each received image as a starting tile; for each starting tile, selecting all or a predefined number of "nearby tiles", wherein a "nearby tile" is a tile within a first circle centered around the starting tile, whereby the radius of this circle is identical to a first spatial proximity threshold; for each starting tile, selecting all or a predefined number of "distant tiles", wherein a "distant tile" is a tile outside of a second circle centered around the starting tile, whereby the radius of the said circle is identical to a second spatial proximity threshold; the selection of the predefined number can be performed by randomly choosing this number of tiles within the respective image area. The first and second proximity threshold may be identical, but preferably, the second proximity threshold is larger than the first proximity threshold. For example, the first proximity threshold can be 1 mm and the second proximity threshold can be 10 mm. Then, a first set of tile pairs is selected, whereby each tile pair comprises the start tile and a nearby tile located within the first circle. Each tile pair in the first set is assigned the label "similar" tissue patterns. In addition, a second set of tile pairs is selected, whereby each pair in the said set comprises the start tile and one of the "distant tiles". Each tile pair in the second set is assigned the label "dissimilar" tissue patterns. For example, this embodiment may be used for creating "binary" labels "similar" or "dissimilar".

According to embodiments, the distance between tiles is measured within the 2D coordinate system defined by the x and y axes of the digital image from which the tiles are derived. These embodiments may be used in a situation where a plurality of tissue sample images are available which depict tissue samples of different patients and/or of different regions within the same patient, whereby said different regions lie far away from each other or whereby the exact position of the said two regions relative to each other is unknown. In this case, the spatial proximity between tiles is measured only within the 2D plane of pixels defined by the digital image. Based on a known resolution factor of the image acquisition device (e.g. a camera of a microscope or a slide scanner), the distance between tiles of the original image can be used for computing the distance between the tissue regions in the tissue sample depicted by the two tiles.

According to embodiments, at least some or all of the tile pairs depict two tissue regions contained in two different tissue slices of a stack of adjacent tissue slices. Each of the tissue slices are depicted in a respective one of the received digital images. The received images depicting tissue slices of a stack of adjacent tissue slices are aligned with each other in a 3D coordinate system. The distance between tiles is computed within the 3D coordinate system.

For example some or all received digital images may depict tissue samples which are slices within a tissue block of adjacent tissue slices. In this case, the digital images can be aligned with each other in a common 3D coordinate system such that the position of the digital image in the 3D coordinate system reproduces the position of the respectively depicted tissue slices within the tissue block. This may allow determining the tile distance in a 3D coordinate system. The selection of "nearby" and "distant" tiles can be performed as described above for the 2D coordinate system case, with the only difference that the tiles in at least some of the tile pairs are derived from different ones of the received images.

According to some embodiments, the annotated training data comprises both tile pairs derived from the same digital image as well as tile pairs derived from different images having been aligned with each other in a common 3D coordinate system. This may be beneficial as the consideration of the third dimension (spatial proximity of tiles representing tissue regions in different tissue samples) may tremendously increase the number of tiles in the training data in case only a small number of images of respective tissue samples is available whereby the tissue samples belong to the same cell block, e.g. a 3D biopsy cell block.

According to embodiments, each tile depicts a tissue or background region having a maximum edge length of less than 0.5 mm, preferably less than 0.3 mm.

A small tile size may have the advantage that the number and area fraction of tiles depicting a mixture of different tissue patterns is reduced. This may help reducing the noise generated by tiles depicting two or more different tissue patterns and by tile pairs next to a "tissue pattern border" depicting two different tissue patterns. In addition, a small tile size may allow generating and labeling a larger number of tile pairs, thereby increasing the amount of labeled training data.

According to embodiments, the automatic generation of the tile pairs comprises: generating a first set of tile pairs using a first spatial proximity threshold; the two tissue regions depicted by the two tiles of each tile pair in the first set are separated from each other by a distance smaller than the first spatial proximity threshold; generating a second set of tile pairs using a second spatial proximity threshold; the two tissue regions depicted by the two tiles of each tile pair in the second set are separated from each other by a distance larger than the second spatial proximity threshold. For example, this can be implemented by selecting a plurality of start tiles, computing a first and a second circle based on the first and second spatial proximity threshold around each start tile and selecting tile pairs comprising the start tile and a "nearby tile" (first set) or a "distant tile (second set) as described already above for embodiments of the invention.

According to embodiments, the first and second spatial proximity thresholds are identical, e.g. 1 mm.

According to preferred embodiments, the second spatial proximity threshold is at least 2 mm larger than the first spatial proximity threshold. This may be advantageous, because in case the tissue pattern changes gradually from one into another pattern, the difference between the tissue pattern depicted in a "distant tile" compared to the tissue pattern depicted in a "nearby" tile may be clearer and the learning effect may be improved.

According to embodiments, the first spatial proximity threshold is a distance smaller than 2 mm, preferably smaller than 1.5 mm, in particular 1.0 mm.

In addition, or alternatively, the second spatial proximity threshold is a distance larger than 4 mm, preferably larger than 8 mm, in particular 10.0 mm.

These distance thresholds refer to the distance of the tissue regions (or slice background regions) depicted in the digital images and respective tiles. Based on a known magnification of the image acquisition device and the resolution of the digital image, this distance can be transformed in a distance within the 2D or 3D coordinate system of a digital image.

For example, the distance between tiles (and the tissue regions depicted therein) can be measured e.g. between the centers of two tiles in a 2d or 3D coordinate system. According to an alternative implementation variant, the distance is measured between the two tile edges (image region edges) lying closest to each other in the 2D or 3D coordinate system.

The above-mentioned thresholds have been observed to provide labeled training data that allows automatically generating a trained MLL that is accurately capable of identifying similar and dissimilar tissue patterns for breast cancer patients. In some other implementation examples, the first and second spatial proximity threshold may have other values. In particular in case a different set of received digital images showing different tissue types or cancer types is used, the first and second spatial proximity threshold may have other values than the above provided distance threshold values.

According to embodiments, the method further comprises creating the training data set for training the feature-extraction-MLL. The method comprises receiving a plurality of digital training images each depicting a tissue sample; splitting each of the received training images into a plurality of tiles ("feature extraction training tiles"); automatically generating tile pairs, each tile pair having assigned a label being indicative of the degree of similarity of two tissue patterns depicted in the two tiles of the pair, wherein the degree of similarity is computed as a function of the spatial proximity of the two tiles in the pair, wherein the distance positively correlates with dissimilarity; training a machine learning logic—MLL—using the labeled tile pairs as training data to generate a trained MLL, the trained MLL having learned to extract a feature vector from a digital tissue image that represent the image in a way that images that are similar have similar feature vectors and images that are dissimilar have dissimilar feature vectors; and using the said trained MLL or a component thereof as a feature extraction MLL that is used for computing the feature vectors of the tiles.

This approach may be beneficial because as the labels of the training data set can be created automatically based on information that is inherently contained in every digital pathology image, it is possible to create an annotated data set for training a feature extraction MLL that is specifically adapted to the currently addressed biomedical problem simply by choosing the training images accordingly. All further steps like the splitting, labeling and machine learning steps can be performed fully automatically or semi-automatically.

According to embodiments, the trained MLL is a Siamese network comprising two neuronal sub-networks joined by their output layer. One of the sub-networks of the trained Siamese network is stored separately on a storage medium and is used as the component of the trained MLL that is used for computing the feature vectors of the tiles.

According to embodiments, the MIL-program learns in the training phase to translate feature vectors to a predictive value h that can represent probability for a particular bag label (i.e., image class membership). The label can represent a class (e.g. patients responding to the treatment with a particular drug D or a numerical range indicating the degree of a response). This learning can be mathematically described as the learning of a non-linear transform function that transforms the feature values into one of the labels provided during training. According to some embodiments, at testing time some minor structural changes are applied to the trained MIL-program (such as disabling Dropout layers, etc.) and no sampling of the test data takes place. The main change when applying the trained MIL-program at test time is that all instances (tiles) in the bags of the test data are analyzed by the MIL-program to compute the final numerical values indicating the predictive power for each of the tiles and for each of a plurality of labels provided in the training phase. Finally, a final numerical value is computed for the whole image or for a particular patient by aggregating the (weighted) predictive values computed for the tiles of the image for the plurality of labels. The final result of applying the trained MIL-program on the one or more images of the patient is the one of the labels having the highest probability (e.g. "patient will respond to a treatment with drug D!"). In addition, the one of the tiles having the highest predictive power in respect to this label may be presented in a report image tile gallery that is structurally equivalent to the report image tile gallery described above for the training phase.

According to embodiments, the method further comprises automatically selecting or enabling a user to select one or more "high-predictive-power-tiles". A high-predictive-power-tile" is a tile whose predictive value or weighted predictive value indicating the predictive power of its feature vector in respect to a particular one of the labels exceeds a high-predictive-power-threshold.

In addition, or alternatively, the method further comprises automatically selecting or enabling a user to select one or more "artifact-tiles". An artifact-tile is a tile whose numerical value indicates the predictive power of its feature vector in respect to a particular one of the labels is below a minimum-predictive-power-threshold or depicts one or more artifacts.

In response to the selection of one or more high-predictive-power-tiles and/or artifact-tiles, automatically re-training the MIL-program, thereby excluding the high-predictive-power-tiles and artifact-tiles from the training set.

These features may have the advantage that the re-trained MIL-program may be more accurate, because the excluded artifact-tiles will not be considered any more during re-training. Hence, any bias in the learned transformation that was caused by tiles in the training data set depicting artifacts is avoided and removed by re-training the MIL-program on a reduced version of the training data set that does not comprise the artifact-tiles.

Enabling a user to remove highly prognostic tiles from the training data set may be counter-intuitive but nevertheless provides important benefits: sometimes, the predictive power of some tissue patterns in respect to some labels is self-evident.

For example, a tissue section comprising many tumor cells expressing a lung-cancer-specific biomarker is of course an important prognostic marker for the presence of the disease lung cancer. However, the pathologist may be more interested in some less obvious tissue patterns, e.g. the presence and/or location of non-tumor cells, e.g. FAP+ cells.

According to embodiments, the predictive value h computed by the MIL-program for a particular tile based on the feature vector of this tile is indicative of the predictive power of the tile in respect to the bag's (image's) label.

According to some embodiments, the weighted predictive value wh of a tile is computed by multiplying the model's certainty value c computed for the tile with the predictive value h of this tile.

According to other embodiments, the method comprises computing, for each of the tiles, the feature vector in the form of a weighted feature vector. The weighted feature vector is computed as a function of the weight computed as the model's certainty value c for said tile and of the feature vector computed for said tile by the feature extraction program. In particular, the certainty value c can be multiplied with the feature vector of this tile.

According to one embodiment, the training of the MIL-program is implemented such that the model's certainty value cs computed for the tiles of a bag are provided together with the feature vectors of the tiles as input of the MIL-program. The training of the MIL is implemented such that the MIL learns more from tiles whose feature vector have a higher certainty value (i.e., "weight") than from tiles whose feature vector have a lower weight. In other words, during the training, the MIL-program learns to correlate the impact of the tiles and their feature vectors on the predictive values of the tiles with the certainty values computed for a particular tile that are used as weights.

A "tissue sample" as used herein is a 2D or 3D assembly of cells that may be analyzed by the methods of the present invention. The cell assembly can be a slice of an ex-vivo cell block. For example, the sample may be prepared from tissues collected from patients, e.g. a liver, lung, kidney or colon tissue sample from a cancer patient. The samples may be whole-tissue or TMA sections on microscope slides. Methods for preparing slide mounted tissue samples are well known in the art and suitable for use in the present invention.

Tissue samples may be stained using any reagent or biomarker label, such as dyes or stains, histochemicals, or immunohistochemicals that directly react with specific biomarkers or with various types of cells or cellular compartments. Not all stains/reagents are compatible. Therefore, the type of stains employed and their sequence of application should be well considered, but can be readily determined by one of skill in the art. Such histochemicals may be chromophores detectable by transmittance microscopy or fluorophores detectable by fluorescence microscopy. In general, cell containing samples may be incubated with a solution comprising at least one histochemical, which will directly react with or bind to chemical groups of the target. Some histochemicals are typically co-incubated with a mordant or metal to allow staining. A cell containing sample may be incubated with a mixture of at least one histochemical that stains a component of interest and another histochemical that acts as a counterstain and binds a region outside the component of interest. Alternatively, mixtures of multiple probes may be used in the staining, and provide a way to identify the positions of specific probes. Procedures for staining cell containing samples are well known in the art.

An "image analysis system" as used herein is a system, e.g. a computer system, adapted to evaluate and process digital images, in particular images of tissue samples, in order to assist a user in evaluating or interpreting, e.g. classifying, an image and/or in order to extract biomedical information that is implicitly or explicitly contained in the image. For example, the computer system can be a standard desktop computer system or a distributed computer system, e.g. a cloud system. Generally, a computerized histopathology image analysis system takes as its input a single- or multi-channel image captured by a camera and attempts to provide additional quantitative information to aid in the diagnosis or treatment. The image can be received directly from the camera or can be read from a local or remote storage medium.

Embodiments of the invention may be used for classifying tissue images, e.g. in order to perform image-based tumor staging and/or to determine which sub-group of patients in a larger group of patients will likely profit from a particular drug. Personalized medicine (PM) is a new medical field whose aim is to provide effective, tailored therapeutic strategies based on the genomic, epigenomic and proteomic profile of an individual. PM does not only try to treat patient, but also to prevent patients from negative side effects of ineffective treatments. Some mutations that often occur when a tumor develops give rise to resistance to certain treatments. Hence, the mutational profile of a patient that may be revealed at least in part by tissue images of biomarker-specifically stained tissue samples will allow a trained MIL-program to clearly decide if a particular treatment will be effective for an individual patient. Currently, it is necessary to determine in a trial and error approach if a prescribed medication is effective in a patient or not. The trial and error process may have many negative side effects such as undesired and complex drug interactions, frequent change of the drugs that are prescribed, long delays until an effective drug is identified, disease progression and others. The image classification performed according to embodiments of the invention can be used for stratifying individuals into subpopulations that vary in their response to a therapeutic agent for their specific disease. For example, some ALK kinase inhibitors are useful drugs for treating about 5% of NSCLC lung cancer patients who have elevated expression in the ALK gene. However, after some time, the kinase inhibitors become ineffective due to mutations of the ALK gene or of other genes downstream of the signaling cascade of ALK. Therefore, intelligent molecular characterization of lung cancer patients allows for the optimal use of some mutation-specific drugs through stratification of patients. Hence, the "group of patients" from whom the training images or the test images are taken can be groups such as "100 breast cancer patients", 100 HER+ breast cancer patient", "200 colon cancer patients" or the like.

A "digital image" as used herein is a numeric representation, normally binary, of a two-dimensional image. Typically, tissue images are raster type images meaning that the image is a raster ("matrix") of pixels respectively having assigned at least one intensity value. Some multi-channel images may have pixels with one intensity value per color channel. The digital image contains a fixed number of rows and columns of pixels. Pixels are the smallest individual element in an image, holding antiquated values that represent the brightness of a given color at any specific point. Typically, the pixels are stored in computer memory as a raster image or raster map, a two-dimensional array of small integers. These values are often transmitted or stored in a compressed form. A digital image can be acquired e.g. by digital cameras, scanners, coordinate-measuring machines, microscopes, slide-scanning devices and others.

A "label" as used herein is a data value, e.g. a string or a numerical value, that represents and specifies a patient-related attribute value and/or a class of patients having this attribute value. Examples for a label can be "patient response to drug D=true", "patient response to drug D=false", "progression free survival time>6 month", "patient has micrometastases", and the like.

An "image tile" or "tile" as used herein is a sub-region of a digital image. In general, the tiles created from a digital image can have any shape, e.g. circular, elliptic, polygonal, rectangle, square or the like and can be overlapping or non-overlapping. According to preferred embodiments, the tiles generated from an image are rectangular, preferably overlapping tiles. Using overlapping tiles may have the advantage that also tissue patterns that would otherwise be fragmented by the tile generation process are represented in a bag. For example, the overlap of two overlapping tiles can cover 20-30%, e.g. 25% of the area of a single tile.

A "pooling function" is a permutation invariant transformation that generates a single, aggregate numerical value for a bag of tiles based on all the tiles. The pooling function may allow specifying how the information encoded in all the tiles of a bag are taken into account during the training and/or test phase for computing an image classification result. The pooling function is used by the MIL-program in the training phase and the same or a different pooling function is used by the trained MIL-program at test phase. According to preferred embodiments, the pooling function used by the MIL-program at training time as well as at test time is a certainty-value-based pooling function. For example, the pooling function used at training time is a certainty-value-based-mean-pooling-function and the pooling function used at test time is a certainty-value-based-max-pooling function.

A "certainty-value-based—pooling function" is a pooling function that explicitly or implicitly takes into account the certainty values computed by the MIL-program for each of the tiles of an image.

A "feature vector" as used herein is a data structure that contains information describing an object's characteristics. The data structure can be a monodimensional or polydimensional data structure where particular types of data values are stored in respective positions within the data structure. For example, the data structure can be a vector, an array, a matrix or the like. The feature vector can be considered as an n-dimensional vector of numerical features that represent some object. In image analysis, features can take many forms. A simple feature representation of an image is the raw intensity value of each pixel. However, more complicated feature representations are also possible. For example, a feature extracted from an image or image tile can also be a SIFT descriptor feature (scale invariant feature transform). These features capture the prevalence of different line orientations. Other features may indicate the contrast, gradient orientation, color composition and other aspects of an image or image tile.

An "embedding" is a translation of a high-dimensional vector into a low-dimensional space. Ideally, an embedding captures some of the semantics of the input by placing semantically similar inputs close together in the embedding space. Within the context of this application, the embeddings are considered to be a type of feature vector, because the embedding is derived by the originally extracted feature vector by means of a mathematical transformation and hence the resulting parameter values in an embedding can also be considered as "feature values" extracted from a particular tile.

A "machine learning logic (MLL)" as used herein is a program logic, e.g. a piece of software like a neuronal network or a support vector machine or the like, that has been trained or that can be trained in a training process and that comprises a predictive model that—as a result of the training phase—has learned to perform some predictive and/or data processing tasks (e.g. image classification) based on the provided training data. Thus, an MLL can be a program code that is at least partially not explicitly specified by a programmer, but that is implicitly learned and modified in a data-driven learning process that builds one or more implicit or explicit models from sample inputs. Machine learning may employ supervised or unsupervised learning.

The expression "Multiple-instance learning" (MIL) as used herein refers to a type of (weakly) supervised machine learning approach. Instead of receiving a set of instances which are individually labeled, the learner receives a set of labeled bags, each containing many instances. In the simple case of multiple instance binary classification, a bag may be labeled negative if all the instances in it are negative. On the other hand, a bag is labeled positive if there is at least one instance in it which is positive. From a collection of labeled bags, the learner tries to either (i) induce a concept that will label individual instances correctly or (ii) learn how to label bags without inducing the concept. A convenient and simple example for MIL is given in Babenko, Boris. "Multiple instance learning: algorithms and applications" (2008). However, MIL-programs according to some embodiments also cover the training based on more than two different labels (end-points).

According to embodiments of the present invention, the MIL-program is used to calculate the predictive value for each instance (tile) of a bag (multiple or preferably all tiles of a digital tissue image) and thus also for the tissue patterns respectively depicted in the tiles. In this step new biomedical knowledge can be identified by the MIL-program, because in the training data the labels of the images and the respective tiles are given as end points for the training, but not the individual features of the feature vectors derived from the tiles which correlate strongly (positively or negatively) with the label and which are therefore predictive for this label.

In other words, MIL refers to a form of (weakly supervised) machine learning in which the training instances belonging to a common entity are provided in sets of instances, the sets being called bags. At training time a label being indicative of a membership of the bag in a particular class ("class label") is provided for the entire bag while the labels of the individual instances are not known. For example, a digital training image whose membership in a class is known may be split into image tiles. The training image has assigned a class label and the tiles generated from the training image may all be implicitly assigned with the class label of the training image but do not have assigned a label indicating whether or not this particular tile comprises any feature whose presence implies that the image from which the tile is derived belongs to the class indicated in the class label. This training data thus represents a weakly annotated data. The aim of the learning is to train a model that has learned to identify features of the instances which are highly predictive of the membership of the corresponding bag in a particular class and hence, that has learned to compute a predictive value h for each tile for correctly assigning a class label to the image (i.e., to the bag of instances) as a function of the class label predictions generated for each of the instances of the bag. In order to generate the class label of the bag from the multiple class label predictions generated by/for all the instances of the bag, a permutation invariant pooling function is applied on the predictions generated for each of the bag instances.

A "MIL-program" is a software program configured to be trained or having been trained in accordance with the above-mentioned MIL approach.

A "certainty value" as used herein is a data value, in particular a numerical value, that is indicative of the certainty of a model of a machine learning program regarding the contribution of the tile's feature vector on the classification of the image from which the tile was derived. For example, if a model predicts that based on a pattern observed in a tile, the image belongs to a particular image class, the certainty value indicates the probability that this prediction is correct. The certainty value is computed, for example, based on a feature vector (including a normalized for of the feature vector referred to as "embedding") extracted from one out of a plurality of tiles of this image. To provide a more concrete exemplary illustration, the predictive model may have learned to classify data points respectively representing a tile by dividing datapoints in a multidimensional data space with a hyperplane. Data points lying far away from the hyperplane may represent classification results with a "high certainty value" while data points/tiles lying very close to the hyperplane may represent classification results with a low certainty value (a minor change in an attribute/feature value of the data point may result in the data point lying on the other side of the hyperplane and hence in another class). According to embodiments of the invention, the certainty value is represented by the parameter "c".

A "predictive value" as used herein is a data value, in particular a numerical data value, indicating the contribution of the tile's feature vector on the classification of the image from which the tile was derived. In particular, the predictive value indicates the contribution of the tile's feature vector on the membership of the image from which the tile was derived within a particular class. For example, the "contribution" can be described as the degree of evidence for the membership of the image within a particular class. When computing the predictive value for a particular tile, the MIL-program preferably takes into account only the feature vector of the tile from which the feature vector was derived and optionally some non-image based features (but not the feature vector of any other tile). According to embodiments of the invention, the predictive value is represented by the parameter "h". A predictive value having been computed for a particular tile and having been weighted e.g. with the certainty value obtained for this tile is represented by the parameter "wh". The predictive value can also be described according to embodiments of the invention as a numerical value being indicative of the degree of evidence a feature vector of a tile provides for the membership of the image from which this tile's feature vector was derived in a particular one of the at least two classes.

A "certainty-value-based pooling function" as used herein is a function configured for aggregating feature vectors or predictive values having been derived from the feature vectors of all tiles of the image into an aggregated predictive value, thereby taking into account the certainty values computed for each of the tiles.

An "aggregated predictive value" as used herein is a data value, e.g. a numerical value, having been obtained by applying an aggregating function and optionally one or more further data processing steps on a plurality of input values. The input values can be, for example, predictive values (h) or feature vectors (fv) or values derived therefrom. The aggregating function can be, for example, a pooling function that is configured to aggregate multiple feature vectors into a global feature vector (also referred to as "aggregated feature vector") or to aggregate multiple predictive values into an aggregated predictive value, whereby the pooling function takes into account certainty values. The one or more further data processing steps can be, for example, the computing of the aggregated predictive value by a trained machine learning model, e.g. a trained model of a MIL-program, from the global feature vector. For example, the aggregated predictive value can be a numerical value indicating the likelihood that a particular image belongs to a particular class.

A "heat map" as used herein is a graphical representation of data where the individual values contained in a matrix are represented as colors and/or intensity values. According to some embodiments, the heat map is opaque and comprises at least some structures of the tissue slide image based on which the heat map is created. According to other embodiments, the heat map is semi-transparent and is displayed as an overlay on top of the tissue image used for creating the heat map. According to some embodiments, the heat map indicates each of a plurality of similarity scores or similarity score ranges via a respective color or pixel intensity.

A "biomarker specific stain" as used herein is a stain that selectively stains a particular biomarker, e.g. a particular protein like HER, or a particular DNA Sequence, but not other biomarkers or tissue components in general.

A "non-biomarker specific stain" as used herein is a stain that has a more generic binding behavior. A non-biomarker specific stain does not selectively stain an individual protein or DNA sequence, but rather stains to a larger group of substances and sub-cellular as well as supra-cellular structures having a particular physical or chemical property. For example, Hematoxylin and eosin respectively are non-biomarker-specific stains. Hematoxylin is a dark blue or violet stain that is basic/positive. It binds to basophilic substances (such as DNA and RNA, which are acidic and negatively charged). DNA/RNA in the nucleus, and RNA in ribosomes in the rough endoplasmic reticulum are both acidic because the phosphate backbones of nucleic acids are negatively charged. These backbones form salts with basic dyes containing positive charges. Therefore, dyes like hematoxylin bind to DNA and RNA and stain them violet. Eosin is a red or pink stain that is acidic and negative. It binds to acidophilic substances such as positively charged amino-acid side chains (e.g. lysine, arginine). Most proteins in the cytoplasm of some cells are basic because they are positively charged due to the arginine and lysine amino-acid residues. These form salts with acid dyes containing negative charges, like eosin. Therefore, eosin binds to these amino acids/proteins and stains them pink. This includes cytoplasmic filaments in muscle cells, intracellular membranes, and extracellular fibers.

The term "intensity information" or "pixel intensity" as used herein is a measure of the amount of electromagnetic radiation ("light") captured on or represented by a pixel of a digital image. The term "intensity information" as used herein may comprise additional, related information, e.g. the intensity of a particular color channel. A machine-learning program, e.g. a MIL-program, may use this information for computationally extracting derivative information such as gradients or textures contained in a digital image, and the derivative information may be implicitly or explicitly extracted from the digital image during training and/or during feature extraction by the trained machine-learning program. For example, the expression "the pixel intensity values of a digital image correlate with the strength of one or more particular stains" can imply that the intensity information, including color information, allows the machine-learning program and may also allow a user to identify regions in tissue sample having been stained with a particular one of said one or more stains. For example, pixels depicting a region of a sample stained with hematoxylin may have high pixel intensities in the blue channel, pixels depicting a region of a sample stained with fastRed may have high pixel intensities in the red channel.

The term "biomarker" as used herein is a molecule that may be measured in a biological sample as an indicator of tissue type, normal or pathogenic processes or a response to a therapeutic intervention. In a particular embodiment, the biomarker is selected from the group consisting of: a protein, a peptide, a nucleic acid, a lipid and a carbohydrate. More particularly, the biomarker may be a particular protein, e.g. EGRF, HER2, p53, CD3, CD8, Ki67 and the like. Certain markers are characteristic of particular cells, while other markers have been identified as being associated with a particular disease or condition.

In order to determine the stage of a particular tumor based on an image analysis of a tissue sample image, it may be necessary to stain the sample with a plurality of biomarker-specific stains. Biomarker-specific staining of tissue samples typically involves the use of primary antibodies which selectively bind to the biomarker of interest. In particular these primary antibodies, but also other components of a staining protocol, may be expensive and thus may preclude the use of available image analysis techniques for cost reasons in many application scenarios, in particular high-throughput screenings. Commonly, tissue samples are stained with a background stain ("counter stain"), e.g. a hematoxylin stain or a combination of hematoxylin and eosin stain ("H&E" stain) in order to reveal the large-scale tissue morphology and the boundaries of cells and nuclei. In addition to the background stain, a plurality of biomarker-specific stains may be applied in dependence on the biomedical question to be answered, e.g. the classification and staging of a tumor, the detection of the amount and relative distribution of certain cell types in a tissue or the like.

A "fully convolutional neural network" as used herein is a neural network composed of convolutional layers without any fully-connected layers or multilayer perceptrons (MLPs) usually found at the end of the network. A fully convolutional net is learning filters in every layer. Even the decision-making layers at the end of the network learn filters. A fully convolutional net tries to learn representations and make decisions based on local spatial input.

According to embodiments, the fully convolutional network is a convolutional network with only layers of the form whose activation functions generate an output data vector $y_{ij}$ at a location (i, j) in a particular layer that satisfies the following properties:

$$y_{ij}=f_{ks}(\{x_{si+\delta i,sj+\delta j}\}_{0\leq\delta i,\delta j\leq k})$$

Wherein $x_{ij}$ is a data vector at location (i; j) in a particular layer, and $y_{ij}$ is the data vector at said location in the following layer, wherein $y_{ij}$ is an output generated by the activation functions of the network, where k is called the kernel size, s is the stride or subsampling factor, and $f_{ks}$ determines the layer type: a matrix multiplication for convolution or average pooling, a spatial max for max pooling, or an elementwise nonlinearity for an activation function, and so on for other types of layers. This functional form is maintained under composition, with kernel size and stride obeying the transformation rule:

$$f_{ks}\circ g_{k's'}=(f\circ g)_{k'+(k-1)s',ss'}.$$

While a general deep net computes a general nonlinear function, a net with only layers of this form computes a nonlinear filter, which is also referred to as a deep filter or fully convolutional network. An FCN naturally operates on an input of any size, and produces an output of corresponding (possibly resampled) spatial dimensions. For a more detailed description of the characteristics of several fully convolutional networks see Jonathan Long, Evan Shelhamer, and Trevor Darrell: "*Fully Convolutional Networks for Semantic Segmentation*", CVPR 2015.

An "attention machine learning logic program" as used herein is an MLL that has been trained to assign weights to particular parameters, whereby the weights indicate the importance and the attention other programs may spend on analyzing those parameters. These weights are also referred to as "attention weights" and are indicative of the predictive power of an embedding or tile (but not the certainty of the classification prediction performed based on the features of this tile). The idea behind attention MLLs is to simulate the ability of the human brain to selectively focus on a subset of the available data that is of particular relevance in the current context. Attention MLLs are used e.g. in the text mining field for selectively assigning weights and computational resources to particular words which are of particular importance for deriving the meaning from a sentence. Not all words are equally important. Some of them characterize a sentence more than others. An attention model generated by training an attention MLL on a training data set may specify that a sentence vector can have more attention on "important" words. According to one embodiment, the trained attention MLL is adapted to compute weights for each feature value in each feature vector examined and for calculating the weighted sum of all feature values in each feature vector. This weighted sum embodies the whole feature vector of the tile.

According to embodiments, the MLL is an attention MLL. An attention MLL is a MLL comprising a neural attention mechanism that is adapted to equip a neural network with the ability to focus on a subset of its inputs (or features): it computes an attention value ag for each input and selects specific inputs based on the attention values. According to embodiments, let $x \in Rd$ be an input vector, $z \in Rk$ a feature vector, $a \in [0,1]k$ an attention vector, $g \in Rk$ an attention glimpse and $f\phi(x)$ an attention network with parameters $\phi$. The attention value is computed as $ag=f\phi(x),=a \odot z$, where $\odot$ is element-wise multiplication, while z is an output of another neural network $f\theta(x)$ with parameters $\theta$. According to embodiments, the attention value is used as soft attention, which multiplies features with a (soft) mask of attention values between zero and one, or hard attention, when those values are constrained to be exactly zero or one, namely $a \in \{0,1\}k$. In the latter case, the hard attention mask is used to directly index the feature vector: $g\sim=z[a]$ (in Matlab notation), which changes its dimensionality and now $g\sim \in Rm$ with $m \leq k$.

BRIEF DESCRIPTION OF THE DRAWINGS

In the following embodiments of the invention are explained in greater detail, by way of example only, making reference to the drawings in which:

FIG. 3 depicts a first table showing comparative test results;

FIG. 4 depicts a second table showing comparative test results;

FIG. 8 depicts a GUI with a similarity search image tile gallery;

FIG. 13 shows "similar" and "dissimilar" tile pairs labeled based on their spatial proximity;

FIG. 1 depicts a flowchart of a method according to an embodiment of the invention. The method can be used for classifying tissue images of a patient. The classification can be performed e.g. for predicting an attribute value of a patient such as, for example, a biomarker status, diagnosis, treatment outcome, microsatellite status (MSS) of a particular cancer such as colorectal cancer or breast cancer, micrometastases in Lymph nodes and Pathologic Complete Response (pCR) in diagnostic biopsies. The prediction is based on a classification of digital images of histology slides using a trained MIL-program that takes into account model uncertainties. In the following description of FIG. 1, reference will also be made to elements of FIGS. 2, 15 and 16.

Figure 1:
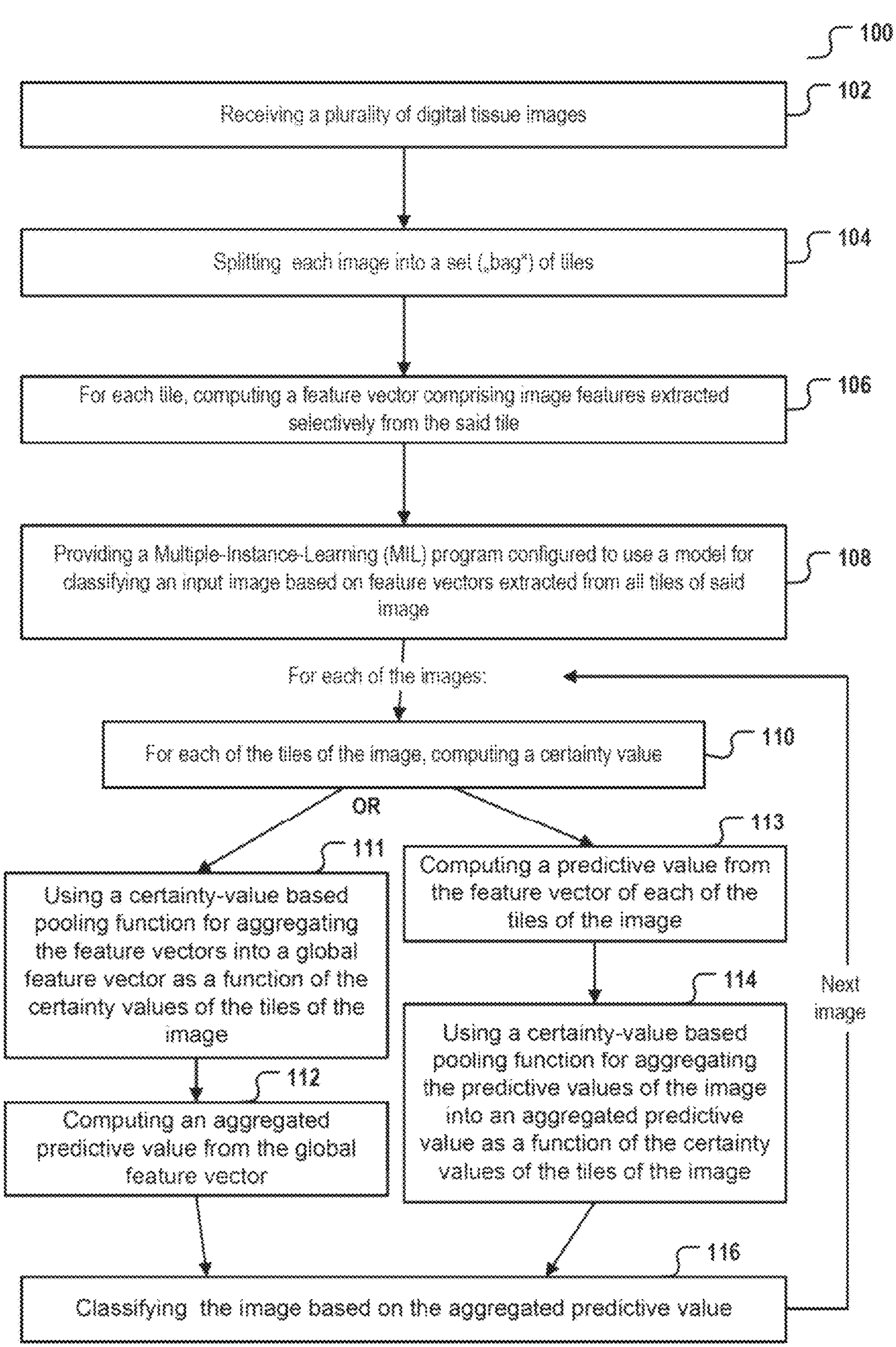
FIG. 1 depicts a flowchart of a method according to an embodiment of the invention.

The method 100 can be used for identifying hitherto unknown predictive histological signatures and/or for classifying tissue samples highly accurately.

In a first step 102, an image analysis system 200 (as described, for example, with reference to FIG. 2) receives a plurality of digital tissue images 212. For example, each tissue image can depict a whole-slide tissue sample taken from a patient, e.g. a cancer patient. For each patient in a group of patients at least one digital tissue image is received. For example, the digital tissue images can be read from a local or remote volatile or non-volatile storage medium 210, e.g. a relational database, or can be received directly from an image acquisition device such as a microscope or a slide scanner. For example, the received images can respectively depict a tissue specimen provided e.g. in the form of FFPET tissue block slice. At test time, the "endpoint" or "class label" of each received image is unknown, meaning that it is not known whether or not the patient from which the tissue sample was derived has a particular disease or disease stage or not or whether this patient will respond to a particular treatment.

Next in step 104, the image analysis system splits each received image into a set of overlapping or non-overlapping image tiles 216. For example, the splitting can be performed by a splitting module 214.

According to one embodiment, the received images as well as the generated tiles are multi-channel images.

Next in step 106, the image analysis system computes, for each of the tiles, a feature vector 220. The feature vector comprises image features extracted selectively from a tissue pattern depicted in the said tile. Optionally, the feature vector can in addition comprise genetic features or other patient or patient-related data that is available for the patient from which the images and respective tiles have been derived. According to some embodiments, the feature extraction is performed by a trained feature extraction module 218. The feature extraction module can be a submodule of the trained MIL-program or can be a separate application program or program module. In particular, the feature extraction module 218 can be a trained MLL. The feature extraction MLL can generate feature vectors for each tile while retaining the feature-vector-tile and feature-vector-image relationship. Other embodiments may use feature extraction modules implemented as conventionally, hand-coded software programs comprising feature extraction algorithms for providing a large variety of features which are descriptive of the tissue area depicted in the tile for which the feature vector is computed. As the features of the feature vectors have been extracted completely or at least partially from the image information contained in the respective tile and do not contain features extracted from any one of the other tiles of the image, the feature vector represents optical properties of the tissue area depicted in this tile. Therefore, a feature vector can be regarded as an electronic tissue signature of the tissue depicted in the tile.

Next in step 108, a Multiple-Instance-Learning (MIL) program 226 is provided. For example, the MIL-program can be an already trained MIL-program that is installed and/or instantiated on an image analysis system 200, e.g. a computer. The trained, instantiated MIL-program then processes the tiles of the received digital tissue images at test time for classifying the received tissue images.

FIG. 1 illustrates the use of an already trained MIL-program for classifying tissue images at test time. In order to generate the trained MIL-program provided in step 108, tissue blocks need to be taken from patients with predetermined and pre-known endpoints (e.g. survival, response, gene signature, etc.) and digital training images of these tissue samples are acquired. The endpoints are used as class labels of each training image to be used for training the MIL-program. For example, the tissue blocks are sliced and the slices set on microscopy slides. Then, the slices are stained with one or more histologically relevant stains, e.g. H&E and/or various biomarker specific stains. Training images are taken from the stained tissue slices using e.g. a slide scanner microscope. The training images can be tissue sample images having been acquired many years ago. Old image datasets may have the advantage that the outcome of many relevant events, e.g. treatment success, disease progression, side effects, etc. are meanwhile known and can be used for creating a training data set comprising tissue images having assigned the known events as labels. In some embodiments, the training image data set can comprise one or more training images per patient. For example, the same tissue sample can be stained multiple times according to different staining protocols, whereby for each staining protocol a training image is acquired. Alternatively, several adjacent tissue sample slices may respectively stained with the same or with different staining protocols and for each of the tissue sample slides a training image is acquired. Each of the received training images has assigned one out of at least two different predefined labels. Each label indicates a patient-related attribute value of the patient whose tissue is depicted in the labeled training image. The attribute value can be of any type, e.g. Boolean, a number, a String, an ordinal parameter value etc. The labels can be assigned to the received training images manually or automatically. For example, a user may configure the software of the slide scanner such that the acquired images are automatically labeled during their acquisition with a particular label. This may be helpful in a scenario where tissue sample images of large groups of patients having the same patient-related attribute value/endpoint are acquired sequentially, e.g. 100 tissue images of a first group of 100 breast cancer patients known to show a response to a particular drug D and 120 tissue images of a second group of 120 breast cancer patients known not to have shown this response. The user may have to set the label that is to be assigned to the captured images only once before the training images of the first group are acquired and then a second time before the training images of the second group are acquired. Then, each training image is split into a plurality of tiles referred herein to as "training tiles". The number of training tiles can be increased for enriching the training data set by creating modified copies of existing training tiles having different sizes, magnification levels, and/or comprising some simulated artifacts and noise. In some cases, multiple bags can be created by sampling the instances in the bag repeatedly as described herein for embodiments of the invention and placing the selected instances in additional bags. This "sampling" may also have the positive effect of enriching the training data set. The MIL-program treats each set of tiles of the same image as a bag of tiles whose bag label needs to be determined. This label determination corresponds to the task to classify the image as the image classes correspond to the labels to be determined.

The vectors extracted from each received digital tissue image at test time are provided as input to the trained MIL-program 226. The feature vectors can be provided in the form of the originally obtained feature vector or in a normalized form that is also referred to as "embedding".

Next in step 110, the MIL-program computes a certainty value 221 for each of the tiles. For example, the model certainty value $c_k$ for a particular tile k can be computed by a) computing a plurality of different predictive values $h_{k1}$, $h_{k2}$, . . . , $h_{kn}$ using n different dropout layers generated by a dropout technique, b) determining the variability of the predictive values $h_{k1}$, $h_{k2}$, . . . , $h_{kn}$, and c) computing the certainty value $c_k$ as a function of this variability, wherein the variability negatively correlates with the certainty value. A large variability of the predictive values $h_{k1}$, $h_{k2}$, . . . , $h_{kn}$ computed based on different dropout network architectures implies that the model of the trained MIL-program is not "sure" about the contribution of the features derived from the tile on the image classification outcome.

In order to compute any of the predictive values h, the MIL-program analyzes the feature vectors 220 of the tiles for computing for each of the tiles a numerical value 228 referred to as predictive value "h". The predictive value "h" indicates the predictive power of the feature vector associated with the tile in respect to a particular class label to be potentially assigned to the image. In other words, this numerical value represents the predictive power, i.e., the "prognostic value/capability", of a particular feature vector for the membership of the image from which the tile was derived in a particular class in view of the tissue pattern depicted in this tile. For example, the trained MIL-program can have learned to predict the contribution of the feature values extracted from a tile on the class membership of the image from which the tile was derived. For example, this "contribution" can be a numerical value that correlates with and/or is indicative of a likelihood that the image belongs to a particular class taking into account the feature vector of the currently analyzed tile.

Two approaches for classifying an image can be followed:

According to one approach, in step 113, for each of the tiles of the image to be classified, a predictive value h, 998 is computed by the MIL-program as a function of the feature vector extracted from this tile. This step 113 may have been executed already as part of step 110. However, in case the certainty value should be computed without using a predictive value h, the step 113 needs to be executed. Next in step 114 a certainty-value-based pooling function 996 is applied on the predictive values 998 such that an aggregated predictive value 997 is computed which integrates not only the predictive values computed for the tiles of the image but also the certainty values 221. This approach via steps 113 and 114 is illustrated e.g. in FIG. 15.

According to an alternative approach, in step 111, the feature vectors extracted from a respective tile of the image are input into a certainty-value-based pooling function 996 that computes a global feature vector 995 from the feature vectors 220, thereby taking into account the certainty values 221 computed for the respective tiles. The global feature vector integrates not only the feature vectors computed for the tiles of the image but also the certainty values 221. Then, the global feature vector is input into the predictive model 999 of the MIL-program for computing in step 112 the aggregated predictive value 887. This approach via steps 111 and 112 is illustrated e.g. in FIG. 15.

Finally in step 116, each of the digital tissue images 212 received at test time is classified in accordance with the aggregated predictive value. For example, if the pooling function is a max-pooling function, the image will be classified to be a member of a particular "positive" class if the maximum weighted predictive value wh obtained from all tiles of this image exceeds a predefined threshold. If not, the image is classified not to be member of this particular class. In a binary class setting, this result implies the image's membership in the other of the two possible classes.

In some cases, an additional, trained attention-MLL 222 having learned which feature vectors are the most relevant for predicting class membership is provided. The relevance of a tile is represented as the "attention weight" aw computed by the attention-MLL. In some cases, the attention weight computed by the attention MLL for each tile is multiplied with each tile's feature vector values. As a result of the multiplication, a feature vector with weighted feature values is obtained for each tile and this feature vector is used as input to the MIL-program for computing the predictive values h, the certainty values c and the weighted predictive values wh. In other embodiments the attention weights aw computed by the attention MLL are multiplied with the predictive value h or the weighted predictive value wh computed by the MIL for the feature vector of each tile. This creates a weighted numerical value pp used as indicator of the predictive power of a particular tile and its feature value in respect to a class membership.

According to embodiments, the trained MIL-program and the image classification results can be used for stratifying patient groups. This means the partitioning of patients by a factor other than the treatment given. Stratification can be performed based on patient-related attributes that are not used as the labels when training the MIL-program. For example, such patient-related attributes can be age, gender, other demographic factors or a particular genetic or physiological trait. The GUI enables a user to select a sub-group of the patients whose tissue images were used for training the MIL-program based on any one of said patient-related attributes not used as label and compute the prediction accuracy of the trained MLL selectively on the subgroup. For example, the sub-group can consist of female patients or of patients older than 60 years. The accuracy obtained selectively for the respective subgroups, e.g. female/male or patients older than/younger than 60 may reveal a particular high or low accuracy of the trained MIL in some subgroups. This may allow confounding variables (variables other than those the researcher is studying), thereby making it easier for the researcher to detect and interpret relationships between variables and to identify patient groups who will benefit the most from a particular drug.

Figure 2:
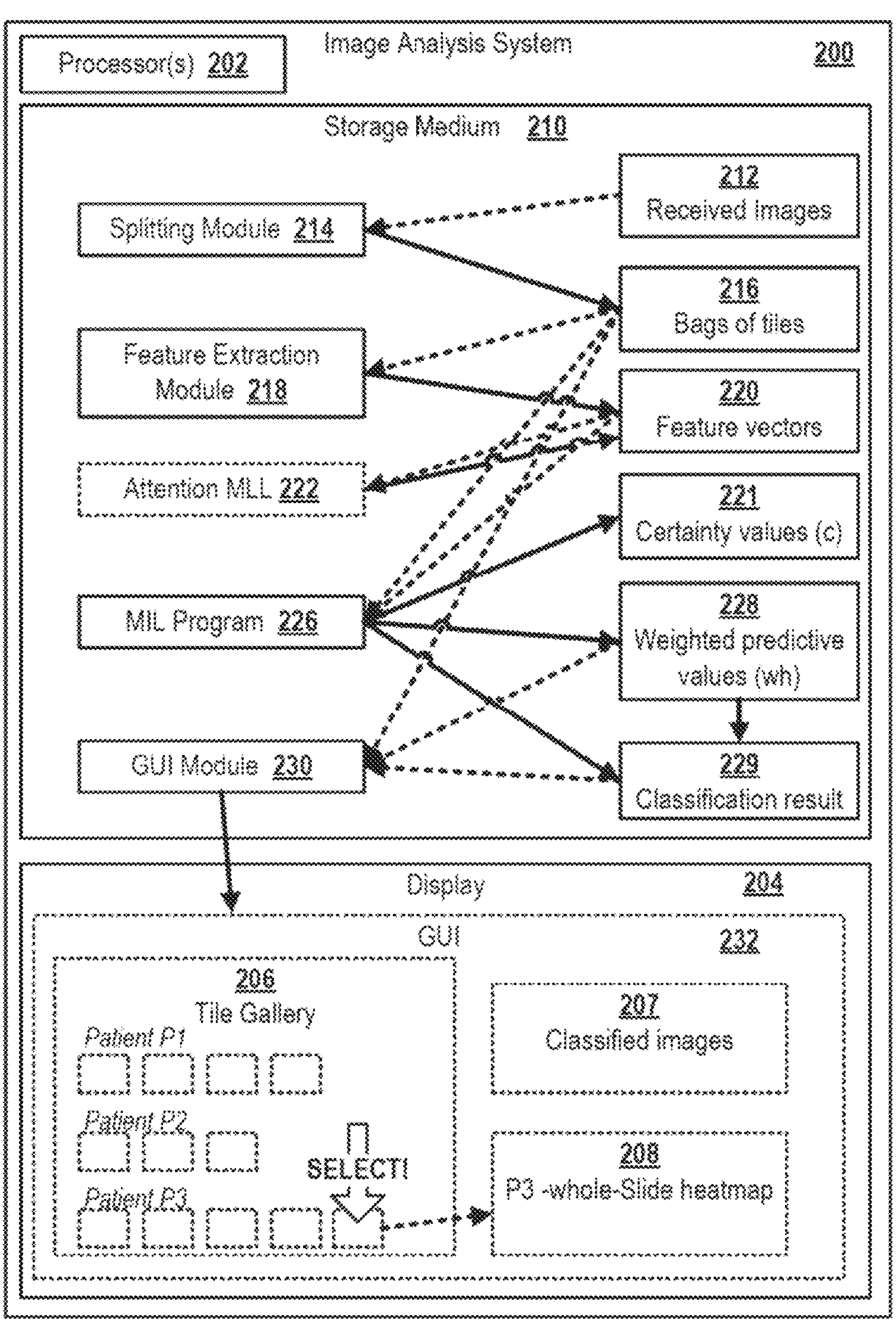
FIG. 2 depicts a block diagram of an image analysis system according to an embodiment of the invention.

FIG. 2 depicts a block diagram of an image analysis system 200 according to an embodiment of the invention.

The image analysis system 200 comprises one or more processors 202 and a volatile or non-volatile storage medium 210. For example, the storage medium can be a hard disk drive, e.g. an electromagnetic or flash drive. It can be a magnetic, semi-conductor based or optic data storage. The storage medium can be a volatile medium, e.g. the main memory, which only temporarily comprises data.

The storage medium comprises a plurality of digital images 212 of tissue samples from patients with unknown endpoints.

The image analysis system comprises a splitting module 214 configured to split each of the images 212 into a plurality of tiles. The tiles are grouped into bags 216, whereby typically all tiles in the same bag are derived from the same patient. The label of the bag represents the membership of the image in one out of two or more different classes and needs to be determined and predicted by the trained MIL-program 226.

A feature extraction module 218 is configured to extract a plurality of image features from each of the tiles 216. In some embodiments, the feature extraction module 218 can be a trained MLL or an encoding part of a trained MLL. The extracted features are stored as feature vectors 220 in association with the tiles from which they are derived in the storage medium 210. Optionally, the feature vectors can be enriched with features of the patient derived from other sources, e.g. genomic data, for example microarray data.

The image analysis system comprises a multiple instance learning program (MIL-program 226). During the training, the MLL program 226 receives the feature vectors 220 (or weighted feature vectors generated by taking into account model uncertainty and optionally in addition taking into account attention scores output by an attention MLL 222) as well as the labels assigned to the respective training tiles. As a result of the training, a trained MIL-program 226 is provided. The trained MIL-program has learned to compute, for each of the tiles, a weighted predictive value wh that is indicative of the predictive power of the tile and the tissue pattern depicted therein for the class label of the image from which the tile is derived, whereby the weight represents the model certainty (and hence, implicitly, also the model uncertainty) in respect to a class membership prediction computed based on the feature vector of a particular tile. These weighted predictive values of the tiles of an image may also be referred to as "numerical tile relevance scores".

The image analysis system further comprises a module 230 configured to generate a GUI 232 that is displayed on a screen 204 of the image analysis system.

The GUI is configured to display the classification result 207 generated by the MIL-program for each of the one or more received images 212. For example, the GUI can display images or image tiles with a class label output by the MIL-program.

Optionally, the GUI comprises a tile gallery 206 comprising at least some of the tiles and the numerical values 228 computed for these tiles. The numerical values 228 can be displayed explicitly, e.g. as an overlay over the respective tile, and/or implicitly, e.g. in the form of a sort order of tiles being sorted in accordance with their respective numerical value 228. When a user selects one of the tiles, a whole slide heat map of the image from which the tile was originally derived is displayed. In other embodiments, the heat map is displayed in addition to the tile gallery 206 per default.

Each of the program modules 214, 215, 218, 222, 226, 230 can be implemented as sub-module of a large MIL-application program or a MIL-training framework software application. Alternatively, one or more of the modules may respectively be implemented as standalone software application programs that are interoperable with the other programs and modules of the image analysis system. Each module and program can be, for example, a piece of software written in Java, Python, C #, or any other suitable programming language.

Optionally, the image analysis system can comprise a sampling module (not shown) adapted to select samples (subsets) of the images for training and test the trained MIL on the rest of the image tiles. The sampling module may perform a clustering of the tiles based on their feature vectors first before performing the sampling.

Optionally, the image analysis system can comprise an attention MLL program 222 that is configured to compute weights for each of the feature vectors and respective tiles in addition to the model-certainty based weights. The weights computed by the attention MLL program can be used, together with the feature vectors, as input to the MIL-program 226 in the training phase and/or for weighting the predictive values h or the weighted predictive values wh computed at test time for each of the tiles by the MIL-program.

FIGS. 3 and 4 depict tables respectively showing comparative test results for using a MIL-based image classifier whose pooling function takes into account the model uncertainty in respect to the model output computed for each image tile. Embodiments of the invention use a certainty-based-pooling function, e.g. a max-pooling function or a mean-pooling function, in order to classify tissue images. Tests were performed on several datasets, including a large challenging real life dataset (Camelyon16) depicted in FIG. 3. The two tests showed that embodiments of the invention and in particular the use of a certainty-based pooling function improved the prediction accuracy on most tasks. On the Camelyon16 dataset, embodiments of the invention also significantly improved the instance level prediction accuracy AUC.

The results further show that the test time prediction of difference methods can be significantly improved in most cases by taking into account also certainty values at training and/or test time. Being able to improve the test-time prediction of existing models is a desirable property. Training MIL methods on large datasets as in requires expensive infrastructure. Test time improvements for existing models avoid the need to re-train them. Using a certainty-value-based-max-pooling function improves the accuracy of the MIL-program at test time.

FIG. 3 depicts a first table 300 showing comparative test results obtained on the data set used as basis for the Camelyon-16 lymph node metastases detection challenge. The aim of this experiment is to compare a MIL-program using a certainty-value-based pooling function to other MIL-programs on a challenging real life dataset. The data set is available under https://camelyon16.grand-challenge.org/data/. Camelyon16 consists of 400 Hematoxylin and Eosin (H&E) stained whole slide images (WSIs) taken from sentinel lymph nodes, which are either healthy or exhibit metastases of some form. In addition to the WSIs themselves, as well as their labeling (healthy, contains-metastases), a pixel level segmentation mask is provided for each WSI. The segmentation mask was discarded and only the global slide level labels were used to create a benchmark for MIL-programs. A simple stain normalization step was applied on the training images by normalizing the mean and std of the LAB color space channels to be the same as in a reference image from the Camelyon16 training set. More advanced normalizations could further improve results. A large set of 256×256 non overlapping training tiles in 20× resolution (which is the working magnification used by clinical pathologists to review slides) was generated from the training images. The set of training tiles was reduced by automatically identifying and discarding background (white) tiles. Automated background detection of white tiles is described e.g. in Pierre Courtiol, et al.: "Classification and Disease Localization in Histopathology Using Only Global Labels: A Weakly-Supervised Approach", 1 Feb. 2018, arXiv:1802.02212. The training tiles were grouped into bags of training tiles, where every bag corresponds to a slide/slide image in the training dataset. A step called stain normalization was applied to normalize tissue staining in different slides and respective training images.

A MIL-program in the form of a Resnet50 (Kaiming He, Xiangyu Zhang, Shaoqing Ren, and Jian Sun. Deep residual learning for image recognition. In Proc. IEEE Conf. on Computer Vision and Pattern Recognition, pp. 770-778, June 2016) pre-trained on ImageNet was provided, and feature vectors (embeddings) of size 2048 were extracted for each tile from the second to last layer of the network.

The prediction network that was used as the MIL-program consists of 5 fully connected layers, with 1024 neurons in the hidden layers, with 30% dropout and ReLU activations. Where an attention network was applied, 4 fully connected layers with 1024, 512 and 256 neurons in the hidden layers was used, whereby the network was trained with ReLU, Batch Normalization and 30% dropout. In all cases, an Adam optimizer was used with default parameters. 128 random instances from every bag were selected during training. It was observed that this sampling strategy largely improved results and prevented quick over-fitting. For every method a model that performed best on a held out validation set (20% of the training set) was selected, and the selected model was tested on the Camelyon-16 test set. During testing, no instance sampling was performed and the full bag was analyzed. In addition, the ability of the classifier to correctly classify tumor vs. non-tumor tiles was quantified by measuring the instance level classifier prediction accuracy, using the expert pathologist tumor annotations from the Camelyon16 dataset. In addition, different pooling functions were applied at test time for all the tested methods to evaluate and compare the performance of MIL-programs using a certainty-value-based pooling functions method against MIL-programs using other pooling strategies when applied on a pretrained model during inference. The accuracy of the results measured as "area under the curve—AUC" are shown in Table 1 depicted in FIG. 3. The certainty-value-based pooling function is referred to as "uncertainty (mean or max) pooling" and provides instance level predictions having the highest accuracy of all MIL-programs compared.

FIG. 4 depicts a second table 400 showing comparative test results obtained on the Colon Cancer dataset (Sirinukunwattana, et al.: "Locality sensitive deep learning for detection and classification of nuclei in routine colon cancer histology images", IEEE Transactions on Medical Imaging, 35 (5):1196-1206, 2016). This dataset comprises 100 H&E images. The data set was used as a training data set for a MIL-program where every bag corresponds to a training image and contains 27×27 tiles extracted from the training image. Bags that contain malignant regions are given the label 1, and 0 otherwise. The same network and learning configuration as in (Maximilian Ilse, Jakub M. Tomczak, Max Welling: "Attention-based Deep Multiple Instance Learning", 28 Jun. 2018 (v4), ICML 2018 paper, arXiv:1802.04712) was used, with the exception that the learning was not restricted to 100 epochs. The training dataset was split into 30%/70% used for train and test. 20% of the training set is held aside as a validation set, and the model was chosen based on the highest validation score. Results are shown in Table 400. A MIL comprising a certainty-value-based-mean-pooling function achieved the highest accuracy both at instance as well as at bag level.

In a further test (not shown), the usability of a MIL-program comprising a certainty-value-based pooling function for key instance retrieval was evaluated based on a synthetically generated training and test set. In this test, 100 bags were created, where every bag has 1,000 instances made out of 224×224 image tiles. 100 instances are set to be plain red images, in all bags. In half of the bags, 100 instances are set to be blue, and their labels are set to 1. The rest of the tiles in each bag are set to be random images from the Camelyon-16 dataset. The images are transformed into 2048 embeddings using Resnet50 pre-trained on ImageNet. The attention network proposed in Yarin Gal et al., "Deep Bayesian Active Learning with Image Data", March 2017, arXiv:1703.02910v1 was used to assign an attention value to every tile. Key instances were retrieved from the bags based on these scores, since these affect the contribution of every tile to the output. First, the attention network proposed was trained for 500 epochs on 80% of the bags, and tested on the remaining 20% with an AUC of 100%. The instances were ranked using the attention scores and the certainty scores, from high to low. It was observed that for the attention network, the red instances common to all bags surprisingly receive the highest attention. The red images are not key instances, since they do not trigger any label. The blue images surprisingly received the lowest attention. Hence, in this example, the use of an attention score was observed to provide sub-optimal results. Contrarily, the certainty value based scores ranked the blue images at the top, and the red images at the bottom. This synthetic problem represents real life problems. In histology datasets, non-informative images that contain mainly background or dirt may compose a significant portion of the dataset despite preprocessing efforts, and appear in bags of all classes. Training the attention network on datasets like this and retrieving images by their attention score, may result in non-informative images retrieved. This undesired effect was indeed observed by the applicant in real-life digital pathology tissue images. On the other hand, since the red images appear in all bags and receive gradients from both labels during training, we would expect the model to be uncertain about their label, and indeed they have the highest uncertainty. Similarly, the blue images are associated with only a single label, causing the network to be very certain about them.

Figure 5:
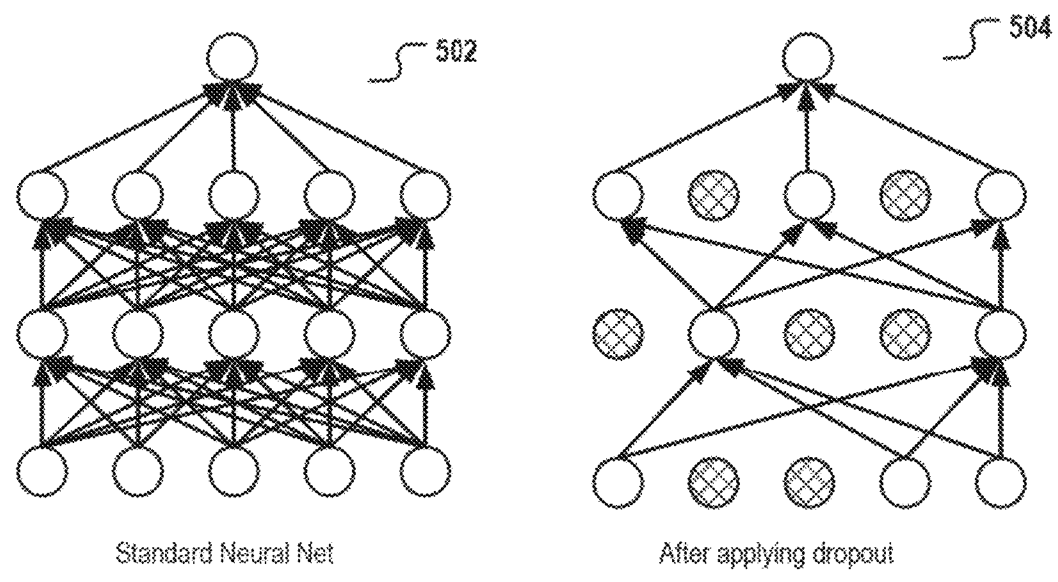
FIG. 5 depicts the effect of applying dropout on a network layer architecture.

FIG. 5 depicts the effect of applying dropout on a network layer architecture. The network architecture 502 depicts the neurons and their connections of three fully connected layers of a neural network. The network 504 shows the same network after applying dropout layers (masks) on one or more of the layers, thereby deactivating a randomly selected sub-set of the nodes of each layer as depicted in the network architecture 504 wherein the nodes with the hatching are deactivated nodes.

Applying dropout layers during training is a technique that seek to reduce overfitting (reduce generalization error) by keeping network weights small (regularization method). More specifically, regularization refers to a class of approaches that add additional information to transform an ill-posed problem into a more stable well-posed problem. Applying dropout layers means probabilistically removing some nodes and respective inputs in one or more network layers during training A common problem in machine learning is that a model with too little capacity cannot learn the problem, whereas a model with too much capacity can learn it too well and overfit the training dataset. In both scenarios, the model will not generalize well. One approach to reducing overfitting when training neural networks is changing network complexity. The capacity of a neural network model, it's complexity, is defined by both it's structure in terms of nodes and layers and the parameters in terms of its weights. Therefore, the complexity of a neural network can be reduced to reduce overfitting by changing the network structure (number of weights) and/or by changing the network parameters (values of weights). For example, the structure could be tuned by applying multiple different dropout layers on a fully connected layer of a neural network until a suitable number of nodes and/or layers is found to reduce or remove overfitting for the problem.

Figure 6:
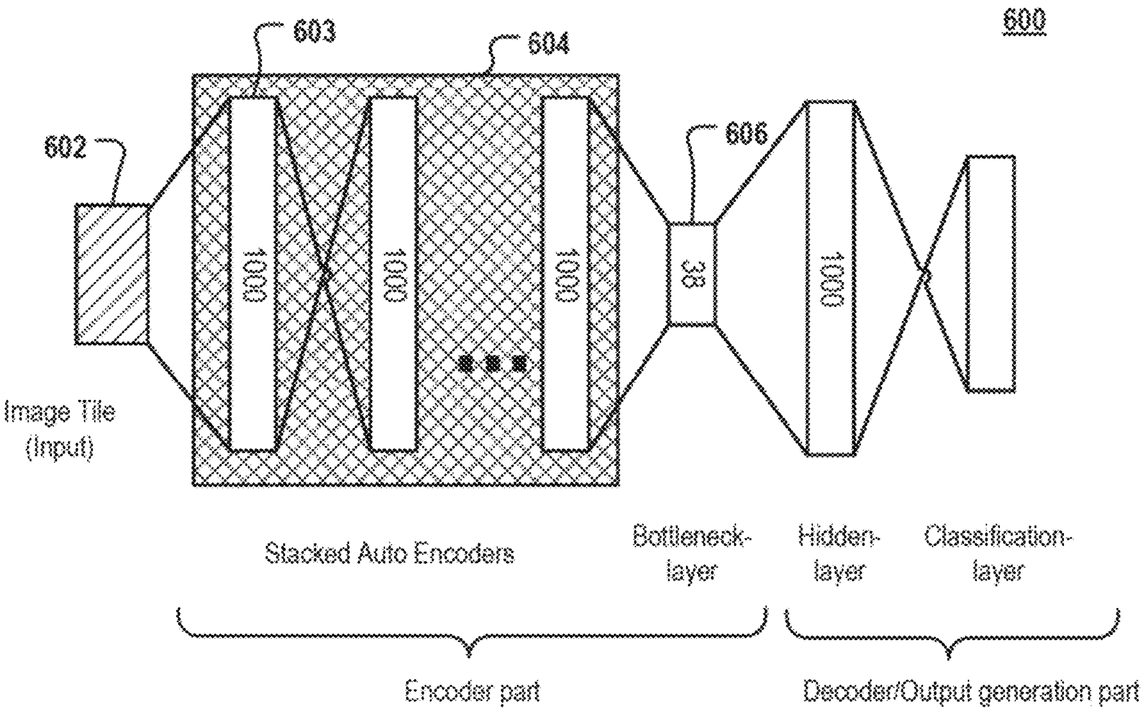
FIG. 6 depicts a network architecture of a feature extraction MLL program according to an embodiment of the invention.

FIG. 6 depicts a network architecture 600 of a feature extraction MLL program according to an embodiment of the invention that supports a supervised learning approach for feature vector generation. A deep neural network consisting of a series 604 of auto-encoders is trained on a plurality of features extracted from image tiles in a layer-wise manner. The trained network is able to perform a classification task later, e.g. to classify the tissue depicted in a tile as a member of one of the classes "stroma tissue", "background slide region", "tumor cells", "metastatic tissue" based on optical features extracted from the image tiles. The network architecture comprises a bottleneck layer 606 that has significantly a less neurons than the input layer 603 and that may be followed by a further hidden layer and a classification layer. According to one example, the bottleneck layer comprises about 1.5% of the number of neurons of the input layer. Potentially there are many hundred or even many thousand hidden layers between the input layer and the bottleneck layer, and features extracted by the bottleneck layer may be referred to as "deep bottleneck features" (DBNF).

Figure 7:
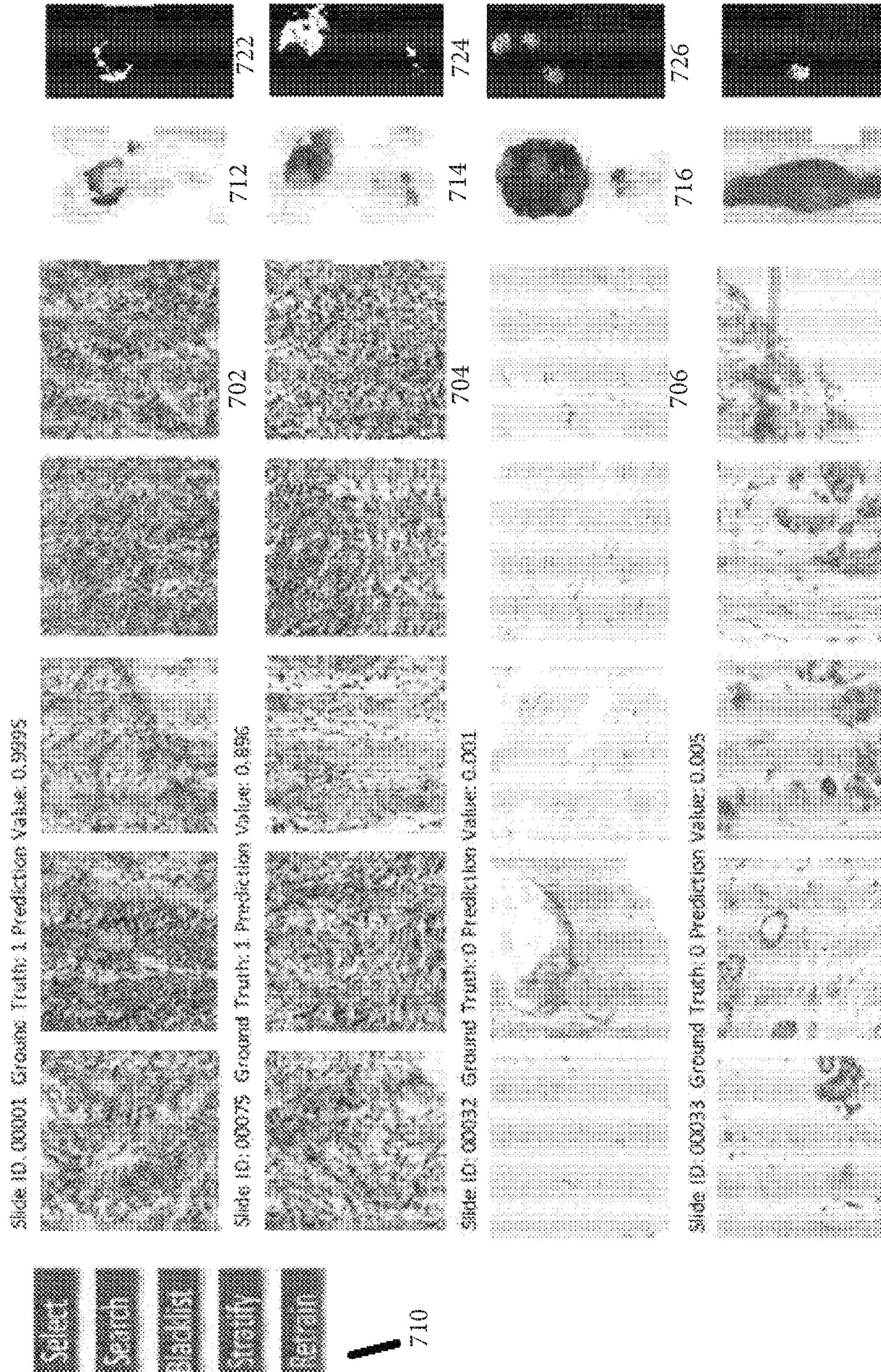
FIG. 7 depicts a GUI with an image tile gallery.

FIG. 7 depicts a GUI 700 with an image tile gallery also referred to as "report tile gallery". The report gallery (matrix of tiles below row labels 702, 704, 706 and 708) allows a user to explore tissue patterns identified by the MIL-program to be of high predictive power in respect to a particular label. The gallery comprises the ones of the tiles having the highest numerical value in respect to a particular label (or "class") of interest, e.g. "response to treatment with drug D=true" computed by the MIL-program. The tiles are grouped based on the tissue slide image (and respective patient) they are derived from and are sorted within their group in accordance with their respective predictive value computed in respect to the class label.

In the example depicted in FIG. 7, a MIL-program using an attention MLL for weighting the predictive values was used for computing weights, but the gallery would look similar if the tiles would have been sorted in accordance with the weighted predictive scores taking into account model uncertainty. Hence, according to embodiments of the invention, the GUI 700 comprises a report tile gallery whose tiles are selected and sorted in accordance with their respectively computed weighted predictive values wh, wherein the weighs correspond to the certainty values c. The tile galleries depicted in FIGS. 7 and 8 are for illustration only as the sorting order of the tiles is similar for a sorting order based on predictive values or weighted predictive values. Nevertheless, applicant has observed that the accuracy of the classification and the accuracy of identifying the most relevant/predictive tiles for a particular class is best when a MIL-program is used that comprises a certainty-value-based pooling function.

The report gallery depicted in FIG. 7 may comprise for each of the tiles in the gallery, the overall predictive accuracy that may have been automatically determined after the training. In addition, or alternatively, the report gallery can comprise the label assigned to the respective image and the predictive accuracy per bag obtained for this label. For example, the "ground truth=0" could represent the label "patient responded to drug D" and the "ground truth=1" could represent the label "patient did not respond to drug D". The highest numerical value of all tiles of a particular image computed by the MIL is displayed as the "predictive value" h or "weighted predictive value" wh on top of the group of tiles derived from said image.

In the depicted gallery, tile row 702 shows six tiles of a first patient. The first one of said tile has assigned the highest predictive value (prognostic value) indicating the predictive power of a particular tissue slide/whole slide image in respect to a label. The first tile per slide-group may in addition or alternatively have assigned the highest combined value (derived from the numerical value provided by the MIL and from the weight computed by the attention MLL) of all tiles derived from a particular tissue slide image.

The highest predictive value can be displayed on top of the highest scoring tiles per patient as depicted in the GUI shown in FIG. 7.

A report tile gallery comprising only a subset of the tiles having the highest predictive value or the highest weighted predictive value may be advantageous as a pathologist does not need to inspect the whole slide. Rather, the attention of the pathologist is automatically directed to a small number of sub-regions (tiles) of each whole-slide image whose tissue pattern has been identified to have the highest predictive power in respect to a label of interest.

According to the embodiment depicted in FIG. 7, the report image tile gallery shows image tiles derived from H&E stained images. The report image tile gallery is organized as follows:

Row 702 comprises the six tiles having assigned the highest numerical value (indicating the predictive power, i.e., the prognostic value) computed by an attention-based MIL-program within all tiles derived from a particular whole slide image 712 of a first patient. According to other embodiments, the sorting is performed based on a score value that is identical to the predictive value computed by the MIL or that is a derivative value of the numerical value, e.g. a weighted predictive value wh, computed by the MIL.

The respective whole slide image 712 of the tissue sample of the first patient that was used for generating the tiles some of which being presented in row 712 is shown in spatial proximity to this selected set 712 of highly relevant tiles.

In addition, an optional relevance heat map 722 is shown that highlights all whole slide image regions whose weighted predictive value computed by the MIL is similar to the numerical value of the one of the tiles of the image 712 for which the highest numerical value indicating the predictive power was computed. In this case, the one of the tiles for which the highest numerical value was computed is identified and selected automatically (e.g. the tile at the first position in row 712) and used as the basis for computing the relevance heat map 722. According to alternative implementation, the relevance heat map 722 represents not the similarity of a tile's numerical value to the highest numerical value computed for all the tiles of the image but rather represents the similarity of a tile to the highest combined score computed for all tiles of the image. The combined score can be a combination, e.g. a multiplication, of a weight computed by an attention MLL for a tile and of the numerical value indicating the predictive power of the tile in respect to the label of the image that is computed by the MIL. According to still further embodiments, the relevance heat map 722 represents the similarity of a tile's weight computed by the attention MLL to the highest weight computed for all the tiles of the image by the attention MLL.

Column 704 comprises the six tiles having assigned the highest numerical value computed by the MIL-program within all tiles derived from a particular whole slide image 714 of a second patient. The respective whole slide image 714 is shown in spatial proximity to this selected set of highly relevant tiles. In addition, a relevance heat map 724 is shown that highlights all whole slide image regions whose respective numerical values computed by the MIL are highly similar to the one of the tile of the whole slide image 714 for which the highest numerical value was computed by the MIL.

Column 706 comprises the six tiles having assigned the highest numerical value computed by the MIL-program within all tiles derived from a particular whole slide image 716 of a third patient. The respective whole slide image 716 is shown in spatial proximity to this selected set of highly relevant tiles. In addition, a relevance heat map 726 is shown that highlights all whole slide image regions whose respective numerical values computed by the MIL are highly similar to the one of the tile of the whole slide image 716 for which the highest numerical value was computed by the MIL.

Column 708 comprises the six tiles having assigned the highest numerical value computed by the MIL-program within all tiles derived from a particular whole slide image 718 of a patient. The respective whole slide image 718 is shown in spatial proximity to this selected set of highly relevant tiles. In addition, a relevance heat map 728 is shown that highlights all whole slide image regions whose respective numerical values computed by the MIL are highly similar to the one of the tile of the whole slide image 718 for which the highest numerical value was computed by the MIL.

According to embodiments, the relevance heat maps presented in the report tile gallery are indicative of the predictive power, or the attention-based weight, and/or of a certainty-based weight, or of a combination thereof. In the depicted example, bright pixels in the heat maps depict areas in the image where tiles have a high predictive value, a high certainty-value-based weight or combination thereof. According to embodiments, the computing of a relevance heat map comprises determining if the score of a tile (e.g. the numerical value, the weight or the combined value) is above a minimum percentage value of the score of the highest scoring tile of an image. If so, the respective tile in the relevance heat map is represented by a first color or a "bright" intensity value, e.g. "255". If not, the respective tile in the relevance heat map is represented by a second color or a "dark" intensity value, e.g. "0".

Each tile in the report tile gallery can be selected by a user for initiating a similarity search (for example by double clicking on the tile or by selecting the tile with a single click and then selecting GUI element "Search") which will then display a similarity search tile gallery as shown, for example in FIG. 8.

The "blacklist" and "retrain" elements in the set of selectable GUI elements 710 enable a user to define a blacklist of tiles and to re-train the MIL-program based on all tiles except the tiles in the blacklist and tiles highly similar to the tiles in the blacklist. For example, the blacklist can comprise set of manually selected tiles having a particularly low numerical value (prognostic value), e.g. because they comprise artifacts, or having a particularly high numerical value (the exclusion of tiles with very high predictive power may increase the capability of the MIL to identify additional, hitherto unknown tissue patterns also having predictive power in respect to the label of interest). The image analysis system can be configured to automatically identify, in response to a user adding a particular tile to the black list, all tiles whose feature vector based similarity to the feature vector of the tile added to the blacklist exceeds a minimum similarity threshold. The identified tiles are automatically added to the blacklist as well. When the user selects the Retrain-GUI element, the MIL is retrained on all tiles of the training data set except the tiles in the blacklist.

FIG. 8 depicts a GUI 800 with a similarity search image tile gallery according to an embodiment of the invention. The similarity search is triggered by a user-based selection of one 830 of the tiles in the report gallery 700.

The search identifies, within the tiles generated from each of the whole slide images 812-818, a sub-set of e.g. six most similar tiles based on a similarity of compared feature vectors. The tiles identified in the similarity search are grouped per-whole-slide image or per-patient and are sorted in descending order in accordance with their similarity to the tile 830 ("query tile") whose selection triggered the similarity search.

The whole slide images 812-818 and the similarity heat maps 822-828 indicate locations of tiles whose feature vectors (and hence, depicted tissue patterns) are the most similar to the feature vector of the selected tile.

Optionally, the similarity search tile gallery in addition comprises one or more the following data:

- the label assigned to the image the depicted tiles were derived from; one label depicted in FIG. 8 is "ground truth: 0";
- a predictive accuracy computed by the MIL-program per bag (image) in respect to the bag's label;
- a count of similar tiles in a whole-slide image and/or the percentage (fraction) of the similar tiles in comparison to the non-similar ones (e.g. by thresholding)
- the average, median or histogram of similarity values of all tiles in a whole-slide-image.

For example, the user may select the one of the tiles 830 of the report gallery having assigned the highest predictive value (e.g. the highest h or wh) and hence the highest predictive power in respect to a label/class membership of the image. By selecting the tile, the user may initiate a tile-based similarity search across the tiles and images of many different patients which may have assigned a different label than the currently selected tile. The similarity search is based on a comparison of the feature vectors and the tiles for determining similar tiles and similar tissue patterns based on similar feature vectors. By evaluating and displaying the number and/or fraction of tiles (and respective tissue patterns) which are similar to the selected tile (and its tissue pattern) but have a different label than the label of the selected tile (e.g. "patient responded to drug D=false" rather than "patient responded to drug D=true").

Hence, the pathologist can easily check the predictive power, in particular sensitivity and specificity, of the tissue pattern identified by the MIL-program by selecting a tile that is returned by the MIL-program as "highly prognostic" for performing a similarity search that reveals how many of the tiles in the data set which have a similar feature vector have assigned the same label as the selected tile. This is a great advantage over state-of-the-art machine learning applications which may also provide an indication of prognostic features of a tissue image but we do not allow a user to identify and verify those features. Based on the report gallery and the similarity search gallery, a human user can verify the proposed highly prognostic tissue patterns and can also verbalize common features and structures that are shown in all tiles having high predictive power and that are associated with similar feature vectors.

The feature that the tiles in the report gallery are selectable and a selection triggers the performing of a similarity search for identifying and displaying other tiles having a similar feature vector/tissue pattern as the user-selected tile may enable a user to freely select any image tile in the report tile gallery he or she is interested in. For example, the pathologist can be interested in the tissue pattern and respective tiles having the highest predictive power (the highest numerical value computed by the MIL) as mentioned above. Alternatively, the pathologist can be interested in artifacts which typically have a particular low predictive power (a particular low numerical value). Still alternatively, the pathologist can be interested in a particular tissue pattern for any other reason, e.g. because it reveals some side effect of a drug or any other biomedical information of relevance. The pathologist is free to select any one of the tiles in the respective report tile gallery. Thereby, the pathologist triggers the similarity search and the computation and display of the results in the form of a similarity tile gallery. The display and the GUI can be refreshed automatically after the similarity search has completed.

According to some embodiments, the computation and display of the similarity search gallery comprises the computation and display of a similarity heat map 822-828. The heat map encodes similar tiles and respective feature vectors in colors and/or in pixel intensities. Image regions and tiles having similar feature vectors are represented in the heat map with similar colors and/or high or low pixel intensities. Hence, a user can quickly get an overview of the distribution of particular tissue pattern signatures in a whole slide image. The heat map can easily be refreshed simply by selecting a different tile, because the selection automatically induces a re-computation of the feature vector similarities based on the feature vector of the newly selected tile.

According to embodiments, the similarity search gallery comprises a similarity heat map. The method comprises creating the similarity heat map by a sub-method comprising:

- Selecting one of the tiles in the report tile gallery;
- For each of the other tiles of some or all of the received images, computing a similarity score in respect to the selected tile by comparing the feature vector of the other tiles of the same and from other images with the feature vector of the selected tile;
- Computing, for each of the images whose tiles were used for computing a respective similarity score, a respective similarity heat map as a function of the similarity scores, the pixel color and/or pixel intensities of the similarity heat map being indicative of the similarity of the tiles in the said image to the selected tile; and
- displaying the similarity heat map.

According to embodiments, also the image tiles shown in the similarity search gallery are selectable.

The similarity heat maps may provide valuable overview information that allows a human user to easily perceive how widespread a particular tissue pattern of interest occurs in a particular tissue or in the tissue samples of a sub-group of patients having a particular label. A user can freely select any of the tiles in the search gallery, thereby respectively inducing a re-computation of the similarity heat map based on the feature vector assigned to the currently selected tile, and an automatic refresh of the GUI comprising the similarity heat map.

According to embodiments, the image tiles in the report gallery and/or in the similarity search tile gallery are grouped based on the patients from whose tissue sample images the tiles were derived. According to alternative embodiments, the image tiles in the report gallery and/or in the similarity search tile gallery are grouped based on the label assigned to the image from which the tiles were derived.

Typically, all images derived from the same patients will have the same label and all tiles derived from those images of a particular patient will be treated by the MIL as members of the same "bag". However, in some exceptional cases, it may be that different images of the same patient have assigned different labels. For example, if the first image depicts a first metastase of a patient and a second image depicts a second metastase of the same patient and the observation is that the first metastase disappeared in response to the treatment with drug D while the second metastase continued to grow, the patient-related attribute value can be assigned image-wise instead of patient wise. In this case, there may be multiple bags of tiles per patient.

According to another example, images of tissue samples of a patient are taken before and after treatment with a particular drug and the end-point (label) used for training the MIL-program and/or for applying a trained MIL-program is the attribute value "state of tissue=after treatment with drug D" or the attribute value "state of tissue=before treatment with drug D". Training a MIL-program on the said patient-related attribute value may have the advantage of identifying tissue patterns which are indicative of the activity and morphological effects of the drug on the tumor.

Such identified drug-effect related tissue patterns could allow verifying and exploring the drug's mode of action as well as potentially drug adverse effects.

According to embodiments, the method further comprises: Computationally increasing the number of bags of tiles by creating additional sets of tiles, each additional set of tiles being treated by the MIL-program as an additional bag of tiles having assigned the same label as the tissue image from which the source tiles were generated. The creation of additional sets of tiles in particular comprises: applying one or more artifact generation algorithms on at least a subset of the tiles for creating new tiles comprising the artifact. In addition, or alternatively, the creation of additional bags of tiles can comprise increasing or decreasing the resolution of at least a subset of the tiles for creating new tiles being more fine-grained or more coarse-grained than their respective source tiles.

For example, a sub-set can be obtained for each of the patients by randomly selecting some or all tiles of the one or more tissue images obtained from said patient. The artifact generation algorithm simulates image artifacts. The image artifacts can be, for example, of the type of artifacts generated during tissue preparation, staining and/or image acquisition (e.g. edge artifacts, overstaining, understaining, dust, speckle artifact, (simulated by Gaussian blur, etc.). In addition, or alternatively, the artifact can be of a generic noise type (simulated e.g. by occlusion, color jittering, Gaussian noise, salt & pepper, rotations, flips, skew distortions etc.).

The creation of additional bags of tiles may have the advantage that additional training data is generated from a limited set of available training data. The additional training data represents image data whose quality may be reduced by common distortions, artifacts and noise that often occur in the context of sample preparation and image acquisition. Hence, the enlarged training data set may ensure that overfitting of the model underlying the MIL-program during training is avoided.

According to embodiments, the method further comprises computing clusters of tiles obtained from the one or more received digital images, wherein tiles are grouped into clusters based on the similarity of their feature vectors. Preferably, the clusters are computed for each of the patients. This means that tiles from different images depicting different tissue slides of the same patient may be grouped into the same cluster if the feature vectors of the tiles are sufficiently similar.

According to other embodiments, the clusters are computed for all the tiles from all the patients together.

In both methods for clustering (all tiles of different patients together or per patient) tiles that look similar to each other (i.e., have similar feature vectors) are clustered into the same cluster.

For example, in case of the "all tiles of different patients clustering", a result of the clustering could be the generation of e.g. 64 groups (clusters) of tiles for all tiles for all the patients. Each of the 64 clusters comprises similar tiles derived from different patients. To the contrary, in the case of a per patient clustering, each patient would have his own 64 clusters.

If clusters are created per patient, it could be that a patient image has no tiles containing fat or very few tiles containing fat. In this case a "fat cluster" might not be created since there is not enough data for learning a cluster around that "fat"-characteristic feature vector. But performing a clustering method on all the tiles of all patients together may have the advantage that a larger number of clusters/tissue types may be identified with the maximum amount of data available: In a "all-patient-tile" clustering, a cluster for the "fat" tissue pattern will likely be identified, because at least some patients will have some fat cells in their biopsy. Hence, the probability that the number of fat cell depicting tiles in the data set is sufficient, a cluster for fat cell would be created (also for the patients with very little fat cell content) If clusters are created for all tiles of all patients together and one cluster represents fat cells, all tiles with fat cells from all of the patients would be grouped in that cluster. This means that for a specific patient/bag all tiles with fat cells would be grouped together in the said cluster and if cluster sampling is used for that bag, some amount of tiles (from the current patient/bag) that belong to said cluster will be selected.

The clustering of tiles may be advantageous as this operation may reveal the number and/or type of tissue patterns observable in a particular patient. According to some embodiments, the GUI comprises a user-selectable element that enables a user to trigger the clustering of tiles and the presentation of the tile clusters in a clustered gallery view. This may assist a user in intuitively and quickly understanding important types of tissue patterns observed in a particular tissue sample of a patient.

According to embodiments, the training of the MIL-program comprises repeatedly sampling the sets of tiles for picking sub-sets of tiles from the sets of tiles, and training the MIL-program on the sub-sets of tiles.

The term "sampling" as used herein is a technique used in the context of data analysis or of training a machine learning algorithm that comprises picking a specifically chosen number of L samples (here: instances, i.e., tiles) out of a number of N data items (instances, tiles) in a dataset (the totality of tiles obtained from one or more images of a patient). According to embodiments, the 'sampling' comprises selecting a subset of data items from within the number of N data items in accordance with a probability distribution assumed to statistically represent the totality of N tiles in the trainings data set. This may allow learning the characteristics of the whole population more accurately. The probability distribution represents a statistical assumption that guides the machine learning process and makes 'learning from data' feasible.

According to some embodiments, the sampling is performed by randomly selecting subsets of tiles for providing sampled bags of tiles.

According to embodiments, the clustering and the sampling are combined as follows: the sampling comprises selecting tiles from each of the tile clusters obtained for a patient such that the number of tiles in each sub-set of tiles created in the sampling corresponds to the size of the cluster from which the said tile is taken.

For example, 1000 tiles may be created from a digital tissue image of a particular patient. The clustering creates a first cluster showing background tissue slide regions that comprises 300 tiles, a second cluster showing stroma tissue regions that comprises 400 tiles, a third cluster showing metastatic tumor tissue comprising 200 tiles, a fourth cluster showing a particular staining artifact comprising 40 tiles and a fifth cluster showing tissue with microvessels comprising 60 tiles.

According to one embodiment, the sampling comprises selecting from each of the clusters a particular fraction of tiles, e.g. 50%. This would mean 150 tiles from cluster 1, 200 tiles from cluster 2, 100 tiles from cluster 3, 20 tiles from cluster 4 and 30 tiles from cluster 5.

According to preferred embodiments, the sampling comprises selecting an equal number of tiles from each cluster. This sampling approach may have the advantage that the same number of tiles/tissue pattern examples from different types of clusters is drawn, thereby making the training data set more balanced. This may increase the accuracy of the trained MIL and/or of the trained attention-MLL in case the desired predictive feature is rare in the training data set.

The combination of clustering and sampling may be particularly advantageous, because the data basis for training can be increased by the sampling without unintentionally "loosing" the few tiles actually being of high predictive power. Often in the context of digital pathology, the vast majority of the area of a tissue sample does not comprise tissue regions that are modified by and that are prognostic for a particular disease or other patient-related attribute. For example, only a small sub-region of a tissue sample may actually comprise tumor cells, the rest may show normal tissue. By performing a clustering of the tiles first and then selecting tiles from each of the clusters may ensure that at least some of the few tiles showing prognostic tissue patterns, e.g. tumor cells or microvessels, are ensured to be always part of the sample.

Figure 9A:
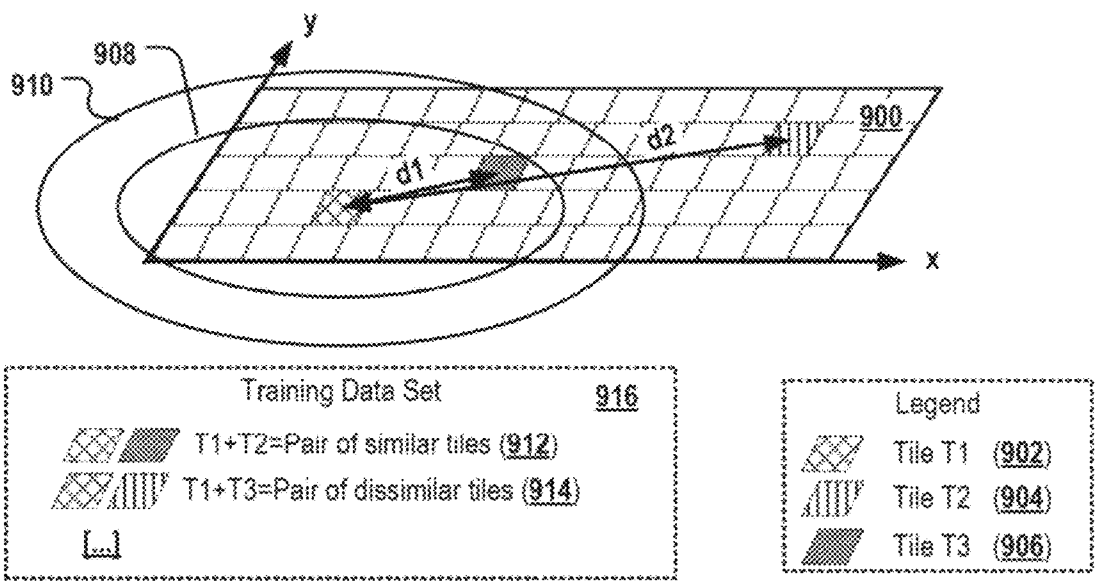
FIG. 9A-9B illustrates spatial distances of tiles in a 2D and a 3D coordinate system.
Figure 9B:
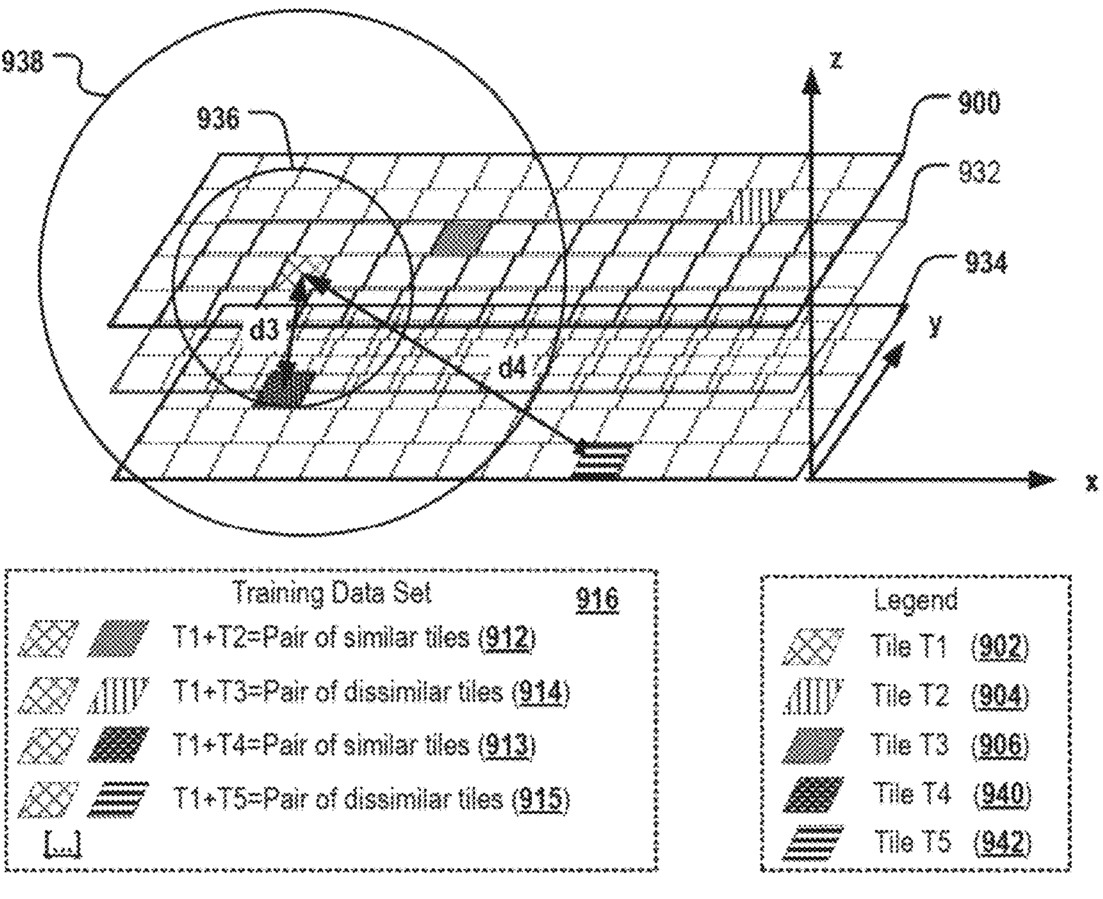

FIGS. 9A and 9B illustrate spatial distances of tiles in a 2D and a 3D coordinate system that are used for automatically assigning similarity labels to pairs of tiles based on similarity labels automatically derived from the spatial proximity of tiles. Thereby, a training data set for training a feature-extraction MLL is provided that does not require manual annotation of images or tiles by a domain expert.

FIG. 9A illustrates spatial distances of tiles in a 2D coordinate system defined by the x and y axes of a digital tissue sample training image 900. The training image 900 depicts a tissue sample of a patient. After the tissue sample has been obtained from the patient, the sample was set on a microscopy slide and was stained with one or more histologically relevant stains, e.g. H&E and/or various biomarker specific stains. The training image 900 has been taken from the stained tissue sample using e.g. a slide scanner microscope. According to some implementation variants, at least some of the received training images are derived from different patients and/or derived from different tissue regions (biopsies) of the same patient and can therefore not be aligned to each other in a 3D coordinate system. In this case, the tile distance can be computed within a 2D space defined by the x and y coordinate of an image as described below.

The training image 900 is split into a plurality of tiles. For illustration purposes, the size of the tiles in FIG. 9A is larger than the typical tile size.

A training data set can be labelled automatically by the following approach: at first, a start tile 902 is selected. Then, a first circular area around this start tile is determined. The radius of the first circle is also referred to as first spatial proximity threshold 908. All tiles within this first circle, e.g. tile 906, are considered to be a "nearby" tile of the start tile 902. In addition, a second circular area around this start tile is determined. The radius of the second circle is also referred to as second spatial proximity threshold 910. All tiles outside of this second circle, e.g. tile 904, are "distant" tiles in respect to the start tile 902.

Then, a first set of tile pairs is created, wherein each tile pair of the first set comprises the start tile and a "nearby" tile of the start tile. For example this step can comprise creating as many tile pairs as nearby tiles are contained in the first circus. Alternatively, this step can comprise randomly selecting a subset of available nearby tiles and creating a tile pair for each of the selected nearby tiles by adding the start tile to the selected nearby tile.

A second set of tile pairs is created. Each tile pair of the second set comprises the start tile and a "distant" tile in respect to the start tile. For example, this step can comprise creating as many tile pairs as distant tiles are contained in the image 800 outside of the second circle. Alternatively, this step can comprise randomly selecting a subset of the available distant tiles and creating a tile pair for each of the selected distant tiles by adding the start tile to the selected distant tile.

Then, another tile within image 900 can be used as starting tile and the above mentioned steps can be performed analogously. This means that the first and second circles are redrawn using the new start tile as the center. Thereby, nearby tiles and distant tiles in respect to the new start tile are identified. The first set of tiles is supplemented with pairs of nearby tiles identified based on the new start tile and the second set of tiles is supplemented with pairs of distant tiles identified based on the new start tile.

Then, still another tile within image 900 can be selected as a start tile and the above mentioned steps can be repeated, thereby further supplementing the first and second tile pair sets with further tile pairs. The selection of new start tiles can be performed until all tiles in the image have once been selected as start tile or until a predefined number of tiles has been selected as start tile.

To each of the tile pairs in the first set, e.g. pair 912, the label "similar" is assigned. To each of the tile pairs in the second set, e.g. pair 914, the label "dissimilar" is assigned.

FIG. 9B illustrates spatial distances of tiles in a 3D coordinate system defined by the x and y axes of a digital tissue sample image 900 and a z axis corresponding to the height of a stack of images 900, 932, 934 aligned to each other in accordance with the relative position of a tissue block's tissue slices respectively depicted by the training images 900, 932, 934. The training images respectively depict a tissue sample derived from a single tissue block of a particular patient. The depicted tissue samples belong to a stack of multiple adjacent tissue slices. For example, this stack of tissue slices can be prepared ex-vivo from a FFPET tissue block. The tissue blocks are sliced and the slices set on microscopy slides. Then, the slices are stained as described for image 900 with reference to FIG. 8A.

As the tissue samples within this stack are derived from a single tissue block, it is possible to align the digital images 900, 932, 934 within a common 3D coordinate system, whereby the z-axis is orthogonal to the tissue slices. The z-axis is an axis orthogonal to the tissue slices. The distance of the images in z direction corresponds to the distance of the tissue slices depicted by the said images. The tile distance of a tile pair is computed within a 2D space in case the two tiles of a pair are derived from the same image. In addition, tile pairs can be created whose tiles are derived from different images aligned to each other in a common 3D coordinate system. In this case, the distance of the two tiles in a pair is computed using the 3D coordinate system.

Each of the aligned digital images is split into a plurality of tiles. For illustration purposes, the size of the tiles in FIG. 9B is larger than the typical tile size.

A training data set can be labelled automatically by the following approach: at first, a start tile 902 is selected. Then, tile pairs comprising the start tile and a nearby tile and tile pairs comprising the start tile and a distant tile are identified and labeled as described below.

A first 3D sphere around this start tile is determined. For illustration purposes, only a cross-section of the first sphere is shown. The radius of the first sphere is also referred to as first spatial proximity threshold 936. All tiles within this first sphere, e.g. tile 906 in image 900, but also tile 940 in image 934, are considered to be a "nearby" tile of the start tile 902. In addition, a second sphere around this start tile is determined. The radius of the second sphere is also referred to as second spatial proximity threshold 938. All tiles outside of this second sphere, e.g. tile 904 of image 900, but also tile 942 of image 934, are "distant" tiles in respect to the start tile 902.

A first set of tile pairs is created, wherein each tile pair of the first set comprises the start tile and a "nearby" tile of the start tile. For example this step can comprise creating as many tile pairs as nearby tiles are contained in the first sphere. Alternatively, this step can comprise randomly selecting a subset of available nearby tiles and creating a tile pair for each of the selected nearby tiles by adding the start tile to the selected nearby tile.

A second set of tile pairs is created. Each tile pair of the second set comprises the start tile and a "distant" tile in respect to the start tile. For example, this step can comprise creating as many tile pairs as distant tiles are contained in the images 900, 932, 934 outside of the second sphere. Alternatively, this step can comprise randomly selecting a subset of the available distant tiles and creating a tile pair for each of the selected distant tiles by adding the start tile to the selected distant tile.

Then, another tile within image 900 or within image 932, 934 can be used as starting tile and the above mentioned steps can be performed analogously. This means that the first and second spheres are redrawn using the new start tile as the center. Thereby, nearby tiles and distant tiles in respect to the new start tile are identified. The first set of tiles is supplemented with pairs of nearby tiles identified based on the new start tile and the second set of tiles is supplemented with pairs of distant tiles identified based on the new start tile.

The above mentioned steps can be repeated until every tile in each of the received images 900, 932, 934 has been selected as start tile (or until another termination criterium is fulfilled), thereby further supplementing the first and second tile pair sets with further tile pairs.

To each of the tile pairs in the first set, e.g. pair 912 and 913, the label "similar" is assigned. To each of the tile pairs in the second set, e.g. pair 914 and 915, the label "dissimilar" is assigned.

The circle and sphere-based distance computation illustrated in FIGS. 9A and 9B are only examples for computing distance-based similarity labels, in this case binary labels being either "similar" or dissimilar". Other approaches can likely be used, e.g. computing the Euclidian distance between two tiles in a 2D or 3D coordinate system and computing a numerical similarity value that negatively correlates with the Euclidean distance of the two tiles.

As the number of pixels that correspond to one mm tissue depends on various factors such as magnification of the image capturing device and the resolution of the digital image, all distance thresholds will herein be specified with respect to the depicted real physical object, i.e., a tissue sample or a slide covered by a tissue sample.

Figure 10:
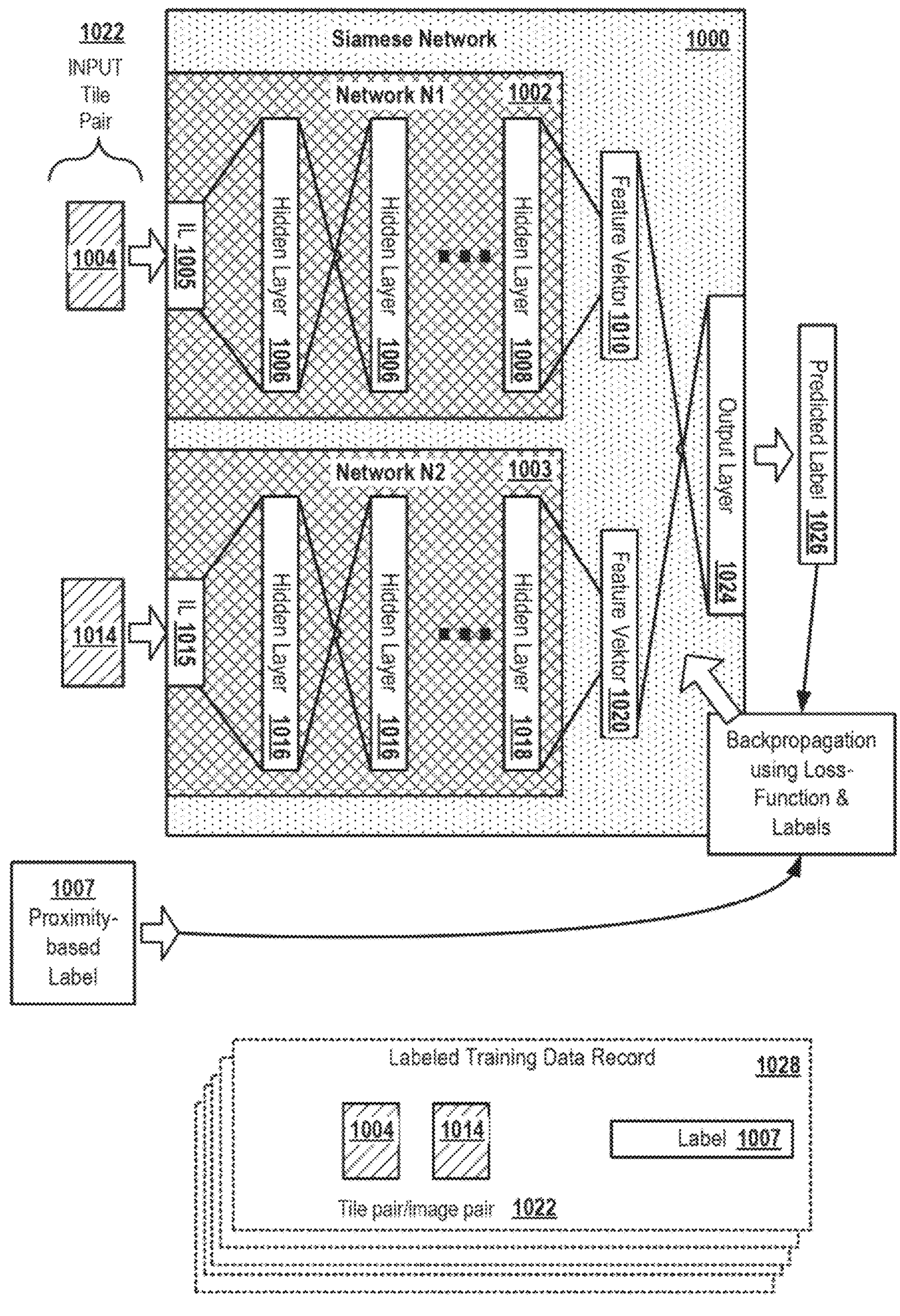
FIG. 10 depicts the architecture of a Siamese network according to an embodiment of the invention.

FIG. 10 depicts the architecture of a Siamese network that is trained according to an embodiment of the invention for providing a sub-network capable of extracting biomedically meaningful feature vectors from image tiles that are suited for performing a feature-vector based similarity search and/or a feature-vector based clustering of tiles. The Siamese network 1000 is trained on an automatically labeled training data set according comprising tile pairs with proximity-based similarity labels that is automatically created as described, for example, with reference to FIGS. 9A and/or 9B.

The Siamese network 1000 consists of two identical sub networks 1002, 1003 joined at their output layer 1024. Each network comprises an input layer 1005, 1015 adapted to receive a single digital image (e.g. a tile) 954, 914 as input. Each sub-network comprises a plurality of hidden layers 1006, 1016, 1008, 1018. A one-dimensional feature vector 1010, 1020 is extracted from one of the two input images by a respective one of the two sub networks. Thereby, the last hidden layer 1008, 1018 of each network is adapted to compute the feature vector and provide the feature vector to the output layer 1024. The processing of the input images is strictly separated. This means, that sub-network only processes the input image 1054 and sub-network only processes the input image 1014. The only point where the information conveyed in the two input images is combined is in the output layer when the output layer compares the two vectors for determining vector similarity and hence, the similarity of the tissue patterns depicted in the two input images.

According to embodiments, each sub-network 1002, 1003 is based on a modified resnet-50 architecture (He et al., Deep Residual Learning for Image Recognition, 2015, CVPR'15). According to embodiments, the resnet-50 pretrained sub-networks 902, 903 were pre-trained on ImageNet. The last layer (that normally outputs 1,000 features) is replaced with a fully connected layer 1008, 1018 of a size having the desired size of the feature vector, e.g. size 128. For example, the last layer 1008, 1018 of each sub-network can be configured to extract features from the second last layer, whereby the second last layer may provide a much greater number of features (e.g. 2048) than the last layer 1008, 1018. According to embodiments, an optimizer, e.g. the Adam optimizer with the default parameters in PyTorch (learning rate of 0.001 and betas of 0.9,0.999), and a batch size of 256 was used during the training. For data augmentation, random horizontal and vertical flips and/or a random rotation up to 20 degrees, and/or a color jitter augmentation with a value of 0.075 for brightness, contrast saturation and/or hue can be applied on the tiles for increasing the training data set.

When the Siamese network is trained on pairs of automatically labeled images, it is the objective of the learning process that similar images should have outputs (feature vectors) that are similar to each other, and dissimilar images should have outputs that are dissimilar to each other. This can be achieved by minimizing a loss function, e.g. a function that measures the difference between the feature vectors extracted by the two sub-networks.

According to embodiments, the Siamese neuronal network is trained on the pairs of tiles using a loss function such that the similarity of the feature vectors extracted by the two sub-networks for the two tiles of the pair respectively correlates with the similarity of the tissue patterns depicted in the two tiles of the pair.

The Siamese network can be, for example, a Siamese network described in Bromley et al., "Signature Verification using a 'Siamese' Time Delay Neural Network, 1994, NIPS'1994. Each sub-network of the Siamese network is adapted to extract a multi-dimensional feature vector from a respective one of two image tiles provided as input. The network is trained on a plurality of tile pairs having been automatically annotated with proximity-based tissue-pattern-similarity labels with the objective that tile pairs depicting similar tissue patterns should have outputs (feature vectors) that are close (similar) to each other, and tile pairs depicting dissimilar tissue patterns should have outputs that are far from each other. According to one embodiment, this is achieved by performing a contrastive loss as described e.g. in Hadsell et al., Dimensionality Reduction by Learning an Invariant Mapping, 2006, CVPR'06. The contrastive loss is minimized during the training. The contrastive loss CL can be computed, for example, according to $$CL=(1-y)2(f1-f2)+y*\max(0,m-L2(f1-f2)),$$

wherein f1, f2 are the outputs two identical sub networks, and y is the ground truth label for the tile pair: 0 if they are labeled "similar" (first set of tile pairs), 1 if they are labeled "dissimilar" (second set of tile pairs).

The training of the Siamese network 1000 comprises feeding the network 1000 with a plurality of automatically labeled similar 912, 913 and dissimilar 914, 915 tile pairs. Each input training data record 1028 comprises the two tiles of the tile pair and its automatically assigned, spatial-proximity-based label 1007. The proximity-based label 10007 is provided as the "ground truth". The output layer 1024 is adapted to compute a predicted similarity label for the two input images 1004, 1014 as a function of the similarity of the two compared feature vectors 1008, 1018. The training of the Siamese network comprises a back propagation process. Any deviation of the predicted label 926 from the input label 1007 is considered to be an "error" or "loss" that is measured in the form of a loss function. The training of the Siamese network comprises minimizing the error computed by the loss function by iteratively using back propagation. The Siamese network 1000 can be implemented, for example, as described by Bromley et al. in "Signature Verification using a "Siamese" Time Delay Neural Network", 1994, NIPS'1994.

Figure 11:
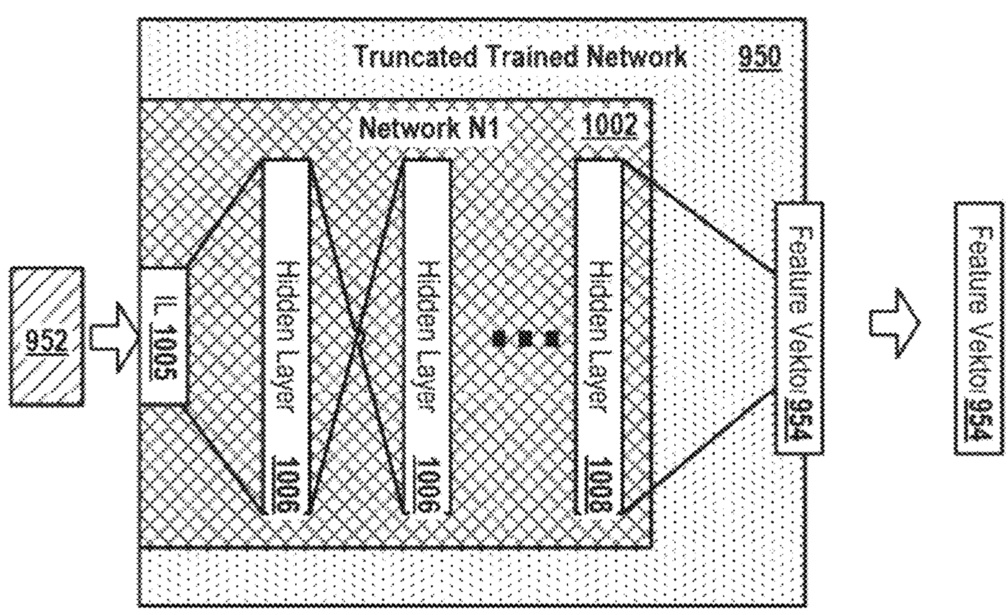
FIG. 11 depicts a feature-extraction MLL implemented as truncated Siamese network.

FIG. 11 depicts a feature-extraction MLL 950 implemented as truncated Siamese network as described, for example, with reference to FIG. 10.

The feature-extraction MLL 950 can be obtained, for example, by storing one of the sub-networks 1002, 1003 of a trained Siamese network 1000 separately. In contrast to the trained Siamese network, the sub-network 1002, 1003 used as the feature-extraction-MLL requires only a single image 952 as input and does not output a similarity label but rather a feature vector 954 that selectively comprises values of a limited set of features having been identified during the training of the Siamese network 1000 as being particularly characteristic for a particular tissue pattern and being particularly suited for determining the similarity of the tissue patterns depicted in two images by extracting and comparing this particular set of features from the two images.

Figure 12:
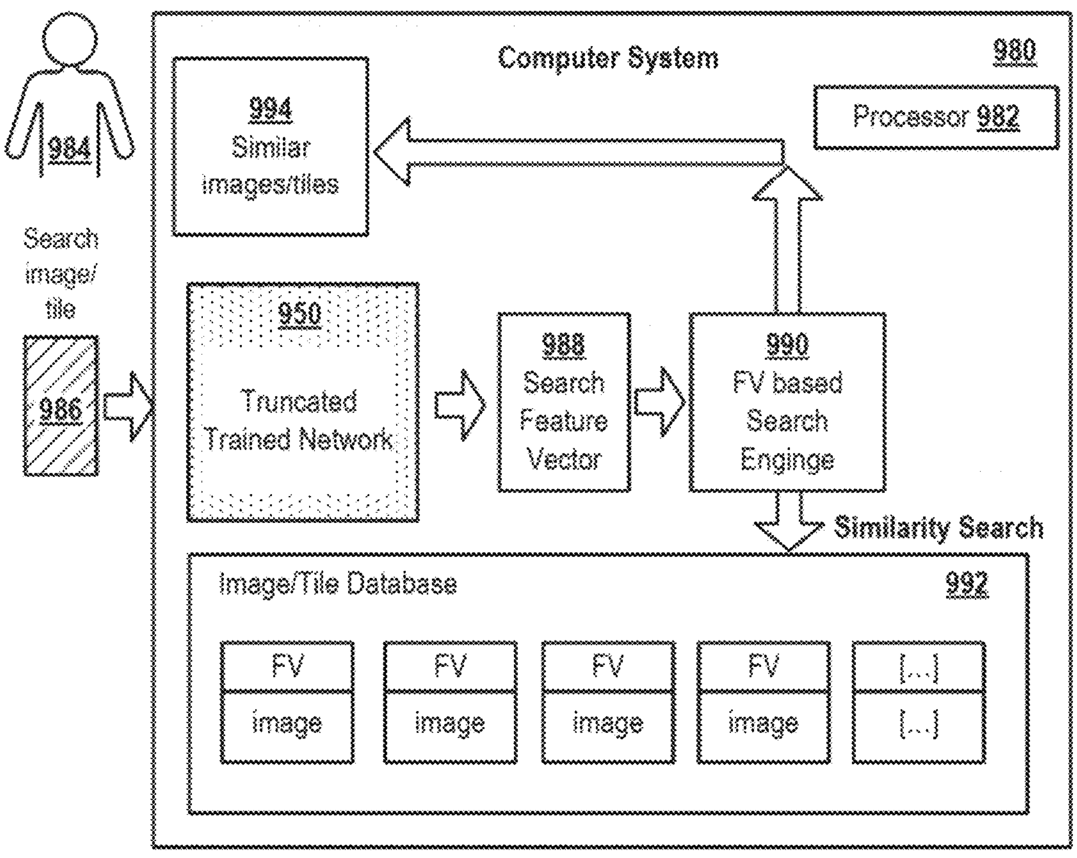
FIG. 12 depicts a computer system using a feature vector based similarity search in an image database.

FIG. 12 depicts a computer system 980 using a feature vector based similarity search in an image database. For example, the similarity search can be used for computing the search tile gallery an example of which is depicted in FIG. 8. The computer system 980 comprises one or more processors 982 and a trained feature-extraction MLL 950 that can be a sub-network of a trained Siamese network ("truncated Siamese network"). The system 980 is adapted to perform an image similarity search using the feature-extraction MLL for extracting a feature vector from the search image and from each of the searched images (tiles), respectively.

The computer system can be, for example, a standard computer system or a server that comprises or is operatively coupled to a database 992. For example, the database can be a relational BDSM comprising hundreds or even thousands of whole slide images depicting tissue samples of a plurality of patients. Preferably, the database comprises, for each of the images in the database, a respective feature vector that has been extracted by a feature output MLL 950 from the said image in the database. Preferably, the computation of the feature vector of each image in the database is performed in a single, pre-processing step before any such request is received. However, it is also possible to compute and extract the feature vectors for the images in the database dynamically in response to a search request. The search can be limited to the tiles of derived from a particular digital image, e.g. for identifying tiles within a single whole slide image that depict a tissue pattern that is similar to the tissue pattern depicted in the search image 986. The search image 986 can be, for example, a tile contained in the report tile gallery that was selected by the user.

The computer system comprises a user interface that enables a user 984 to select or provide a particular image or image tile that is to be used as search image 986. The trained feature-extraction MLL 950 is adapted to extract a feature vector 988 ("search feature vector") from the input image. a search engine 990 receives the search feature vector 988 from the feature output MLL 950 and performs a vector-based similarity search in the image database. The similarity search comprises comparing the search feature vector which each of the feature vectors of the images in the database in order to compute a similarity score as a function of the two compared feature vectors. The similarity score is indicative of the degree of similarity of the search feature vector with the feature vector of the image in the database and hence indicates the similarity of the tissue patterns depicted in the two compared images. The search engine 990 is adapted to return and output a search result 994 to the user. The search result can be, for example, one or more images of the database for which the highest similarity score was computed.

For example, if the search image 986 is an image tile known to depict breast cancer tissue, the system 980 can be used for identifying a plurality of other tiles (or whole slide images comprising such tiles) which depict a similar breast cancer tissue pattern.

FIG. 13 shows two tile matrices, each matrix consisting of three columns, each column comprising six tile pairs. The first (upper) matrix shows a first set of tile pairs (A) consisting of tiles that lie close to each other and that are automatically assigned the label "similar" tile pair. The second (lower) matrix shows a second set of tile pairs (B) lying far from each other and that are automatically assigned the label "dissimilar" tile pair. In some cases "similar" labeled tiles look dissimilar and "not similar" labeled tiles look similar. This noise is caused by the fact that at the border where two different tissue patterns meet, two nearby tiles may depict different tissue patterns and by the fact that even distant tissue regions may depict the same tissue pattern. This is an expected, inherent noise in the dataset generation process.

Applicant has observed that despite of this noise, the feature-extraction MLL trained on the automatically labeled data set is able to accurately identify and extract features that allow a clear distinction of similar and dissimilar tile pairs. Applicant assumes that that the observed robustness of the trained MLLs against this noise is based on the fact that region borders typically have less area than the region non-border areas.

According to embodiments, the quality of the automatically generated training data set is using, in a first step, a previously trained similarity network or an ImageNet pretrained network to assess similarity of tile pairs, then a second step generate the similarity labels based on the spatial proximity of tiles as described herein for embodiments of the invention and then correct the pair labels where a strong deviation of the similarity of the two tiles determined in the first step on the one hand and in the second step in on the other hand is observed.

Figure 14:
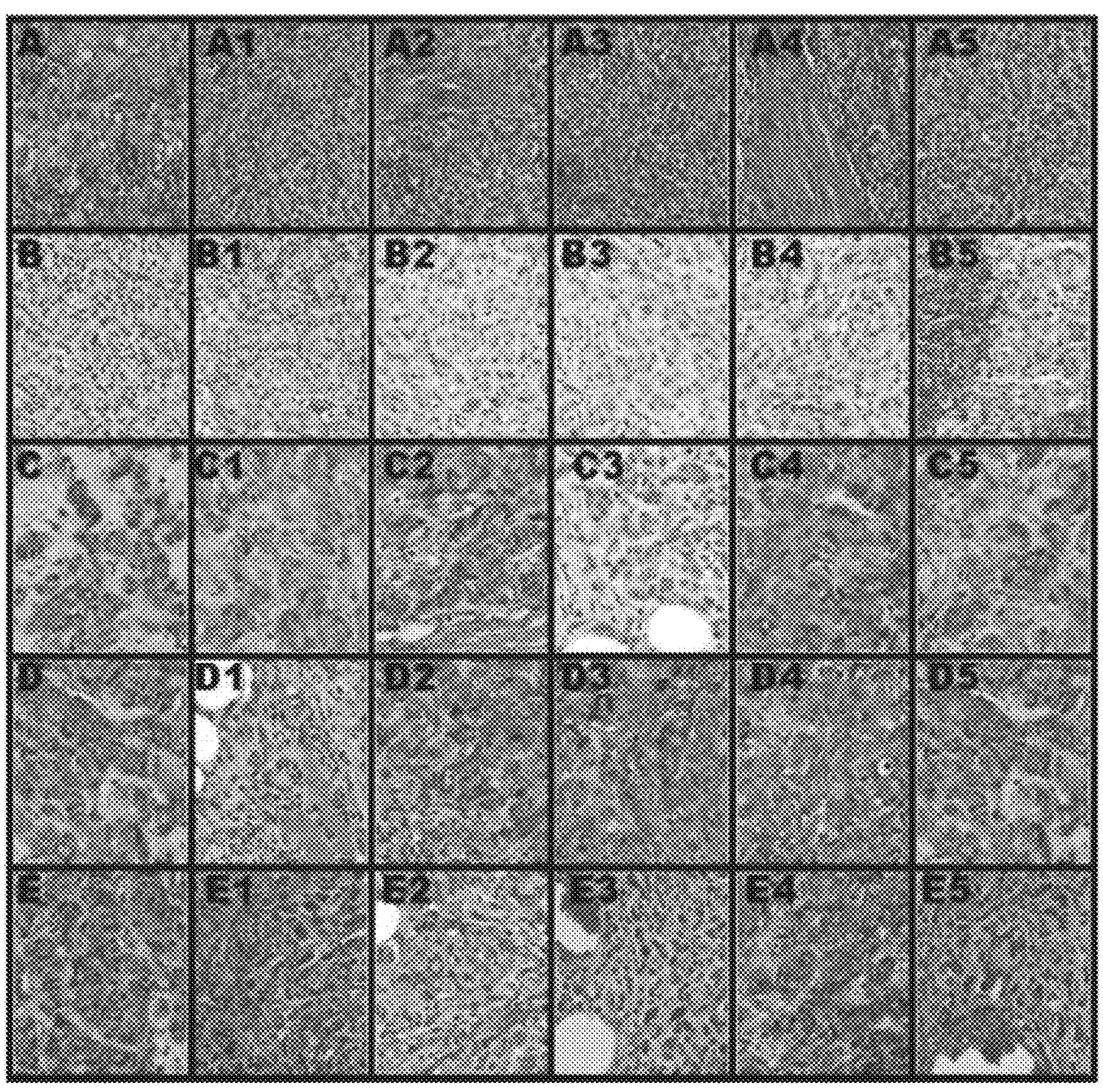
FIG. 14 shows a similarity search result based feature vectors extracted by a feature-extraction MLL trained on an proximity-based similarity labels.

FIG. 14 shows a similarity search result based feature vectors extracted by a feature-extraction MLL trained on an proximity-based similarity labels. The 5 tumor query tiles are referred to as A, B, C, D, and E. The query tiles were used in the image retrieval task for respectively identifying and retrieving the 5 tiles other than the query slide (A1-A5, B1-B5, C1-C5, D1-D5, E1-E5), ranked by distance from low to high, using feature vectors extracted by a feature-extraction MLL trained on an automatically labeled data with proximity based labels. The target class (e.g. tumor) comprises only 3% of the tiles searched. Even though some retrieved tiles look very different than the query tile (e.g. C3 and C) all of the retrieved tiles except A4 have been verified by an expert pathologist to contain tumor cells (i.e. correct class retrieval).

Figure 15:
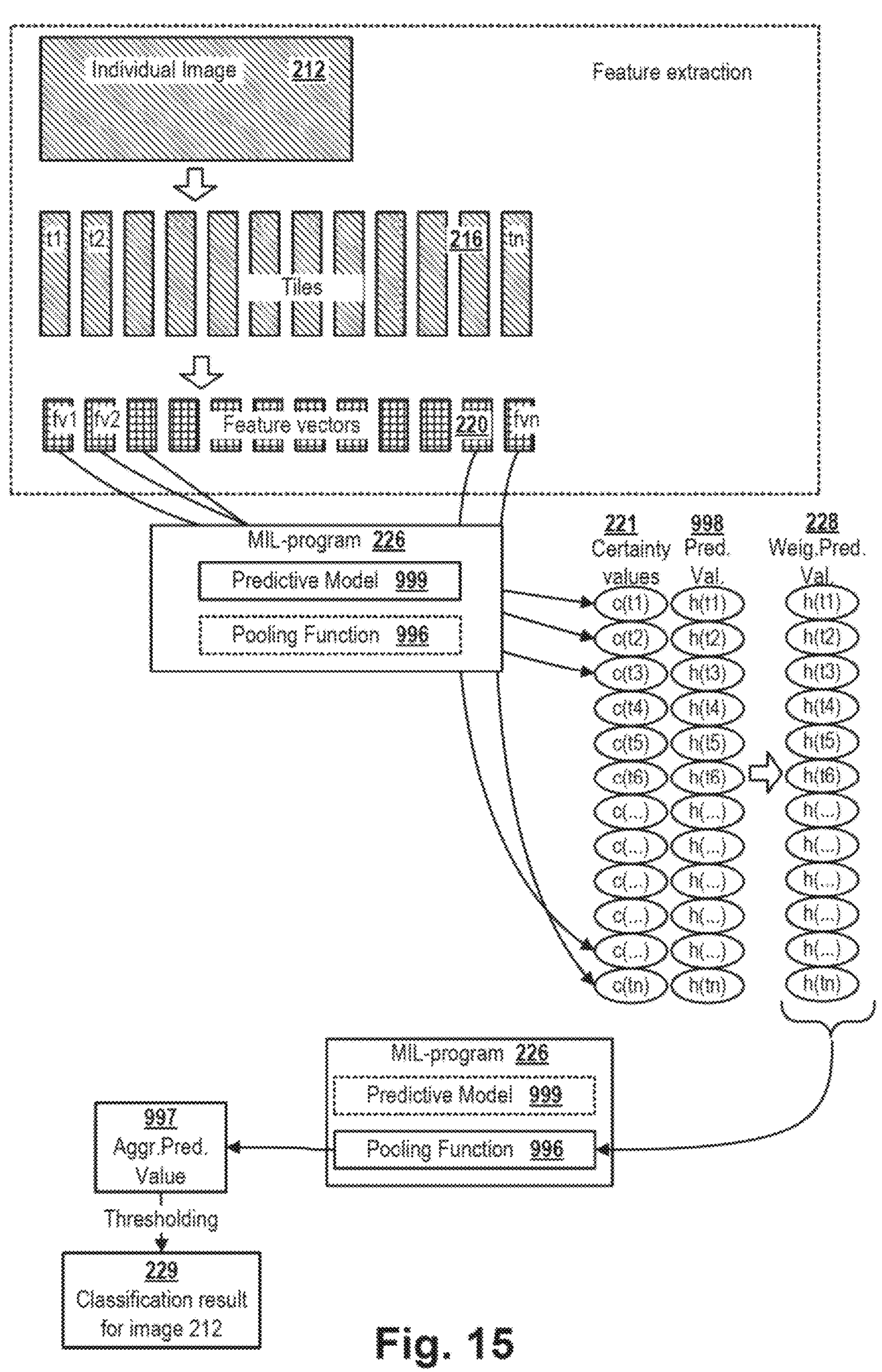
FIG. 15 shows an approach I for image classification that is based on applying the pooling function on predictive values.

FIG. 15 shows an approach I for classifying an input image 212. The image 212 is split into a plurality of tiles 216 and from each of the tiles, a respective feature vector 220 is extracted as described before. The feature vectors are input sequentially into the machine-learning model 999 of the MIL-program 226. The model is configured to compute and output a predictive value h 998 and a certainty value 221 for each feature vector input to the model.

Then, a pooling function 997 is used for computing an aggregated predictive value 997 as a function of both the predictive values 998 and the certainty values 221. For example, the pooling function can aggregate weighted predictive values 228, i.e., predictive values weighted by the certainty value computed by the MIL-model 999 for the tile for which the predictive value was computed. Alternatively, the certainty values can be evaluated by the pooling function for identifying a particular predictive value, e.g. the predictive value of the tile whose certainty value is the highest of all tiles of the image. Then, the aggregated predictive value, which is typically a numerical value normalized to a value within a range of 0 to 1, is used for classifying the image 212. For example, in case the aggregated predictive value 887 is below 0.75, the MIL-program may classify the image to be member of the "negative class" and otherwise to be a member of the "positive class".

Figure 16:
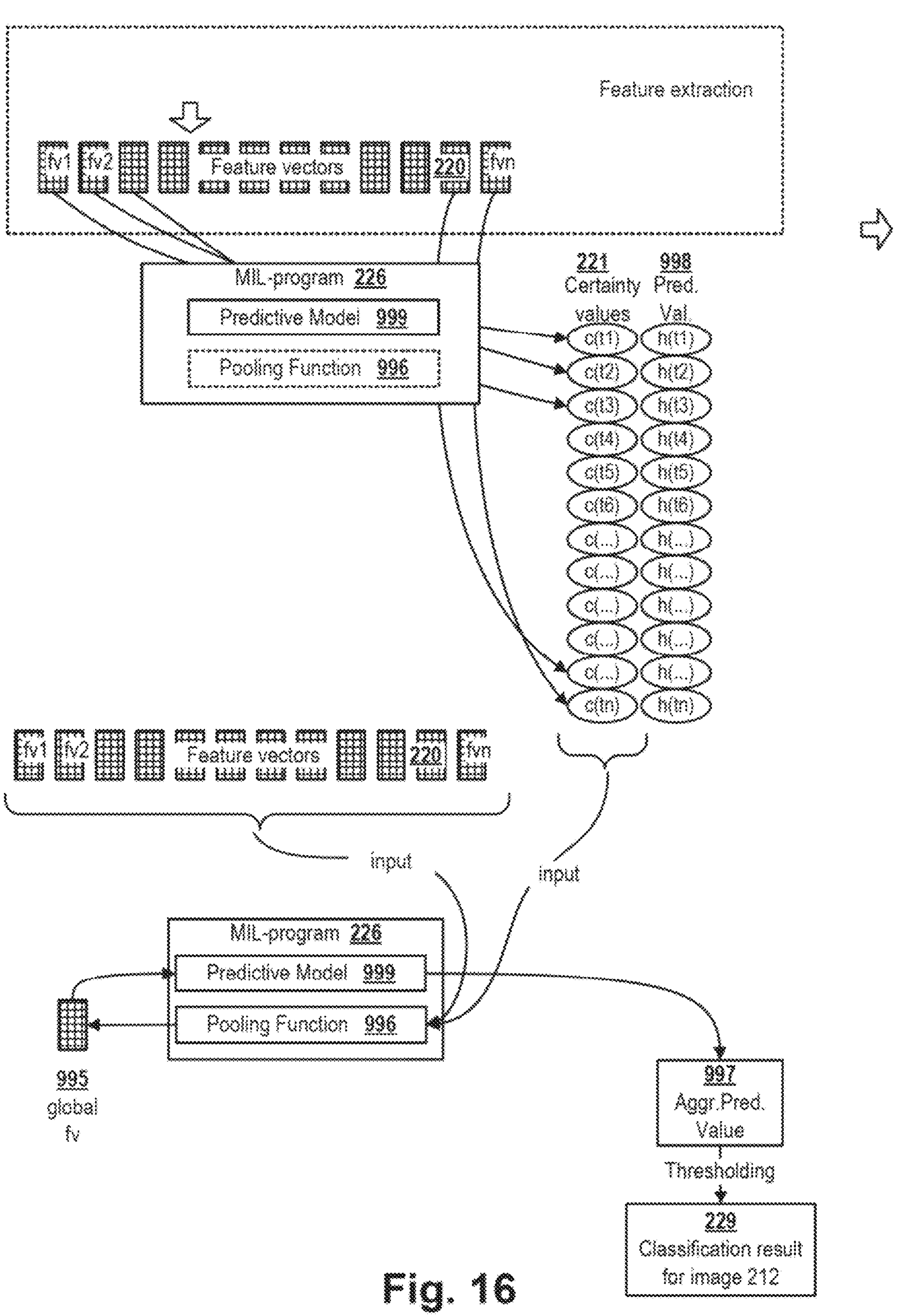
FIG. 16 shows an approach II for image classification that is based on applying a pooling function on feature vectors for obtaining a global feature vector.

FIG. 16 shows an alternative approach II for classifying the image 212. In this approach, the pooling function 996 is applied not on predictive values but rather on the feature vectors extracted from the tiles 216 of the image. This pooling function takes into account the certainty values 221 computed for the tiles. The pooling function computes an aggregated feature vector, also referred to as "global feature vector" 995. This global feature vector conveys information aggregated from multiple features and multiple certainty values of tiles of the image 212. After having computed the global feature vector 995, the vector is input to the machine-learning model 999 of the MIL-program in the same way as a "normal" feature vector fv1, fv2, . . . , fv2 of a tile of the image. The MIL-program computes an aggregated predictive value 997 from the global feature vector in the same way as it has computed any of the predictive values 998 from respective tile-specific feature values, but as the global vector comprises information derived from all the tiles, the predictive value computed from the global value is an aggregate predictive value. Finally, the aggregated predictive value is used for classifying the image 212.

LIST OF REFERENCE NUMERALS

100 method
102-116 steps
200 image analysis system
202 processor(s)
204 display
206 image tile gallery
207 classified images
208 whole slide heat m up ap
210 storage medium
212 digital images
214 splitting module
216 bags of labeled tiles
218 feature extraction module
220 feature vectors
221 certainty values
222 attention machine learning logic program
224 feature vector weights
226 multiple instance learning program
228 numerical relevance scores of the tiles
229 classification result
230 GUI generation module
232 GUI
300 table 1
400 table 2
502 standard neural net
504 neural net after dropout
600 network architecture of feature extraction MLL
602 image tile used as input

603 input layer
604 plurality of layers
606 bottleneck layer
700 GUI comprising report tile gallery
702 first subset of similar tiles 1$^{st}$ tissue pattern
704 2.nd subset of similar tiles representing 2$^{nd}$ tissue pattern
706 3rd subset of similar tiles representing 3$^{rd}$. tissue pattern
708 4th subset of similar tiles representing 4$^{th}$ tissue pattern
710 set of selectable GUI elements
712 whole slide image
714 whole slide image
716 whole slide image
718 whole slide image
722 relevance heat map
724 relevance heat map
726 relevance heat map
728 relevance heat map
800 GUI comprising similarity search tile gallery
802 first subset of similar tiles 1$^{st}$ tissue pattern
804 2.nd subset of similar tiles representing 2$^{nd}$ tissue pattern
806 3rd subset of similar tiles representing 3$^{rd}$. tissue pattern
808 4th subset of similar tiles representing 4$^{th}$ tissue pattern
812 whole slide image
814 whole slide image
816 whole slide image
818 whole slide image
822 similarity heat map
824 similarity heat map
826 similarity heat map
828 similarity heat map
830 query tile
900 digital tissue image sliced into a plurality of tiles
902 tile T1
904 tile T2
906 tile T3
908 first spatial proximity threshold (2D)
910 second spatial proximity threshold (2D)
912 pair of tiles labeled "similar"
913 pair of tiles labeled "similar"
914 pair of tiles labeled "dissimilar"
915 pair of tiles labeled "dissimilar"
916 training data
932 digital tissue image aligned to image 900
934 digital tissue image aligned to image 932
936 first spatial proximity threshold (3D)
938 second spatial proximity threshold (3D)
940 tile T4
942 tile T5
1000 Siamese network
1002 sub-network
1003 sub-network
1004 first input tile
1005 input layer of first network N1
1006 hidden layers
1007 proximity-based ("measured") similarity label
1008 hidden layer for computing a feature vector for 1st input tile
1010 feature vector extracted from the first input tile 904
1014 second input tile
1015 input layer of second network N2
1016 hidden layers
1018 hidden layer for computing a feature vector for 2nd input tile
1020 feature vector extracted from the second input tile 914
1022 pair of input tiles
1024 output layer joining networks N1, N2
1026 predicted similarity label
1028 individual data record of training data set
950 feature-extraction MLL
952 individual input image/tile
954 feature vector
980 computer system
982 processor
984 user
986 individual input image/tile
988 search feature vector
990 feature vector-based search engine
992 database comprising a plurality of images or tiles
994 returned similarity search results
995 global feature vector
996 certainty-value-based pooling function
997 aggregated predictive value
998 predictive value(s)
999 predictive model

The invention claimed is:

1. A method for classifying tissue images, the method comprising:
receiving, by an image analysis system, a plurality of digital images, each of the digital images depicting a tissue sample of a patient;
splitting, by the image analysis system, each received image into a set of image tiles;
for each of the tiles, computing, by the image analysis system, a feature vector comprising image features extracted selectively from the tile;
providing a Multiple-Instance-Learning (MIL) program configured to use a model for classifying any input image as a member of one out of at least two different classes based on the feature vectors extracted from all tiles of the said input image, wherein the MIL-program is a neural network;
for each of the tiles, computing a certainty value, the certainty value being indicative of the certainty of the model regarding the contribution of the tile's feature vector on the classification of the image from which the tile was derived, wherein the certainty-value is computed using a dropout technique at test time of the model of the neural network;
for each of the images,
using, by the MIL-program, a certainty-value-based pooling function for aggregating the feature vectors extracted from the image into a global feature vector as a function of the certainty values of the tiles of the image, and computing an aggregated predictive value from the global feature vector; or
computing, by the MIL program, a predictive value from each of the feature vectors of the image and using, by the MIL-program, the certainty-value-based pooling function for aggregating the predictive values of the image into an aggregated predictive value as a function of the certainty values of the tiles of the image; and
classifying, by the MIL-program, each of the images as a member of one out of the at least two different classes based on the aggregated predictive value.

2. The method of claim 1, further comprising:

outputting, via a GUI, the classification result to a user; and/or outputting the classification result to another application program.

3. The method of claim 1, wherein the MIL-program is a binary MIL-program, wherein the at least two classes consist of a first class referred to as "positive class" and a second class referred to as "negative class", wherein any one of the images is classified into the "positive class" if the MIL model predicts for at least one of the tiles of this image that the feature vector of this tile comprises evidence for the "positive class", wherein any one of the images is classified into the "negative class" if the MIL model predicts for all the tiles of this image that their respective feature vectors do not comprises evidence for the "positive class".

4. The method of claim 1, the certainty-value-based-pooling function being used at test time, the providing of the MIL-program comprising:

extracting feature vectors from a set of training tiles generated from a set of training images;

training the MIL-program on the feature vectors, using at training time the same certainty-value-based-pooling function as used at test time or using at training time another certainty-value-based-pooling function than the certainty-value-based-pooling function as used at test time, wherein the certainty-value-based-pooling function used at training time is a certainty-value-based-max-pooling function or a certainty-value-based-mean-pooling function and wherein the certainty-value-based-pooling function used at test time is a certainty-value-based-max-pooling function.

5. The method of claim 1, wherein the certainty-value-based pooling function is a certainty-value-based-max-pooling function, wherein the using of the certainty-value-based pooling function comprises, for each of the images, a sub-method a), b, c) or d), respectively comprising:

a1) weighting the predictive value of each of the tiles with the certainty value computed for this tile, thereby obtaining a weighed predictive value;

a2) identifying the maximum of all weighted predictive values computed for all the tiles of the image; and a3) using the maximum weighted predictive value as the aggregated predictive value; or b) using the predictive value of the tile with the maximum certainty value as the aggregated predictive value; or c1) weighting the feature vector of each of the tiles with the certainty value computed for this tile, thereby obtaining a weighed feature vector;

c2) identifying the maximum of all weighted feature vectors computed for all the tiles of the image; or d) using the feature vector of the tile with the maximum certainty value as the global feature vector.

6. The method of claim 1, wherein the certainty-value-based pooling function is a certainty-value-based-mean-pooling function, wherein the using of the certainty-value-based pooling function comprises, for each of the images:

weighting the feature vector of each of the tiles with the certainty value computed for this tile, thereby obtaining a weighted feature vector; and computing the global feature vector as the mean of all the weighted feature vectors of the image; or weighting the predictive value of each of the tiles with the certainty value computed for this tile, thereby obtaining a weighted predictive value; computing the mean of the weighted predictive values of the image; and using the computed mean as the aggregated predictive value.

7. The method of claim 1, wherein the certainty-value is further computed using the dropout technique at training of the model of the neural network.

8. The method of claim 7, wherein the certainty-value is computed as Monte-Carlo Dropout.

9. The method of claim 1, wherein the dropout technique and/or the certainty-value-based pooling function is used at test time but not at training time of the model.

10. The method of claim 8, wherein the neural network comprises one or more deactivated dropout layers, wherein a deactivated dropout layer is a dropout layer activated at training time and deactivated at test time, the method comprising reactivating the one or more dropout layers at test time; or wherein the neural network at training time is free of any dropout layer, the method comprising adding one or more dropout layers at test time to the neural network; and wherein the computing of the certainty value for any one of the tiles at test time further comprises:

computing, for each of the tiles, multiple times a predictive value based on the feature vector extracted from the tile, wherein each time the predictive value is computed a different subset of nodes of the network is dropped by the one or more reactivated or added dropout layers; and computing, for each of the tiles, the certainty value of the tile as a function of the variability of the multiple predictive values computed for the tile, wherein the larger the variability, the lower the certainty value.

11. The method of claim 1, the received digital images comprising:

digital images of tissue samples whose pixel intensity values correlate with the amount of a non-biomarker specific stain; and/or digital images of tissue samples whose pixel intensity values correlate with the amount of a biomarker specific stain, the biomarker-specific stain adapted to selectively stain a biomarker contained in the tissue sample.

12. The method of claim 1, the providing of the MIL-program comprising training the model of the MIL-program, the training comprising one or more of:

providing a set of digital training images of tissue samples, each digital training image having assigned a class label being indicative of one of the at least two classes;

splitting each training image into training image tiles, each training tile having assigned the same class label as the digital training image from which the training tile was derived;

for each of the training tiles, computing, by the image analysis system, a training feature vector comprising image features extracted selectively from the said tile; and repeatedly adapting the model of the MIL-program such that an error of a loss function is minimized, the error of the loss function indicating a difference of predicted class labels of the training tiles and the class labels actually assigned to the training tiles, the predicted class labels having been computed by the model based on the feature vector of the training tiles.

13. The method of claim 1, further comprising, for each of the received digital images:

weighting the predictive value of each of the tiles with the certainty value computed for this tile, thereby obtaining a weighted predictive value;

identifying, by the MIL-program, the one of the tiles of the image for which the highest weighted predictive value was computed;

for each of the other tiles of the image, computing a relevance indicator by comparing the weighted predictive value of the other tile with the highest weighted predictive value, wherein the relevance indicator is a numerical value that negatively correlates with the difference of the compared weighted predictive values;

computing a relevance heat map for the image as a function of the relevance indicator, the pixel color and/or pixel intensities of the relevance heat map being indicative of the relevance indicator computed for the tiles in the said image; and displaying the relevance heat map on a GUI.

14. The method of claim 1, further comprising:

displaying the received images on a GUI of a screen, the images being grouped in the GUI into the at least two different classes in accordance with a result of the classification.

15. The method of claim 1, wherein each of the at least two classes is selected from a group comprising:

a patient being responsive to a particular drug;

a patient having developed metastases or a particular form of metastases;

a cancer patient showing a particular response to a particular therapy;

a cancer patient tissue showing a particular morphological state or microsatellite status;

a patient has developed adverse reaction to a particular drug;

a patient having a particular genetic attribute; and/or a patient having a particular RNA expression profile.

16. The method of claim 1, wherein the certainty-value-based pooling function is a certainty-value based max-pooling, mean-pooling or an attention pooling function.

17. The method of claim 1, further comprising:

providing a trained attention-MLL having learned which tile-derived feature vectors are the most relevant for predicting class membership for a respective tile;

computing an attention weight for each of the tiles as a function of the feature vector of the respective tile by the attention-MLL, the attention weight being an indicator of the relevance of the respective tile's feature value in respect to a membership of the respective tile to a class; and multiplying the attention weight of the respective tile with the respective tile's feature vector values for obtaining an attention-based feature vector with attention-weighted feature values for the respective tile; and wherein the method further comprises:

using the attention-based feature vector as the feature vector that is input to the MIL-program for computing the predictive value, the certainty value and/or the weighted predictive value of the respective tile, the predictive value, the certainty value and/or the weighted predictive value thereby being computed as attention-based predictive value, an attention-based certainty value and/or as an attention-based weighted predictive value; or multiplying the attention weight of the respective tile with the respective tile's predictive value, the certainty value or with the respective tile's weighted predictive value computed by the MIL for obtaining an attention-based predictive value, an attention-based certainty value and/or an attention-based weighted predictive value.

18. An image analysis system for classifying tissue images, comprising:

at least one processor;

a volatile or non-volatile storage medium comprising digital images respectively depicting a tissue sample of a patient;

an image splitting module being executable by the at least one processor and being configured to split each of the images into a set of image tiles;

a feature extraction module being executable by the at least one processor and being configured to compute, for each of the tiles, a feature vector comprising image features extracted selectively from the said tile;

a Multiple-Instance-Learning (MIL) program being executable by the at least one processor and being configured to use a model for classifying any input image as a member of one out of at least two different classes based on the feature vectors extracted from all tiles of the said input image, wherein the MIL-program is a neural network, and wherein the MIL-program is further configured for:

for each of the tiles, computing a certainty value, the certainty value being indicative of the certainty of the model regarding the contribution of the tile's feature vector on the classification of the image from which the tile was derived, wherein the certainty-value is computed using a dropout technique at test time of the model of the neural network;

for each of the images:

using, by the MIL-program, a certainty-value-based pooling function for aggregating the feature vectors extracted from the image into a global feature vector as a function of the certainty values of the tiles of the image, and computing an aggregated predictive value from the global feature vector; or computing, by the MIL program, a predictive value from each of the feature vectors of the image and using, by the MIL-program, a certainty-value-based pooling function for aggregating the predictive values of the image into an aggregated predictive value as a function of the certainty values of the tiles of the image; and classifying, by the MIL-program, each of the images as a member of one out of the at least two different classes based on the aggregated predictive value.

19. The method of claim 11, wherein the non-biomarker specific stain is a hematoxylin stain or an H&E stain.

20. The method of claim 15, wherein the particular response is a pathologic complete response, and wherein the particular genetic attribute is a particular gene signature.

* * * * *